US010919945B2

(12) United States Patent
Rose et al.

(10) Patent No.: US 10,919,945 B2
(45) Date of Patent: Feb. 16, 2021

(54) MODULAR ANTIGEN TRANSPORTATION MOLECULES AND USES THEROF

(71) Applicant: Boehringer Ingelheim Vetmedica GmbH, Ingelheim am Rhein (DE)

(72) Inventors: Horst Rose, Burgdorf (DE); Dania Birte Reiche, Bingen am Rhein (DE); Harald Tammen, Hannover (DE)

(*) Notice: Subject to any disclaimer, the term of this patent is extended or adjusted under 35 U.S.C. 154(b) by 140 days.

(21) Appl. No.: 15/882,455

(22) Filed: Jan. 29, 2018

(65) Prior Publication Data
US 2018/0170978 A1 Jun. 21, 2018

Related U.S. Application Data

(62) Division of application No. 14/670,670, filed on Mar. 27, 2015, now Pat. No. 9,920,101.

(30) Foreign Application Priority Data

Mar. 31, 2014 (EP) ..................... 14162575

(51) Int. Cl.
| | | |
|---|---|---|
| C07K 14/435 | (2006.01) |
| C07K 14/415 | (2006.01) |
| C07K 14/005 | (2006.01) |
| A61K 39/35 | (2006.01) |
| A61K 39/00 | (2006.01) |

(52) U.S. Cl.
CPC ........ *C07K 14/43563* (2013.01); *A61K 39/35* (2013.01); *C07K 14/005* (2013.01); *C07K 14/415* (2013.01); *A61K 2039/552* (2013.01); *A61K 2039/55505* (2013.01); *A61K 2039/60* (2013.01); *C07K 2319/00* (2013.01); *C07K 2319/01* (2013.01); *C07K 2319/06* (2013.01); *C07K 2319/10* (2013.01); *C07K 2319/21* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 5,633,234 A | 5/1997 | August et al. |
| 5,804,604 A | 9/1998 | Frankel et al. |
| 7,563,866 B2 | 7/2009 | Lamping et al. |
| 2005/0281816 A1 | 12/2005 | Lamping et al. |
| 2008/0108561 A1 | 5/2008 | Nandy et al. |
| 2014/0039163 A1 | 2/2014 | Nagamune et al. |
| 2014/0105906 A1 | 4/2014 | Venugopal et al. |
| 2015/0274790 A1 | 10/2015 | Rose et al. |
| 2017/0087246 A1 | 3/2017 | Rose et al. |

FOREIGN PATENT DOCUMENTS

| | | |
|---|---|---|
| EP | 1621615 A1 | 2/2006 |
| JP | 2008504004 A | 2/2008 |
| JP | 2011212008 A | 10/2011 |
| JP | 2012010707 A | 1/2012 |
| WO | 199418999 A1 | 9/1994 |
| WO | 200031273 A2 | 6/2000 |
| WO | 2004035793 A1 | 4/2004 |
| WO | 2004094639 A2 | 11/2004 |
| WO | 2007065633 A1 | 6/2007 |
| WO | 2009022154 A2 | 2/2009 |
| WO | 2009156448 A1 | 12/2009 |
| WO | 2012121395 A1 | 9/2012 |
| WO | 2015150243 A1 | 10/2015 |
| WO | 2017055235 A1 | 4/2017 |

OTHER PUBLICATIONS

Bowie et al. (Science, 1990, 247:1306-1310).*
Greenspan et al. (Nature Biotechnology 7: 936-937, 1999).*
"Conference: Report of the 3rd Havemeyer workshop on allergic diseases of the Horse, Holar, Iceland, Jun. 2007". Veterinary Immunology and Immunopathology, vol. 126, 2008, pp. 351-361.
"Vaccine" Encyclopedia Brittanica Online, Accessed at [www.search.eb.com/eb/print?eu=76559 on Mar. 22, 2004.] 1 page.
Abstract in English of JP2011212008, Oct. 27, 2011.
Akdis et al., "Mechanisms and treatment of allergic disease in the big picture of regulatory T cells". Clinical Reviews in Allergy and Immunology, vol. 123, 2009, pp. 735-746.
Bodey et al., "Failure of Cancer Vaccines: The Significant Limitations of this Approach to Immunotherapy". Anticancer Research, vol. 20, 2000, pp. 2665-2676.
Bonini et al., "Targeting Antigen in Mature Dendritic Cells for Simultaneous Stimulation of CD4+ and CD8+ T Cells". The Journal of Immunology, vol. 166, No. 8, Apr. 2001, pp. 5250-5257.
Boon eta al., "Human T Cell Responses Against Melanoma". Annual Review of Immunology, vol. 24, 2006, pp. 175-208.
Corradin et al., "Medicinal application of long synthetic peptide technology". Expert Opinion on Biological Therapy, vol. 4, No. 10, 2004, pp. 1629-1639.
Durham et al., "Grass pollen immunotherapy inhibits allergen-induced infiltration of CD4+ T lymphocytes and eosinophils in the nasal mucosa and increases the number of cells expressing messenger RNA for interferon-g". Journal of Allergy and Clinical Immunology, vol. 97, No. 6, 1996, pp. 1356-1365.

(Continued)

*Primary Examiner* — Brian Gangle
(74) *Attorney, Agent, or Firm* — Steffan Finnegan

(57) ABSTRACT

The present invention relates to (isolated) recombinant proteins, also referred to as improved MAT (iMAT) molecules, comprising at least one translocation module, at least one targeting module and at least one antigen module, wherein at least one cysteine residue is substituted with a different amino acid residue. Such iMAT molecules are useful specifically as vaccines, e.g., for therapy and/or prevention of allergies and/or infectious diseases and/or prevention of transmission of infectious diseases in equines. The present invention further relates to nucleic acids encoding such iMAT molecules, corresponding vectors and primary cells or cell lines.

Figure 2A:
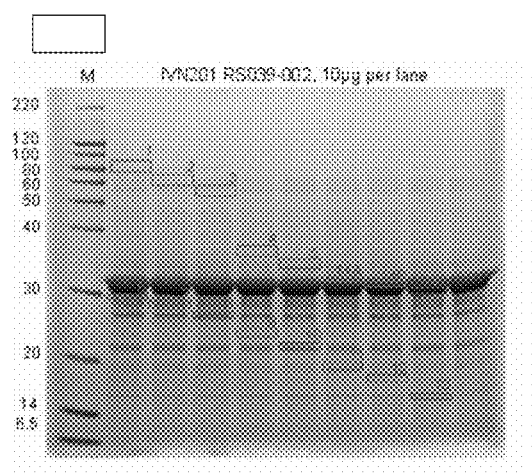

1 Claim, 9 Drawing Sheets
Specification includes a Sequence Listing.

(56) References Cited

OTHER PUBLICATIONS

Fahey et al., "Status of immune-based therapies in HIV infection and AIDS". Clinical & Experimental Immunology, vol. 88, 1992, pp. 1-5.
Ford et al., "Protein transduction: an alternative to genetic intervention?" Gene Therapy, vol. 8, No. 1, 2001, pp. 1-4.
Fujii et al., "The CLIP-Substituted Invariant Chain Efficiently Targets an Antigenic Peptide to HLA Class II Pathway in L Cells". Human Immunology, vol. 59, 1998, pp. 607-614.
Gadermaier et al., "Targeting the cysteine-stabilized fold of Art v 1 for immunotherapy of Artemisia pollen allergy". Molecular Immunology, vol. 47, No. 6, 2010, pp. 1292-1298.
Ginel et al., "Allergen-specific immunotherapy in horses with insect bite hypersensitivity: a double-blind, randomized, placebo-controlled study". Veterinary Dermatology, vol. 25, 2014, pp. 29-34, e9-10.
Hare et al., "Evaluation of an In Vitro Degranulation Challenge Procedure for Equine Pulmonary Mast Cells". Canadian Journal of Veterinary Research, vol. 62, 1998, pp. 133-139.
Hoffmann-Sommergruber et al., "IgE reactivity to Api g 1, a major celery allergen, in a Central European population is based on primary sensitization by Bet v 1". The Journal of Allergy and Clinical Immunology, vol. 104, No. 2, Part 1, 1999, pp. 478-484.
International Search Report and Written Opinion for PCT/EP2015/056670 dated Sep. 11, 2015.
James et al., "Update on mechanisms of allergen injection immunotherapy". Clinical and Experimental Allergy, vol. 38, 2008, pp. 1074-1088.
Josephson et al., "High-Efficiency Intracellular Magnetic Labeling with Novel Superparamagnetic-Tat Peptide Conjugates". Bioconjugate Chemistry, vol. 10, No. 2, 1999, pp. 186-191.
Kehrli et al., "Multiple Hypersensitivities Including Recurrent Airway Obstruction, Insect Bit Hypersensitivity, and Urticaria in 2 Warmblood Horse Populations". Journal of Veterinary Internal Medicine, vol. 29, 2015, pp. 320-326.
Kelley et al., "Comparative genomics of major histocompatability complexes". Immunogenetics, vol. 56, 2005, pp. 683-695.
Klein et al., "Design and characterization of structured protein linkers with differing flexibilities". Protein Engineering, Design & Selection, vol. 27, No. 10, 2014, pp. 325-330.
Kyte et al., "A Simple Method for Displaying the Hydropathic Character of a Protein". Journal of Molecular Biology, vol. 157, 1982, pp. 105-132.
Landholt et al., "Low-dose DNA vaccination into the submandibular lymph nodes in ponies". Veterinary Record, vol. 167, 2010, pp. 302-304.
Langner et al., "Comparison of cellular and humoral immunoassays for the assessment of summer eczema in horses". Veterinary Immunology and Immunopathology, vol. 122, 2008, pp. 126-137.
Leclere et al., "Heaves, an asthma-like disease of horses". Respirology, vol. 16, 2011, pp. 1027-1046.
Letvin, Normal L. "Progress in the Development of an HIV-1 Vaccine". Science, vol. 280, 1998, pp. 1875-1880.
Machuca et al., "Human Immunodeficiencey Virus Type 2 Infection in Spain". Intervirology, vol. 42, 1999, pp. 37-42.
Mai et al., "Efficiency of Protein Transduction Is Cell Type-dependent and Is Enhanced by Dextran Sulfate". The Journal of Biological Chemistry, vol. 277, No. 33, Aug. 2002, pp. 30208-30218.
Marchand et al., "Biological and clinical developments in melanoma vaccines". Expert Opinion on Biology Therapy, vol. 1, No. 3, 2001, pp. 497-510.
Martinez-Gomez et al., "Targeting the MHC class II pathway of antigen presentation enhances immunogenicity and safety of allergen immunotherapy". Allergy, vol. 64, No. 1, 2008, pp. 172-178.
Merck Manual, 16th Edition, Berkow, ed., Rahway, NJ, Merck & Co., Inc., 1992, pp. 20-21.
Möbs et al. "Cellular and Humoral Mechanisms of Immune Tolerance in Immediate-Type Allergy Induced by Specific Immunotherapy". International Archives of Allergy and Immunology, vol. 147, 2008, pp. 171-178.
Nakano et al., "Positive Selection of T Cells Induced by Viral Delivery of Neopeptides to the Thymus". Science, vol. 275, Jan. 1997, pp. 678-683.
NCBI Accession No. AAH18726, "CD74 molecule, major histocompatibility complex, class II invariant chain [*Home sapiens*]". Jul. 15, 2006, pp. 1-3.
Niederberger et al., "Vaccination with genetically engineered allergens prevents progression of allergic disease". Proceedings of the National Academy of Sciences, vol. 101, Supp. 2, 2004, pp. 14677-14682.
Olsen et al., "Pharmacokinetics and effects of cetirizine in horses with insect bite hypersensitivity". The Veterinary Journal, vol. 187, 2011, pp. 347-351.
Peeters et al., "Evaluation of an IgE ELISA with *Culicoides* spp. extracts and recombinant salivary antigens for diagnosis of insect bite hypersensistivity in Warmblood horses." The Veterinary Journal, vol. 198, 2013, pp. 141-147.
Pires et al., "mCSM: predicting the effects of mutations in proteins using graph-based signatures". Bioinformatics, vol. 30, No. 3, 2014, 335-342.
Pirie, R.S. "Recurrent airway obstruction: A review". Equine Veterinary Journal, vol. 46, 2014, pp. 276-288.
Platts-Mills et al., "Current reviews of allergy and clinical immunology". The Journal of Allergy and Clinical Immunology, vol. 102, No. 3, 1998, pp. 335-343.
Rath et al. "Detergent binding explains anomalous SDS-PAGE migration of membrane proteins". Proceedings of the National Academy of Sciences, vol. 106, No. 6, 2009, pp. 1760-1765.
Rodriguez et al., "CD4+ T Cells Induced by a DNA Vaccine: Immunological Consequences of Epitope-Specific Lysosomal Targeting". Journal of Virology, vol. 75, No. 21, Nov. 2001, pp. 10421-10430.
Rose, Horst, "IVN201—Therapy With a Construct Containing Functional Fusion Peptides". 12th International Paul Ehrlich Seminar, Bad Homburg, vol. 96, 2008, pp. 319-328.
Rothbard et al., "Transport of immunogens into the MHC class I and II pathways by a peptide from HIV tat". KLA and Disease—The Molecular Basis, Alfred Beazon Symposium, 1997, pp. 161-171.
Sanderson et al., "Expression of endogenous peptide-major histocompatibility complex class II complexes derived from invariant chain-antigen fusion proteins". Proceedings of the National Academy of Sciences, vol. 92, Aug. 1995, pp. 7217-7221.
Schaffartzik et al., "Equine insect bit hypersensitivity: What do we know?" Veterinary Immunology and Immunopathology, vol. 147, No. 3, 2012, pp. 113-126.
Schwartz et al., "Multipel Sclerosis as a By-Product of the Failure to Sustain Protective Autoimmunity: A Paradigm Shift". The Neuroscientist, vol. 8, No. 5, 2002, pp. 405-413.
Senti et al., "Intralymphatic immunotherapy for cat allergy induces tolerance after only 3 injections". Journal of Allergy and Clinical Immunology, vol. 129, No. 5, 2012, pp. 1290-1296.
Sheldon et al., "Loligomers: Design of de novo peptide-based intracellular vehicles". Proceedings of the National Academy of Sciences, vol. 92, Mar. 1995, pp. 2056-2060.
Suzuki et al., "Possible Existence of Common Internalization Mechanisms among Arginine-rich Peptides". The Journal of Biological Chemistry, vol. 277, Jan. 2002, pp. 2437-2443.
Thomson et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design". Journal of Virology, vol. 72, No. 3, Mar. 1998, pp. 2246-2252.
Tilley et al. "Comparison of Skin Prick Tests with In Vitro Allergy Tests in the Characterization of Horses with Recurrent Airway Obstruction". Journal of Equine Veterinary Science, vol. 32, 2012, pp. 719-727.
Tisch et al., "Antigen-specific immunotherapy: Is it a real possibility to combat T-cell-mediated autoimmunity?" Proceedings of the National Academy of Sciences, vol. 91, 1994, pp. 437-438.
UniProtKB Accession No. Q9MXD5. "MHC class II associated invariant chain." Oct. 1, 2000, pp. 1-4.

(56) References Cited

OTHER PUBLICATIONS

Vad Der Meide et al., "Cloning and expression of candidate allergens from Culicoides obsoletus for diagnosis of insect bite hypersensitivity in horses." Veterinary Immunology and Immunopathology, vol. 153, 2013, pp. 227-239.
Van Bergen et al., "Get into the Groove! Targeting antigens to MHC class II". Immunological Reviews, vol. 172, 1999, pp. 87-96.
Van Der Meide et al., "Evaluation of a diagnostic ELISA for insect bit hypersensitivity in horses using recombinant Obsoletus complex allergens". The Veterinary Journal, vol. 200, 2014, pp. 31-37.
Van Overtvelt et al., "Assessment of Bet v 1-Specific CD4+ T Cell Responses in Allergic and Nonallergic Individuals Using MHC Class II Peptide Tetramers". The Journal of Immunology, vol. 180, 2008, pp. 4514-4522.
Vazquez-Boland et al., "Rhodococcus equi: The many facets of a pathogenic actinomycete". Veterinary Microbiology, vol. 167, 2013, pp. 9-33.
Von Bargen et al., "Molecular and infection biology of the horse pathogen *Rhodococcus equi*". FEMS Microbiology Review, vol. 33, 2009, pp. 870-891.
Wachholz et al. "Inhibition of allergen-IgE binding to B cells by IgG antibodies after grass pollen immunotherapy". Journal of Allergy and Clinical Immunology, vol. 112, Nov. 2003, pp. 915-922.
Yang et al., "Expression of hypoallergenic Der f2 derivatives with alterned intramolecular disulphide bonds induces the formation of novel ER-derived protein bodies in transgenic rice seeds." Journal of Experimental Botany, vol. 63, No. 8, 2012, pp. 2947-2959.
Anderson G et al.; "Immunotherapy Trial for Horses in British Columbia with Culicoides (Diptera: Ceratopogonidae) Hypersensitivity," Journal of Medical Entomology, 1996, vol. 22, No. 3, p. 458-466.
Balapala K et al.; "Hypersensitivity and Pathophysiology following Insect Bites!," Journal of Pharmaceutical and Biological Sciences, 2016, 4(5), p. 155-159.
Barbet J et al.; "Specific immunotherapy in the treatment of Culicoides hypersensitive horses: A double-blind study," Equine Veterinary Journal, 1990, 22(4), p. 232-235.
Crameri R et al.; "Design, engineering and in vitro evaluation of MHC class-II targetingallergy vaccines," Allergy, 2007, vol. 62, p. 197-206.
Curin M et al.; "Hypoallergenic derivatives of Fel d 1 obtained by rational reassembly for allergy vaccination and tolerance induction," Clin Exp. Allergy, 2014, 44(6), p. 882-894.
Durward-Akhurst S et al.; "Major Histocompatibility Complex I and II Expression and Lymphocytic Subtypes in Muscle of Horses with Immune-Mediated Myositis," Journal of Veterinary Internal Medicine, 2016, 30, p. 1313-1321.
Eder C et al.; "Allergen-speci® c IgE levels against crude mould and storage mite extracts and recombinant mould allergens in sera from horses affected with chronic bronchitis," Veterinary Immunology and Immunopathology, 200, 73, p. 241-253.
Einhom L et al.; "Molecular allergen profiling in horses by microarray reveals Fag e 2 from buckwheat as a frequent sensitizer," Allergy, 2018, 73(7), p. 1436-1446.
Freiberger S et al.; "IgG4 but no IgG1 antibody production after intralymphatic immunotherapy with recombinant MAT-Feld1 in human," Allergy, 2016, 71(9), p. 1366-1370.
Graubner C et al.; "Therapie chronisch entzündlicher Atemwegserkrankungen," Pferdespiegel, 2011, 1, p. 2-8.
Hallamaa r et al.; "Treatment of Equine Summer Eczema with an Autogenous Serum Preparation, possibly effected by Inductional Lipid Signals," Deutsche Zeitschrift fur Onkologie, 2001, 33, p. 57-62.
Heydenreich B et al.; "Adjuvant effects of aluminium hydroxide-adsorbed allergens and allergoids—differences in vivo and in vitro," Clin Exp Immunol, 2014, 176(3), p. 310-319.
Hjalmsdottir A et al.; "Dosing intervals in intralymphatic immunotherapy," Allergy, 46, p. 504-507.

Horohov D; "The equine immune responses to infectious and allergic disease: A model for humans?," MolecularImmunology, 2016, 66, p. 89-96.
Jensen-Jarolim E et al.; "Outstanding animal studies in allergy I. From asthma to food allergy and anaphylaxis," Curr Opin Clin Immunol, 2017, 17(3), p. 169-179.
Jensen-Jarolim E et al.; "Outstanding animal studies in allergy II. From atopic barrier and microbiome to allergen-specific immunotherapy," Curr Opin Clin Immunol, 2017, 17(3), p. 180-187.
Jin P et al.; "High-yield novel leech hyaluronidase to expedite the preparation of specific hyaluronan oligomers," Sci Rep, 2004 26(4).
Jonsdottir S et al.;"Developing a preventive immunization approach against insect bite hypersensitivity using recombinant allergens: A pilot study," Veterinary Immunology and Immunopathology, 2016, 166, p. 8-21.
Jonsdottir S et al.;"Developing a preventive immunization approach against insect bite hypersensitivity: Intralymphatic injection with recombinant allergens in Alum or Alum and monophosphoryl lipid A," Veterinary Immunology and Immunopathology, 2016, 172, p. 14-20.
Jonsdottir S et al.; "Oral administration of transgenic barley expressing a Culicoides allergen induces specific antibody response," Equine Veterinary Journal, 2017, 49, p. 512-518.
Kjallman A et al.; "Summer dermatitis on horses—practical treatment guidelines," Finnish Veterinary Days, 2015.
Klier J et al.; "Nanoparticulate CpG Immunotherapy in RAO-Affected Horses: Phase I and IIa Study," Journal of veterinary Internal Medicine, 2015, 5(29), p. 286-293.
Kundig t et al.; "Intralymphatic immunotherapy: Time interval between injections is essential," J Allergy Clin Immunol, 2014, 133(3), p. 930-931.
Lanz s et al.; "Insect Bite Hypersensitivity in Horses is Associated with Airway Hyperreactivity," Journal of veterinary Internal Medicine, 2017,31, p. 1877-1883.
Lehiy C et al.; "The salivary secretome of the biting ,midge, *Culicoides sonorensis*," PeerJ, 2:e426.
Li W et al.; Cross-reactivity, 2015, Allergy Bioinformatics, Translational Bioinformatics 8, Ch.5.
Meulenbroeks C et al.; "Allergen-Specific Cytokine Polarization Protects Shetland Ponies against Culicoides obsoletus-Induced Insect Bite Hypersensitivity," PLOS ONE, 2015, (10(4):e0122090.
Meulenbroeks C et al.; "Recombinant Culicoides obsoletus complex allergens stimulate antigen-specific T cells of insect bite hypersensitive Shetland ponies in vitro," Veterinary Dermatology, 2015, p. 1-11.
Morris R, "Investigating and treating sweet itch—approach and case studies," Veterinary Times, 2014, p. 10-11.
Moya R et al.; "Immunoproteomic characterization of a Dermatophagoides farinae extract used in the treatment of canine atopic dermatitis," Veterinary Immunology and immunopathology, 2016, 180, p. 1-8.
Peng Z et al.; "Mosquito Allergy: Immune Mechanisms and Recombinant Salivary Allergens," Int Arch Allergy Immunol, 2004, 133, p. 198-209.
Rees C, "Response to immunotherapy in six related horses with urticaria secondary to atopy," JAVMA, 2001, 218(5), p. 753-755.
Rendle D, "Managing insect bite hypersensitivity in horses," Livestock, 2014, 19(5), p. 305-308.
Schnabel L et al.; "Equine bone marrow-derived mesenchymal stromal cells are heterogeneous in MHC class II expression and capable of inciting an immune response in vitro," Stem cell Research & Therapy, 2014, 5, p. 1-13.
Shrestha M et al.; "Genome-Wide Association Study of Insect Bite Hypersensitivity in Swedish-Born Icelandic Horses," Journal of Heredity, 2015, p. 366-374.
Scholz F et al.; "First report of angio-oedema subsequent to the administration of allergen specific sublingual immunotherapy for the management of equine hypersensitivity dermatitis," Vet Dermatol, 2016, 27, 439-e115.
Schurink A et al.; "Factors associated with Culicoides Obsoletus complex spp.-specific IgE reactivity in Icelandic horses and Shetland ponies," The Veterinay Journal, 2014, 201(3), p. 395-400.

(56) References Cited

OTHER PUBLICATIONS

Senti G et al.; "A Bizarre Attack on the Freedom of Scientific Expression," Allergy, 2015, 70(9), p. 1037-1038.

Toda M et al.; "Protein unfolding strongly modulates the allergenicity and immunogenicity of Pru p 3, the major peach allergen," J. Allergy Clin Immunol, 2011, 128(5), p. 1022-1030.

Van Hage M et al.; "New vaccines for mammalian allergy using molecular approaches," Frontiers in Immunology, 2014, 5(91), p. 1-5.

Wagner B; "The Immune System of Horses and Other Equids," Encyclpedia of Immunobiology, 2016, vol. 1, p. 549-555.

Wilson A; "Immune responses to ectoparasites of horses, with a focus on insect bite hypersensitivity," Parasite Immunology, 2014, 36, p. 560-572.

Yu A; "Treatment of Equine Allergies," AAEP Resort Symposium, 2015.

Zahradnik E et al.; "Animal allergens and their presence in the environment," Frontiers in Immunology, 2014, 5(76), p. 1-21.

Zaleska A et al.; "Immune regulation by intralymphatic immunotherapy with modular allergen translocation MAT vaccine," Allergy, 2014,69(9),p. 1162-1170.

Zhao J et al.; "Construction of the recombinant vaccine based on T-cell epitope encoding Der p1 and evaluation on its specific immunotherapy efficacy," Int J Clin Med, 2015, 8(4), p. 6436-6443.

Ziegler A et al.; In vitro effects of the toll-like receptor agonists monophosphoryl lipid A and CpG-rich oligonucleotides on cytokine production by equine cells, The Veterinary Journal, 2017, 219, p. 6-11.

Ziegler A et al.; "Longitudinal analysis of allergen-specific IgE and IgG subclasses as potential predictors of insect bite hypersensitivity following first exposure to Culicoides in Icelandic horses," Vet Dermatol, 2018, 29, p. 51-e22.

GenBank Accession No: NM_001099770.1, Tozaki T et al. accessed Mar. 5, 2020.

GenBank Accession No. ADJ67268.1, Schaffartzik A et al.. 2011.

Zhang Hongda, "Study on Novel Gene Transporter Mediated by Cell-penetrating Peptides", Nov. 15, 2008 Chinese Master's Theses Full-text Database (CMFD), Basic Sciences, No. 11.

* cited by examiner

FIG. 1

| Allergome | Uniprot | Uniprot Submitted Name | Uniprot Acc. No. |
|---|---|---|---|
| Cul n 1 | www.uniprot.org/uniprot/Q9BMP6 | Ribosomal P0 protein | Q9BMP6 |
| Cul n 2 | www.uniprot.org/uniprot/B9URL8 | Hyaluronidase | B9URL8 |
|  | www.uniprot.org/uniprot/D9IL12 |  | D9IL12 |
| Cul n 3 | www.uniprot.org/uniprot/D9IL13 | Cul n 3 allergen | D9IL13 |
| Cul n 4 | www.uniprot.org/uniprot/D9IL14 | Cul n 4 allergen | D9IL14 |
|  | www.uniprot.org/uniprot/B9URH7 | Secreted salivary protein | B9URH7 |
| Cul n 5 | www.uniprot.org/uniprot/D9IL15 | Cul n 5 allergen | D9IL15 |
| Cul n 6 | www.uniprot.org/uniprot/D9IL16 | Cul n 6 allergen | D9IL16 |
|  | www.uniprot.org/uniprot/B9URK8 | Secreted salivary protein | B9URK8 |
|  | www.uniprot.org/uniprot/B9URK2 | Secreted salivary protein | B9URK2 |
|  | www.uniprot.org/uniprot/B9URJ2 | Secreted salivary protein | B9URJ2 |
|  | www.uniprot.org/uniprot/B9URH2 | Secreted salivary protein | B9URH2 |
| Cul n 7 | www.uniprot.org/uniprot/D9IL17 | Cul n 7 allergen | D9IL17 |
| Cul n 8 | www.uniprot.org/uniprot/B9URL7 | Maltase | B9URL7 |
|  | www.uniprot.org/uniprot/D9IL18 | Cul n 8 allergen | D9IL18 |
| Cul n 9 | www.uniprot.org/uniprot/B9URI1 | Cul n 9 allergen | B9URI1 |
|  | www.uniprot.org/uniprot/B9URI5 | D7-related salivary protein | B9URI5 |
|  | www.uniprot.org/uniprot/B9URJ9 | D7-related salivary protein | B9URJ9 |
|  | www.uniprot.org/uniprot/B9URK5 | D7-related salivary protein | B9URK5 |
|  | www.uniprot.org/uniprot/B9URK7 | D7-related salivary protein | B9URK7 |
|  | www.uniprot.org/uniprot/B9URL5 | D7-related salivary protein | B9URL5 |
| Cul n 10 | www.uniprot.org/uniprot/D9IL20 | Cul n 10 allergen | D9IL20 |
|  | www.uniprot.org/uniprot/B9URK6 | Secreted salivary protein | B9URK6 |
| Cul n 11 | www.uniprot.org/uniprot/D9IL21 | Cul n 11 allergen | D9IL21 |
|  | www.uniprot.org/uniprot/B9URH8 | Trypsin | B9URH8 |
| Cul n 12 | www.uniprot.org/uniprot/B9URJ1 | Antigen 5-related salivary protein | B9URJ1 |
|  | www.uniprot.org/uniprot/B9URL2 | Antigen 5-related salivary protein | B9URL2 |
| Cul n HSP70 |  |  |  |

| Culicoides obsoletus | | | |
|---|---|---|---|
| Allergome | Uniprot | Uniprot Submitted Name | Uniprot Acc. No. |
| Cul ob 2 | www.uniprot.org/uniprot/M4WGZ3 | Cul o 2 allergen | M4WGZ3 |
| Cul ob 4 | www.uniprot.org/uniprot/M4WGZ8 | Cul o 7 allergen | M4WGZ8 |
| Cul ob 7 | www.uniprot.org/uniprot/M4WK63 | Cul o 5 allergen | M4WK63 |
| Cul ob 8 | www.uniprot.org/uniprot/M4WGA6 | Cul o 1 allergen | M4WGA6 |
| Cul ob 9 | www.uniprot.org/uniprot/M4WGB0 | Cul o 6 allergen | M4WGB0 |
| Cul ob 11 | www.uniprot.org/uniprot/M4WIP7 | Cul o 4 allergen | M4WIP7 |
| Cul ob 12 | www.uniprot.org/uniprot/M4X062 | Cul o 3 allergen | M4X062 |
| - | www.uniprot.org/uniprot/K9P0U1 | Allergen Cul o1 | K9P0U1 |
| - | www.uniprot.org/uniprot/K9P1W5 | Cul o 2 allergen | K9P1W5 |

| Culicoides sonorensis | | | |
|---|---|---|---|
| Allergome | Uniprot | Uniprot Submitted Name | Uniprot Acc. No. |
| Cul so 11 | www.uniprot.org/uniprot/Q66UC8 | Late trypsin | Q66UC8 |
|  | www.uniprot.org/uniprot/Q66UD0 | Late trypsin | Q66UD0 |
| Cul so 12 | www.uniprot.org/uniprot/Q66UE5 | Antigen 5-related protein | Q66UE5 |
| Cul so 4 | www.uniprot.org/uniprot/Q66TZ2 | Putative uncharacterized protein | Q66TZ2 |
|  | www.uniprot.org/uniprot/Q66TZ4 | Putative uncharacterized protein | Q66TZ4 |
| Cul so 6 | www.uniprot.org/uniprot/Q66U95 | Putative secreted salivary protein | Q66U95 |
| Cul so 7 | www.uniprot.org/uniprot/Q66U31 | Putative uncharacterized protein | Q66U31 |
|  | www.uniprot.org/uniprot/Q66U33 | Putative uncharacterized protein | Q66U33 |
| Cul so 8 | www.uniprot.org/uniprot/Q66UC5 | Maltase | Q66UC5 |
| Cul so 9 | www.uniprot.org/uniprot/K9P1W5 | Cul o 2 allergen | K9P1W5 |
|  | www.uniprot.org/uniprot/Q66TY7 | Putative uncharacterized protein | Q66TY7 |
|  | www.uniprot.org/uniprot/Q66TY9 | Putative uncharacterized protein | Q66TY9 |
|  | www.uniprot.org/uniprot/Q66U59 | D7-related protein | Q66U59 |
|  | www.uniprot.org/uniprot/Q66U77 | Putative secreted salivary protein | Q66U77 |
|  | www.uniprot.org/uniprot/Q66UB7 | D7-related protein | Q66UB7 |

FIG. 12

SEQUENCE LISTING

```
<160> NUMBER OF SEQ ID NOS: 23

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Tyr Gly Arg Lys Lys Arg Arg Gln Arg Arg Arg
1               5                   10

<210> SEQ ID NO 2
<211> LENGTH: 208
<212> TYPE: PRT
<213> ORGANISM: Equus caballus
```

<400> SEQUENCE: 2

```
Met Glu Asp Gln Arg Asp Leu Ile Ser Asn His Glu Gln Val Pro Ile
1               5                   10                  15

Leu Gly Gln Arg Pro Ala Ala Pro Glu Arg Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Phe Gln Gln Gln Gly Arg Leu Asp Lys
    50                  55                  60

Leu Thr Val Thr Ala Gln Asn Leu Gln Leu Glu Lys Leu Arg Met Lys
65                  70                  75                  80

Leu Pro Lys Ser Ala Lys Pro Val Ser Lys Ile Arg Val Ala Thr Pro
                85                  90                  95

Met Leu Met Gln Ala Leu Pro Met Glu Gly Leu Ser His Gly Pro Met
            100                 105                 110

Gln Asn Ala Thr Lys Tyr Gly Asn Thr Thr Gln Asp His Val Met His
        115                 120                 125

Leu Leu Leu Arg Ala Asp Pro Leu Lys Val Tyr Pro Gln Leu Lys Gly
    130                 135                 140

Ser Phe Gln Glu Asn Leu Lys His Leu Lys Ser Thr Met Asp Gly Leu
145                 150                 155                 160

Asp Trp Lys Val Phe Glu Asn Trp Met His Gln Trp Leu Leu Phe Glu
                165                 170                 175

Met Ser Arg Asn Ser Leu Glu Glu Lys Pro Thr Gln Gly Pro Thr Lys
            180                 185                 190

Glu Pro Leu Glu Ile Glu Asp Leu Ser Ser Gly Val Gly Met Ala Lys
        195                 200                 205
```

<210> SEQ ID NO 3
<211> LENGTH: 152
<212> TYPE: PRT
<213> ORGANISM: Artificial Sequence
<220> FEATURE:
<223> OTHER INFORMATION: Culicoides spec

<400> SEQUENCE: 3

```
Met Lys Phe Pro Thr Phe Leu Ile Leu Ala Phe Phe Leu Ser Leu Tyr
1               5                   10                  15

Ile Ser Ser Thr Ala Ser Arg Arg Lys His Phe Arg His Leu Lys Arg
            20                  25                  30

Ile Glu Ala Ala Asn Asp Cys Pro Ala Lys Asn Ser Gly Thr Tyr Gln
        35                  40                  45

Lys Val Cys Lys Gln Leu Gln Lys Tyr Tyr Val Leu Thr Pro Asp Asp
    50                  55                  60

Lys Leu Gly Ser Tyr Leu Lys Gly Gly Leu Gln Glu Ala Ala Asn Arg
65                  70                  75                  80

Val Leu Thr Pro Val Ser Lys Ser Asp Lys Ile Thr Phe Asp Ile Val
                85                  90                  95

Gln Asn Cys Leu Lys Asn Phe Gln Val Met Val Asn Lys His Asn Lys
            100                 105                 110

Glu Ala Leu Arg Lys Tyr Arg Glu Cys Lys Lys Glu Cys Phe Thr Glu
        115                 120                 125

Val Gly Lys Glu Phe Ser Ser Ala Leu Asp Lys Thr Gly Val Gln Ile
    130                 135                 140
```

```
Ala Glu Cys Leu Asn Glu Ser Leu
145                 150

<210> SEQ ID NO 4
<211> LENGTH: 205
<212> TYPE: PRT
<213> ORGANISM: Artificial Sequence
<220> FEATURE:
<223> OTHER INFORMATION: Culicoides spec.

<400> SEQUENCE: 4

Met Arg Phe Ala Thr Ile Phe Leu Leu Ser Ala Ser Ile Ile Leu Leu
1               5                   10                  15

Ser Thr Gly Glu Ala Leu Ala Lys Lys Lys Lys Lys Ile Asp Lys Ser
            20                  25                  30

Met Pro Pro Glu Cys Leu Pro Leu Pro Pro Lys Lys Arg Ala Ser Glu
        35                  40                  45

Cys Thr Asn Gln Ser Gly Phe Lys Tyr Tyr Pro Lys Thr Asn Gln Cys
    50                  55                  60

Gly Pro Val Arg Asn Gln Leu Cys Gln Gly His Gly Gly Phe Thr Thr
65                  70                  75                  80

Leu Asp Glu Cys Val Tyr Lys Cys Tyr Asp Tyr Arg Lys Met Ser Thr
                85                  90                  95

Thr Lys Asn Val Asp Gly Cys Asn Lys Ser Ile Lys Glu Glu Glu Met
            100                 105                 110

Thr Glu Ala Ile Arg Val Val Ser Arg Gly Asp Ser Pro Asp Leu Ile
        115                 120                 125

Lys Asp Asn Arg Cys Arg Glu Pro Asn Glu Leu Ser Leu Lys Asn Gly
    130                 135                 140

Ser Ala Arg Val Lys Pro Ala Tyr Lys Phe Asn Lys Asp Thr Asn Glu
145                 150                 155                 160

Cys Val Ala Met Met Asp Lys Val Cys Leu Gly Arg Asn Arg Phe Lys
                165                 170                 175

Thr Lys Glu Glu Cys Val His Val Cys Asn Trp Asn Leu Ser Ser Gly
            180                 185                 190

Arg His Arg His Ile Val Arg Glu Ser Asn Ala Lys Gln
        195                 200                 205

<210> SEQ ID NO 5
<211> LENGTH: 388
<212> TYPE: PRT
<213> ORGANISM: Artificial Sequence
<220> FEATURE:
<223> OTHER INFORMATION: Culicoides spec.

<400> SEQUENCE: 5

Met Trp Ser Ser Val Val Asn Ile Ser His Ile Met Ala Val Val Thr
1               5                   10                  15

Thr Ala His Leu Ile Ser Ala Gln His Leu Ile Gln Ala Glu Leu Pro
            20                  25                  30

Asp Ser Pro Leu Asn Ile Val Lys Glu Phe Asp Asp Asp Gly Arg Asn
        35                  40                  45

Asn Asn Asn Gln Asn Asp Phe Asn Phe Tyr Trp Asn Ile Pro Ser Phe
    50                  55                  60

Met Cys Ala Gln His Asn Ile Thr Phe Thr Asp Met Thr Ser Ser Tyr
65                  70                  75                  80

Asn Ile Val Gln Asn Lys Asp Asp Lys Trp Arg Gly Asp Lys Ile Val
                85                  90                  95
```

```
Ile Leu Tyr Asp Pro Gly Lys Phe Pro Ala Leu Leu Glu His Gln Gly
            100                 105                 110

Gln Leu Tyr Arg Arg Asn Gly Val Pro Gln Glu Gly Asn Leu Gln
        115                 120                 125

Glu His Ile Asp Ile Leu Ala Glu His Ile Asn Lys Leu Ile Pro Asp
        130                 135                 140

Thr Gln Phe Ser Gly Ile Gly Val Ile Asp Phe Glu Ser Trp Arg Pro
145                 150                 155                 160

Ile Phe Arg Gln Asn Ser Gly Val Leu Gln Pro Tyr Lys Asp Leu Ser
                165                 170                 175

Tyr Lys Leu Val His Arg Asp His Lys Leu Trp Asn Arg Lys Arg Val
            180                 185                 190

Glu Ile Glu Ala Ala Arg Leu Phe Glu Ala Ala Gly Arg Thr Phe Val
        195                 200                 205

Glu Glu Thr Ile Asn Val Ala Lys Ile Leu Arg Pro Lys Ala Lys Trp
210                 215                 220

Gly Tyr Tyr Gly Phe Pro Tyr Cys Phe Asn Met Asn Gly Gly Ala Asn
225                 230                 235                 240

Met Asn Glu Asp Cys Pro Ala Asn Val Lys Glu Glu Asn Asp Gln Ile
                245                 250                 255

Lys Trp Leu Trp Asp Ile Val Asp Val Leu Pro Ser Val Tyr Leu
            260                 265                 270

Asn Asn Lys Ile Thr Ser Ala Gln Arg Val Gln Phe Val Arg Gly Arg
            275                 280                 285

Met Arg Glu Gly Tyr Arg Val Ala Lys Met Ser Lys Lys Ser Pro Lys
        290                 295                 300

Pro Pro Val Leu Ala Tyr Leu Arg Tyr Val Tyr Thr Asp Thr Leu Lys
305                 310                 315                 320

Phe Leu Ser Asn Glu Asp Leu Lys Gln Ala Ile Lys Val Ser Lys Glu
                325                 330                 335

Gln Lys Ser Lys Gly Met Ile Phe Trp Gly Ser Ser Tyr Asp Val Lys
            340                 345                 350

Thr Lys Glu Gln Cys Ile Asp Phe Arg Lys Tyr Val Asp Asn Asn Leu
        355                 360                 365

Gly Pro Ile Val Leu Leu Ala Asn Asn Lys Ser Pro Lys Val Leu Thr
370                 375                 380

Pro Asn Leu Ala
385

<210> SEQ ID NO 6
<211> LENGTH: 261
<212> TYPE: PRT
<213> ORGANISM: Artificial Sequence
<220> FEATURE:
<223> OTHER INFORMATION: Culicoides spec.

<400> SEQUENCE: 6

Met Phe Arg Ile Cys Leu Phe Thr Val Leu Cys Val Asn Phe Val Val
1               5                   10                  15

Ala Thr Asp Phe Cys Asp Arg Lys Leu Cys Arg Arg Gln Ile Glu Pro
            20                  25                  30

Asn Val Tyr Gln Asn Ile Pro His Ile Gly Cys Asn His Asp Gly Arg
        35                  40                  45

Asn Ser Pro Ala Cys Pro Ser Asp Ala Lys Ile Leu Pro Met Ser Thr
    50                  55                  60
```

-continued

```
Lys Arg Lys Asn Leu Ile Leu Arg Val His Asn Arg Leu Arg Asn Lys
 65                  70                  75                  80

Val Ala Leu Gly Gln Leu Pro Gly Tyr Pro Lys Ala Val Arg Met Pro
                 85                  90                  95

Ile Leu Arg Trp Asp Asp Glu Leu Ala Tyr Leu Ala Glu Leu Asn Val
            100                 105                 110

Lys Gln Cys Glu Met Lys His Asp Gln Cys Arg Asn Thr Asp Lys Phe
        115                 120                 125

Arg Tyr Ala Gly Gln Asn Leu Ala Tyr Ile Gly Gly Lys Glu Pro
    130                 135                 140

Asn Ala Val Arg Ile Lys Thr Leu Val Arg Ala Trp Phe Asp Glu Tyr
145                 150                 155                 160

Lys Asp Ala Asn Ser Ser Phe Ile Asp Lys Tyr Arg Ser His Pro Asn
                165                 170                 175

Gly Lys Ala Ile Gly His Phe Thr Ala Met Val Gln Asp Arg Thr Asp
            180                 185                 190

Thr Val Gly Cys Ala Ile Leu Arg His Thr Lys Asn Thr Tyr Phe Phe
        195                 200                 205

Leu Ala Cys Asn Tyr Ser Phe Thr Asn Met Val Lys Asp Lys Val Tyr
    210                 215                 220

Thr Arg Gly Ala Lys Ser Cys Ser Lys Cys Arg Thr Gly Cys Ser Pro
225                 230                 235                 240

Val Tyr Lys Gly Leu Cys Lys Pro His Glu Tyr Val Asn Pro Asp Pro
                245                 250                 255

Asp Glu Asp Leu Asp
            260

<210> SEQ ID NO 7
<211> LENGTH: 258
<212> TYPE: PRT
<213> ORGANISM: Artificial Sequence
<220> FEATURE:
<223> OTHER INFORMATION: Synthetic Peptide

<400> SEQUENCE: 7

Met His His His His His Tyr Gly Arg Lys Lys Arg Arg Gln Arg
  1               5                  10                  15

Arg Arg Met Glu Asp Gln Arg Asp Leu Ile Ser Asn His Glu Gln Val
                 20                  25                  30

Pro Ile Leu Gly Gln Arg Pro Ala Ala Pro Glu Arg Lys Ser Ser Arg
             35                  40                  45

Gly Ala Leu Tyr Thr Gly Phe Ser Val Leu Val Ala Leu Leu Leu Ala
         50                  55                  60

Gly Gln Ala Thr Thr Ala Tyr Phe Leu Phe Gln Gln Gly Arg Leu
 65                  70                  75                  80

Asp Lys Leu Thr Val Thr Ala Gln Asn Leu Gln Leu Glu Lys Leu Arg
                 85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
        115                 120                 125

Arg Arg Lys His Phe Arg His Leu Lys Arg Ile Glu Ala Ala Asn Asp
    130                 135                 140

Ser Pro Ala Lys Asn Ser Gly Thr Tyr Gln Lys Val Ser Lys Gln Leu
145                 150                 155                 160
```

```
Gln Lys Tyr Tyr Val Leu Thr Pro Asp Asp Lys Leu Gly Ser Tyr Leu
                165                 170                 175

Lys Gly Gly Leu Gln Glu Ala Ala Asn Arg Val Leu Thr Pro Val Ser
            180                 185                 190

Lys Ser Asp Lys Ile Thr Phe Asp Ile Val Gln Asn Ser Leu Lys Asn
        195                 200                 205

Phe Gln Val Met Val Asn Lys His Asn Lys Glu Ala Leu Arg Lys Tyr
    210                 215                 220

Arg Glu Ser Lys Lys Glu Ser Phe Thr Glu Val Gly Lys Glu Phe Ser
225                 230                 235                 240

Ser Ala Leu Asp Lys Thr Gly Val Gln Ile Ala Glu Ser Leu Asn Glu
                245                 250                 255

Ser Leu

<210> SEQ ID NO 8
<211> LENGTH: 258
<212> TYPE: PRT
<213> ORGANISM: Artificial Sequence
<220> FEATURE:
<223> OTHER INFORMATION: Synthetic Peptide

<400> SEQUENCE: 8

Met Tyr Gly Arg Lys Lys Arg Gln Arg Arg Met Glu Asp Gln
1               5                   10                  15

Arg Asp Leu Ile Ser Asn His Glu Gln Val Pro Ile Leu Gly Gln Arg
            20                  25                  30

Pro Ala Ala Pro Glu Arg Lys Ser Ser Arg Gly Ala Leu Tyr Thr Gly
        35                  40                  45

Phe Ser Val Leu Val Ala Leu Leu Leu Ala Gly Gln Ala Thr Thr Ala
    50                  55                  60

Tyr Phe Leu Phe Gln Gln Gln Gly Arg Leu Asp Lys Leu Thr Val Thr
65                  70                  75                  80

Ala Gln Asn Leu Gln Leu Glu Lys Leu Arg Met Lys Leu Pro Lys Ser
                85                  90                  95

Ala Lys Pro Val Ser Lys Ile Arg Val Ala Thr Pro Met Leu Met Gln
            100                 105                 110

Ala Leu Pro Met Glu Gly Leu Ser His Gly Arg Arg Lys His Phe Arg
        115                 120                 125

His Leu Lys Arg Ile Glu Ala Ala Asn Asp Ser Pro Ala Lys Asn Ser
130                 135                 140

Gly Thr Tyr Gln Lys Val Ser Lys Gln Leu Gln Lys Tyr Tyr Val Leu
145                 150                 155                 160

Thr Pro Asp Asp Lys Leu Gly Ser Tyr Leu Lys Gly Gly Leu Gln Glu
                165                 170                 175

Ala Ala Asn Arg Val Leu Thr Pro Val Ser Lys Ser Asp Lys Ile Thr
            180                 185                 190

Phe Asp Ile Val Gln Asn Ser Leu Lys Asn Phe Gln Val Met Val Asn
        195                 200                 205

Lys His Asn Lys Glu Ala Leu Arg Lys Tyr Arg Glu Ser Lys Lys Glu
    210                 215                 220

Ser Phe Thr Glu Val Gly Lys Glu Phe Ser Ser Ala Leu Asp Lys Thr
225                 230                 235                 240

Gly Val Gln Ile Ala Glu Ser Leu Asn Glu Ser Leu His His His
                245                 250                 255
```

His His

<210> SEQ ID NO 9
<211> LENGTH: 310
<212> TYPE: PRT
<213> ORGANISM: Artificial Sequence
<220> FEATURE:
<223> OTHER INFORMATION: Synthetic Peptide

<400> SEQUENCE: 9

```
Met His His His His His Tyr Gly Arg Lys Lys Arg Arg Gln Arg
1               5                   10                  15

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
            35                  40                  45

Gly Ala Leu Tyr Thr Gly Phe Ser Val Leu Val Ala Leu Leu Leu Ala
 50                  55                  60

Gly Gln Ala Thr Thr Ala Tyr Phe Leu Phe Gln Gln Gln Gly Arg Leu
 65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
            115                 120                 125

Lys Lys Lys Lys Lys Ile Asp Lys Ser Met Pro Pro Glu Ser Leu Pro
130                 135                 140

Leu Pro Pro Lys Lys Arg Ala Ser Glu Ser Thr Asn Gln Ser Gly Phe
145                 150                 155                 160

Lys Tyr Tyr Pro Lys Thr Asn Gln Ser Gly Pro Val Arg Asn Gln Leu
                165                 170                 175

Ser Gln Gly His Gly Gly Phe Thr Thr Leu Asp Glu Ser Val Tyr Lys
            180                 185                 190

Ser Tyr Asp Tyr Arg Lys Met Ser Thr Thr Lys Asn Val Asp Gly Ser
            195                 200                 205

Asn Lys Ser Ile Lys Glu Glu Glu Met Thr Glu Ala Ile Arg Val Val
210                 215                 220

Ser Arg Gly Asp Ser Pro Asp Leu Ile Lys Asp Asn Arg Ser Arg Glu
225                 230                 235                 240

Pro Asn Glu Leu Ser Leu Lys Asn Gly Ser Ala Arg Val Lys Pro Ala
                245                 250                 255

Tyr Lys Phe Asn Lys Asp Thr Asn Glu Ser Val Ala Met Met Asp Lys
            260                 265                 270

Val Ser Leu Gly Arg Asn Arg Phe Lys Thr Lys Glu Glu Ser Val His
            275                 280                 285

Val Ser Asn Trp Asn Leu Ser Ser Gly Arg His Arg His Ile Val Arg
            290                 295                 300

Glu Ser Asn Ala Lys Gln
305                 310
```

<210> SEQ ID NO 10
<211> LENGTH: 310
<212> TYPE: PRT
<213> ORGANISM: Artificial Sequence
<220> FEATURE:
<223> OTHER INFORMATION: Synthetic Peptide

```
<400> SEQUENCE: 10

Met Tyr Gly Arg Lys Lys Arg Gln Arg Arg Met Glu Asp Gln
1               5                   10                  15

Arg Asp Leu Ile Ser Asn His Glu Gln Val Pro Ile Leu Gly Gln Arg
            20                  25                  30

Pro Ala Ala Pro Glu Arg Lys Ser Ser Arg Gly Ala Leu Tyr Thr Gly
        35                  40                  45

Phe Ser Val Leu Val Ala Leu Leu Ala Gly Gln Ala Thr Thr Ala
50                  55                  60

Tyr Phe Leu Phe Gln Gln Gln Gly Arg Leu Asp Lys Leu Thr Val Thr
65                  70                  75                  80

Ala Gln Asn Leu Gln Leu Glu Lys Leu Arg Met Lys Leu Pro Lys Ser
                85                  90                  95

Ala Lys Pro Val Ser Lys Ile Arg Val Ala Thr Pro Met Leu Met Gln
            100                 105                 110

Ala Leu Pro Met Glu Gly Leu Ser His Gly Lys Lys Lys Lys Ile
        115                 120                 125

Asp Lys Ser Met Pro Pro Glu Ser Leu Pro Leu Pro Pro Lys Lys Arg
130                 135                 140

Ala Ser Glu Ser Thr Asn Gln Ser Gly Phe Lys Tyr Tyr Pro Lys Thr
145                 150                 155                 160

Asn Gln Ser Gly Pro Val Arg Asn Gln Leu Ser Gln Gly His Gly Gly
                165                 170                 175

Phe Thr Thr Leu Asp Glu Ser Val Tyr Lys Ser Tyr Asp Tyr Arg Lys
            180                 185                 190

Met Ser Thr Thr Lys Asn Val Asp Gly Ser Asn Lys Ser Ile Lys Glu
        195                 200                 205

Glu Glu Met Thr Glu Ala Ile Arg Val Val Ser Arg Gly Asp Ser Pro
210                 215                 220

Asp Leu Ile Lys Asp Asn Arg Ser Arg Glu Pro Asn Glu Leu Ser Leu
225                 230                 235                 240

Lys Asn Gly Ser Ala Arg Val Lys Pro Ala Tyr Lys Phe Asn Lys Asp
                245                 250                 255

Thr Asn Glu Ser Val Ala Met Met Asp Lys Val Ser Leu Gly Arg Asn
            260                 265                 270

Arg Phe Lys Thr Lys Glu Glu Ser Val His Val Ser Asn Trp Asn Leu
        275                 280                 285

Ser Ser Gly Arg His Arg His Ile Val Arg Glu Ser Asn Ala Lys Gln
    290                 295                 300

His His His His His His
305                 310

<210> SEQ ID NO 11
<211> LENGTH: 493
<212> TYPE: PRT
<213> ORGANISM: Artificial Sequence
<220> FEATURE:
<223> OTHER INFORMATION: Synthetic Peptide

<400> SEQUENCE: 11

Met His His His His His His Tyr Gly Arg Lys Lys Arg Gln Arg
1               5                   10                  15

Arg Arg Met Glu Asp Gln Arg Asp Leu Ile Ser Asn His Glu Gln Val
            20                  25                  30
```

```
Pro Ile Leu Gly Gln Arg Pro Ala Pro Glu Arg Lys Ser Ser Arg
         35                  40                  45
Gly Ala Leu Tyr Thr Gly Phe Ser Val Leu Val Ala Leu Leu Ala
 50                  55                  60
Gly Gln Ala Thr Thr Ala Tyr Phe Leu Phe Gln Gln Gln Gly Arg Leu
 65                  70                  75                  80
Asp Lys Leu Thr Val Thr Ala Gln Asn Leu Gln Leu Glu Lys Leu Arg
                 85                  90                  95
Met Lys Leu Pro Lys Ser Ala Lys Pro Val Ser Lys Ile Arg Val Ala
                100                 105                 110
Thr Pro Met Leu Met Gln Ala Leu Pro Met Glu Gly Leu Ser His Gly
                115                 120                 125
Gln His Leu Ile Gln Ala Glu Leu Pro Asp Ser Pro Leu Asn Ile Val
        130                 135                 140
Lys Glu Phe Asp Asp Asp Gly Arg Asn Asn Asn Gln Asn Asp Phe
145                 150                 155                 160
Asn Phe Tyr Trp Asn Ile Pro Ser Phe Met Ser Ala Gln His Asn Ile
                165                 170                 175
Thr Phe Thr Asp Met Thr Ser Ser Tyr Asn Ile Val Gln Asn Lys Asp
                180                 185                 190
Asp Lys Trp Arg Gly Asp Lys Ile Val Ile Leu Tyr Asp Pro Gly Lys
        195                 200                 205
Phe Pro Ala Leu Leu Glu His Gln Gly Gln Leu Tyr Arg Arg Asn Gly
210                 215                 220
Gly Val Pro Gln Glu Gly Asn Leu Gln Glu His Ile Asp Ile Leu Ala
225                 230                 235                 240
Glu His Ile Asn Lys Leu Ile Pro Asp Thr Gln Phe Ser Gly Ile Gly
                245                 250                 255
Val Ile Asp Phe Glu Ser Trp Arg Pro Ile Phe Arg Gln Asn Ser Gly
                260                 265                 270
Val Leu Gln Pro Tyr Lys Asp Leu Ser Tyr Lys Leu Val His Arg Asp
        275                 280                 285
His Lys Leu Trp Asn Arg Lys Arg Val Glu Ile Glu Ala Ala Arg Leu
        290                 295                 300
Phe Glu Ala Ala Gly Arg Thr Phe Val Glu Glu Thr Ile Asn Val Ala
305                 310                 315                 320
Lys Ile Leu Arg Pro Lys Ala Lys Trp Gly Tyr Tyr Gly Phe Pro Tyr
                325                 330                 335
Ser Phe Asn Met Asn Gly Gly Ala Asn Met Asn Glu Asp Ser Pro Ala
                340                 345                 350
Asn Val Lys Glu Glu Asn Asp Gln Ile Lys Trp Leu Trp Asp Ile Val
                355                 360                 365
Asp Val Val Leu Pro Ser Val Tyr Leu Asn Asn Lys Ile Thr Ser Ala
        370                 375                 380
Gln Arg Val Gln Phe Val Arg Gly Arg Met Arg Glu Gly Tyr Arg Val
385                 390                 395                 400
Ala Lys Met Ser Lys Lys Ser Pro Lys Pro Pro Val Leu Ala Tyr Leu
                405                 410                 415
Arg Tyr Val Tyr Thr Asp Thr Leu Lys Phe Leu Ser Asn Glu Asp Leu
                420                 425                 430
Lys Gln Ala Ile Lys Val Ser Lys Glu Gln Lys Ser Lys Gly Met Ile
        435                 440                 445
Phe Trp Gly Ser Ser Tyr Asp Val Lys Thr Lys Glu Gln Ser Ile Asp
```

```
            450                 455                 460
Phe Arg Lys Tyr Val Asp Asn Leu Gly Pro Ile Val Leu Leu Ala
465                 470                 475                 480

Asn Asn Lys Ser Pro Lys Val Leu Thr Pro Asn Leu Ala
                485                 490

<210> SEQ ID NO 12
<211> LENGTH: 493
<212> TYPE: PRT
<213> ORGANISM: Artificial Sequence
<220> FEATURE:
<223> OTHER INFORMATION: Synthetic Peptide

<400> SEQUENCE: 12

Met Tyr Gly Arg Lys Lys Arg Gln Arg Arg Met Glu Asp Gln
1               5                   10                  15

Arg Asp Leu Ile Ser Asn His Glu Gln Val Pro Ile Leu Gly Gln Arg
                20                  25                  30

Pro Ala Ala Pro Glu Arg Lys Ser Ser Arg Gly Ala Leu Tyr Thr Gly
            35                  40                  45

Phe Ser Val Leu Val Ala Leu Leu Ala Gly Gln Ala Thr Thr Ala
50                  55                  60

Tyr Phe Leu Phe Gln Gln Gly Arg Leu Asp Lys Leu Thr Val Thr
65                  70                  75                  80

Ala Gln Asn Leu Gln Leu Glu Lys Leu Arg Met Lys Leu Pro Lys Ser
                85                  90                  95

Ala Lys Pro Val Ser Lys Ile Arg Val Ala Thr Pro Met Leu Met Gln
            100                 105                 110

Ala Leu Pro Met Glu Gly Leu Ser His Gly Gln His Leu Ile Gln Ala
        115                 120                 125

Glu Leu Pro Asp Ser Pro Leu Asn Ile Val Lys Glu Phe Asp Asp Asp
130                 135                 140

Gly Arg Asn Asn Asn Gln Asn Asp Phe Asn Phe Tyr Trp Asn Ile
145                 150                 155                 160

Pro Ser Phe Met Ser Ala Gln His Asn Ile Thr Phe Thr Asp Met Thr
                165                 170                 175

Ser Ser Tyr Asn Ile Val Gln Asn Lys Asp Asp Lys Trp Arg Gly Asp
            180                 185                 190

Lys Ile Val Ile Leu Tyr Asp Pro Gly Lys Phe Pro Ala Leu Leu Glu
        195                 200                 205

His Gln Gly Gln Leu Tyr Arg Arg Asn Gly Val Pro Gln Glu Gly
210                 215                 220

Asn Leu Gln Glu His Ile Asp Ile Leu Ala Glu His Ile Asn Lys Leu
225                 230                 235                 240

Ile Pro Asp Thr Gln Phe Ser Gly Ile Gly Val Ile Asp Phe Glu Ser
                245                 250                 255

Trp Arg Pro Ile Phe Arg Gln Asn Ser Gly Val Leu Gln Pro Tyr Lys
            260                 265                 270

Asp Leu Ser Tyr Lys Leu Val His Arg Asp His Lys Leu Trp Asn Arg
        275                 280                 285

Lys Arg Val Glu Ile Glu Ala Ala Arg Leu Phe Glu Ala Ala Gly Arg
    290                 295                 300

Thr Phe Val Glu Glu Thr Ile Asn Val Ala Lys Ile Leu Arg Pro Lys
305                 310                 315                 320

Ala Lys Trp Gly Tyr Tyr Gly Phe Pro Tyr Ser Phe Asn Met Asn Gly
```

```
                      325                 330                 335
Gly Ala Asn Met Asn Glu Asp Ser Pro Ala Asn Val Lys Glu Glu Asn
                340                 345                 350

Asp Gln Ile Lys Trp Leu Trp Asp Ile Val Asp Val Leu Pro Ser
            355                 360                 365

Val Tyr Leu Asn Asn Lys Ile Thr Ser Ala Gln Arg Val Gln Phe Val
370                 375                 380

Arg Gly Arg Met Arg Glu Gly Tyr Arg Val Ala Lys Met Ser Lys Lys
385                 390                 395                 400

Ser Pro Lys Pro Val Leu Ala Tyr Leu Arg Tyr Val Tyr Thr Asp
            405                 410                 415

Thr Leu Lys Phe Leu Ser Asn Glu Asp Leu Lys Gln Ala Ile Lys Val
                420                 425                 430

Ser Lys Glu Gln Lys Ser Lys Gly Met Ile Phe Trp Gly Ser Ser Tyr
            435                 440                 445

Asp Val Lys Thr Lys Glu Gln Ser Ile Asp Phe Arg Lys Tyr Val Asp
            450                 455                 460

Asn Asn Leu Gly Pro Ile Val Leu Leu Ala Asn Asn Lys Ser Pro Lys
465                 470                 475                 480

Val Leu Thr Pro Asn Leu Ala His His His His His His
                485                 490

<210> SEQ ID NO 13
<211> LENGTH: 372
<212> TYPE: PRT
<213> ORGANISM: Artificial Sequence
<220> FEATURE:
<223> OTHER INFORMATION: Synthetic Peptide

<400> SEQUENCE: 13

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Phe Gln Gln Gln Gly Arg Leu
65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
        115                 120                 125

Thr Asp Phe Ser Asp Arg Lys Leu Ser Arg Arg Gln Ile Glu Pro Asn
    130                 135                 140

Val Tyr Gln Asn Ile Pro His Ile Gly Ser Asn His Asp Gly Arg Asn
145                 150                 155                 160

Ser Pro Ala Ser Pro Ser Asp Ala Lys Ile Leu Pro Met Ser Thr Lys
                165                 170                 175

Arg Lys Asn Leu Ile Leu Arg Val His Asn Arg Leu Arg Asn Lys Val
            180                 185                 190

Ala Leu Gly Gln Leu Pro Gly Tyr Pro Lys Ala Val Arg Met Pro Ile
```

```
                195                 200                 205
Leu Arg Trp Asp Asp Glu Leu Ala Tyr Leu Ala Glu Leu Asn Val Lys
210                 215                 220

Gln Ser Glu Met Lys His Asp Gln Ser Arg Asn Thr Asp Lys Phe Arg
225                 230                 235                 240

Tyr Ala Gly Gln Asn Leu Ala Tyr Ile Gly Gly Lys Glu Pro Asn
                245                 250                 255

Ala Val Arg Ile Lys Thr Leu Val Arg Ala Trp Phe Asp Glu Tyr Lys
                260                 265                 270

Asp Ala Asn Ser Ser Phe Ile Asp Lys Tyr Arg Ser His Pro Asn Gly
                275                 280                 285

Lys Ala Ile Gly His Phe Thr Ala Met Val Gln Asp Arg Thr Asp Thr
290                 295                 300

Val Gly Ile Ala Ile Leu Arg His Thr Lys Asn Thr Tyr Phe Phe Leu
305                 310                 315                 320

Ala Ile Asn Tyr Ser Phe Thr Asn Met Val Lys Asp Lys Val Tyr Thr
                325                 330                 335

Arg Gly Ala Lys Ser Ser Ser Lys Ser Arg Thr Gly Ser Ser Pro Val
                340                 345                 350

Tyr Lys Gly Leu Ser Lys Pro His Glu Tyr Val Asn Pro Asp Pro Asp
                355                 360                 365

Glu Asp Leu Asp
    370

<210> SEQ ID NO 14
<211> LENGTH: 372
<212> TYPE: PRT
<213> ORGANISM: Artificial Sequence
<220> FEATURE:
<223> OTHER INFORMATION: Synthetic Peptide

<400> SEQUENCE: 14

Met Tyr Gly Arg Lys Lys Arg Arg Gln Arg Arg Met Glu Asp Gln
1               5                   10                  15

Arg Asp Leu Ile Ser Asn His Glu Gln Val Pro Ile Leu Gly Gln Arg
                20                  25                  30

Pro Ala Ala Pro Glu Arg Lys Ser Ser Arg Gly Ala Leu Tyr Thr Gly
                35                  40                  45

Phe Ser Val Leu Val Ala Leu Leu Leu Ala Gly Gln Ala Thr Thr Ala
            50                  55                  60

Tyr Phe Leu Phe Gln Gln Gln Gly Arg Leu Asp Lys Leu Thr Val Thr
65                  70                  75                  80

Ala Gln Asn Leu Gln Leu Glu Lys Leu Arg Met Lys Leu Pro Lys Ser
                85                  90                  95

Ala Lys Pro Val Ser Lys Ile Arg Val Ala Thr Pro Met Leu Met Gln
                100                 105                 110

Ala Leu Pro Met Glu Gly Leu Ser His Gly Thr Asp Phe Ser Asp Arg
            115                 120                 125

Lys Leu Ser Arg Arg Gln Ile Glu Pro Asn Val Tyr Gln Asn Ile Pro
130                 135                 140

His Ile Gly Ser Asn His Asp Gly Arg Asn Ser Pro Ala Ser Pro Ser
145                 150                 155                 160

Asp Ala Lys Ile Leu Pro Met Ser Thr Lys Arg Lys Asn Leu Ile Leu
                165                 170                 175

Arg Val His Asn Arg Leu Arg Asn Lys Val Ala Leu Gly Gln Leu Pro
```

```
                180             185             190
Gly Tyr Pro Lys Ala Val Arg Met Pro Ile Leu Arg Trp Asp Asp Glu
            195                 200                 205

Leu Ala Tyr Leu Ala Glu Leu Asn Val Lys Gln Ser Glu Met Lys His
            210                 215                 220

Asp Gln Ser Arg Asn Thr Asp Lys Phe Arg Tyr Ala Gly Gln Asn Leu
225                 230                 235                 240

Ala Tyr Ile Gly Gly Lys Glu Pro Asn Ala Val Arg Ile Lys Thr
                245                 250                 255

Leu Val Arg Ala Trp Phe Asp Glu Tyr Lys Asp Ala Asn Ser Ser Phe
            260                 265                 270

Ile Asp Lys Tyr Arg Ser His Pro Asn Gly Lys Ala Ile Gly His Phe
            275                 280                 285

Thr Ala Met Val Gln Asp Arg Thr Asp Thr Val Gly Ile Ala Ile Leu
            290                 295                 300

Arg His Thr Lys Asn Thr Tyr Phe Phe Leu Ala Ile Asn Tyr Ser Phe
305                 310                 315                 320

Thr Asn Met Val Lys Asp Lys Val Tyr Thr Arg Gly Ala Lys Ser Ser
                325                 330                 335

Ser Lys Ser Arg Thr Gly Ser Ser Pro Val Tyr Lys Gly Leu Ser Lys
                340                 345                 350

Pro His Glu Tyr Val Asn Pro Asp Pro Glu Asp Leu Asp His His
                355                 360                 365

His His His His
        370

<210> SEQ ID NO 15
<211> LENGTH: 110
<212> TYPE: PRT
<213> ORGANISM: Equus caballus

<400> SEQUENCE: 15

Met Glu Asp Gln Arg Asp Leu Ile Ser Asn His Glu Gln Val Pro Ile
1               5                   10                  15

Leu Gly Gln Arg Pro Ala Ala Pro Glu Arg Lys Cys Ser Arg Gly Ala
                20                  25                  30

Leu Tyr Thr Gly Phe Ser Val Leu Val Ala Leu Leu Leu Ala Gly Gln
            35                  40                  45

Ala Thr Thr Ala Tyr Phe Leu Phe Gln Gln Gln Gly Arg Leu Asp Lys
    50                  55                  60

Leu Thr Val Thr Ala Gln Asn Leu Gln Leu Glu Lys Leu Arg Met Lys
65                  70                  75                  80

Leu Pro Lys Ser Ala Lys Pro Val Ser Lys Ile Arg Val Ala Thr Pro
                85                  90                  95

Met Leu Met Gln Ala Leu Pro Met Glu Gly Leu Ser His Gly
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 16

Met Glu Asp Gln Arg Asp Leu Ile Ser Asn His Glu Gln Val Pro Ile
1               5                   10                  15
```

Leu Gly Gln Arg Pro Ala Ala Pro Glu Arg Lys Ser Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Phe Gln Gln Gly Arg Leu Asp Lys
50                      55                  60

Leu Thr Val Thr Ala Gln Asn Leu Gln Leu Glu Lys Leu Arg Met Lys
65                  70                  75                  80

Leu Pro Lys Ser Ala Lys Pro Val Ser Lys Ile Arg Val Ala Thr Pro
                85                  90                  95

Met Leu Met Gln Ala Leu Pro Met Glu Gly Leu Ser His Gly
            100                 105                 110

<210> SEQ ID NO 17
<211> LENGTH: 333
<212> TYPE: PRT
<213> ORGANISM: Artificial Sequence
<220> FEATURE:
<223> OTHER INFORMATION: Synthetic Peptide

<400> SEQUENCE: 17

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
        35                  40                  45

Gly Ala Leu Tyr Thr Gly Phe Ser Val Leu Val Ala Leu Leu Leu Ala
50                  55                  60

Gly Gln Ala Thr Thr Ala Tyr Phe Leu Phe Gln Gln Gly Arg Leu
65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
        115                 120                 125

Ala Arg Val Lys Lys Asn Asp Pro Leu Pro Gly Ala Thr Val Gly Gly
    130                 135                 140

Tyr Ser Gly Gly Asp Leu Val Ser Glu Arg Ala Ser Val Ser Val Lys
145                 150                 155                 160

Lys Gly Gly Tyr Lys Tyr Asn Ala Gln Ala Asn Arg Ser Val Tyr Asp
                165                 170                 175

Ser Arg Asn Phe Asp Pro Gly Lys Glu Phe Leu Lys Leu Val Leu Tyr
            180                 185                 190

Phe Lys Ser Lys Asp Phe Lys Asn Arg Lys Trp Asp Glu Arg Glu Lys
        195                 200                 205

Asn Asn Lys Asn Met Asp Pro Val Lys Asn Gln Ala Gln Ser Gly Ser
    210                 215                 220

Ser Trp Ala Phe Ala Pro Val Pro Ser Arg Ser Tyr Thr Leu Ala Glu
225                 230                 235                 240

Gln Glu Leu Val Asp Ser Glu Thr Thr Ser Ile Lys Gly Leu Lys Met
                245                 250                 255

Ser Ala Arg Arg Ser Leu Asn Pro Arg Leu Gly Phe Arg Gly Gly Trp
            260                 265                 270

Ser Thr Thr Gly Asn Thr Leu Ser Asn Val Ser Leu Gly Arg Asn Arg
          275                 280                 285

Phe Ser Ser Gln Asp Glu Leu Ile His Val Ile Val Trp Asn Lys Gly
          290                 295                 300

Ser Gly Arg Val Arg His Val Ala Arg Ala Glu Asn Ala Ala Glu Asn
305                 310                 315                 320

Lys Ile Lys Ala Ala Gly Gly Ala Ser Val Leu Arg Ala
                325                 330

<210> SEQ ID NO 18
<211> LENGTH: 273
<212> TYPE: PRT
<213> ORGANISM: Artificial Sequence
<220> FEATURE:
<223> OTHER INFORMATION: Culicoides spec.

<400> SEQUENCE: 18

Met Asn Ile Lys Ser Thr Ile Val Ile Ala Ile Ile Ser Ala Val
1               5                   10                  15

Tyr Ala Ala Asp His Gln Ser Gln Lys Ala Val Ala Val Pro Ser Tyr
                20                  25                  30

Thr Tyr Arg Arg Pro Ser Thr Lys Ile Ile Gly Gly Ala Pro Ala Phe
                35                  40                  45

Ser His Gln Phe Pro Trp Gln Ala Ser Ile Thr Val Thr Ala Cys Ser
            50                  55                  60

Gly Asp Trp Cys Ser Leu Cys Gly Gly Ser Leu Ile Ser Arg Lys His
65                  70                  75                  80

Val Leu Thr Ala Ala His Cys Thr Lys Gly Leu Ser Ser Phe Thr Ile
                85                  90                  95

Gly Leu Gly Ser Asn Thr Arg Asn Arg Pro Ala Val Thr Val Val Ala
                100                 105                 110

Lys Ser Lys Thr Glu His Pro Lys Tyr Asn Pro Glu Ser Leu Ala Asn
            115                 120                 125

Asp Val Ser Ile Ile Thr Leu Ser Leu Asn Val Asn Leu Asn Asn Asn
130                 135                 140

Ile Lys Val Ile Ser Leu Ala Asn Ser Gly Ile Gly Thr Leu Val Asn
145                 150                 155                 160

Arg Asn Ala Phe Val Ser Gly Tyr Gly Lys Thr Ser Ser Ser Ser Glu
                165                 170                 175

Gly Ser Asn Thr Leu Asn Tyr Leu Ser Met Arg Leu Ile Ser Asn Ser
            180                 185                 190

Asp Cys Tyr Lys Val Phe Gly Pro Gln Ile Tyr Ser Thr Thr Leu Cys
            195                 200                 205

Ala Val Ala Arg Ser Ser Val His Lys Asn Val Cys Ser Gly Asp Ser
            210                 215                 220

Gly Gly Pro Leu Val Ile Lys Arg Asn Gly Asn Tyr Val Gln Val Gly
225                 230                 235                 240

Ile Val Ser Phe Val Ala Lys Val Gly Cys Asp Ala Gly Phe Pro Ser
                245                 250                 255

Gly Tyr Ala Arg Val Ser Ser Phe Arg Asn Trp Ile Thr Gln Asn Met
                260                 265                 270

Asn

<210> SEQ ID NO 19
<211> LENGTH: 159

```
<212> TYPE: PRT
<213> ORGANISM: Artificial Sequence
<220> FEATURE:
<223> OTHER INFORMATION: Culicoides spec.

<400> SEQUENCE: 19

Met Lys Phe Ser Val Ser Lys Leu Ser Leu Leu Cys Ile Thr Ile
1               5                   10                  15

Leu Cys Ile Cys Phe Ala Thr Ala Ala Pro Gln Trp Gln Ile Ser Glu
            20                  25                  30

Leu Ser Glu Gln Ser Asn Val Ile Lys Cys Ser Asn Glu Asn Asn Phe
            35                  40                  45

Gly Ile Tyr Lys Glu Leu Cys Gln Phe Leu Lys Lys Ile Tyr Ile Lys
        50                  55                  60

Ala Pro Asp Glu Asp Leu Gly Ser Tyr Leu Arg Gly Gly Leu Gln Ser
65                  70                  75                  80

Ala Ala Asn Arg Leu Leu Asp Pro Thr Val Thr Leu Pro Lys Asn Thr
                85                  90                  95

Leu Lys Asn Val Glu Asp Cys Met Lys Asn Phe Gln Ala Val Ile Asn
            100                 105                 110

Glu Tyr Asn Val Val Ala Leu Lys Lys Tyr Gln Glu Cys Asp Gly Gln
        115                 120                 125

Cys Ala Lys Gln Ala Gly Gln Leu Phe Glu Asn Asp Ala Ser Lys Thr
130                 135                 140

Ala Gly Arg Met Gly Asp Cys Ile Val Ser Leu Ala Ala Leu His
145                 150                 155

<210> SEQ ID NO 20
<211> LENGTH: 383
<212> TYPE: PRT
<213> ORGANISM: Artificial Sequence
<220> FEATURE:
<223> OTHER INFORMATION: Synthetic Peptide

<400> SEQUENCE: 20

Met His His His His His Tyr Gly Arg Lys Lys Arg Gln Arg
1               5                   10                  15

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
            35                  40                  45

Gly Ala Leu Tyr Thr Gly Phe Ser Val Leu Val Ala Leu Leu Leu Ala
        50                  55                  60

Gly Gln Ala Thr Thr Ala Tyr Phe Leu Phe Gln Gln Gln Gly Arg Leu
65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
            115                 120                 125

Ala Asp His Gln Ser Gln Lys Ala Val Ala Val Pro Ser Tyr Thr Tyr
130                 135                 140

Arg Arg Pro Ser Thr Lys Ile Ile Gly Gly Ala Pro Ala Phe Ser His
145                 150                 155                 160

Gln Phe Pro Trp Gln Ala Ser Ile Thr Val Thr Ala Ser Ser Gly Asp
                165                 170                 175
```

```
Trp Ser Ser Leu Ser Gly Gly Ser Leu Ile Ser Arg Lys His Val Leu
            180                 185                 190

Thr Ala Ala His Ser Thr Lys Gly Leu Ser Ser Phe Thr Ile Gly Leu
        195                 200                 205

Gly Ser Asn Thr Arg Asn Arg Pro Ala Val Thr Val Ala Lys Ser
210                 215                 220

Lys Thr Glu His Pro Lys Tyr Asn Pro Glu Ser Leu Ala Asn Asp Val
225                 230                 235                 240

Ser Ile Ile Thr Leu Ser Leu Asn Val Asn Leu Asn Asn Ile Lys
            245                 250                 255

Val Ile Ser Leu Ala Asn Ser Gly Ile Gly Thr Leu Val Asn Arg Asn
        260                 265                 270

Ala Phe Val Ser Gly Tyr Gly Lys Thr Ser Ser Ser Glu Gly Ser
        275                 280                 285

Asn Thr Leu Asn Tyr Leu Ser Met Arg Leu Ile Ser Asn Ser Asp Ser
290                 295                 300

Tyr Lys Val Phe Gly Pro Gln Ile Tyr Ser Thr Thr Leu Ser Ala Val
305                 310                 315                 320

Ala Arg Ser Ser Val His Lys Asn Val Ser Ser Gly Asp Ser Gly Gly
                325                 330                 335

Pro Leu Val Ile Lys Arg Asn Gly Asn Tyr Val Gln Val Gly Ile Val
            340                 345                 350

Ser Phe Val Ala Lys Val Gly Ser Asp Ala Gly Phe Pro Ser Gly Tyr
        355                 360                 365

Ala Arg Val Ser Ser Phe Arg Asn Trp Ile Thr Gln Asn Met Asn
370                 375                 380
```

<210> SEQ ID NO 21
<211> LENGTH: 383
<212> TYPE: PRT
<213> ORGANISM: Artificial Sequence
<220> FEATURE:
<223> OTHER INFORMATION: Synthetic Peptide

<400> SEQUENCE: 21

```
Met Tyr Gly Arg Lys Lys Arg Arg Gln Arg Arg Met Glu Asp Gln
1               5                   10                  15

Arg Asp Leu Ile Ser Asn His Glu Gln Val Pro Ile Leu Gly Gln Arg
            20                  25                  30

Pro Ala Ala Pro Glu Arg Lys Ser Ser Arg Gly Ala Leu Tyr Thr Gly
        35                  40                  45

Phe Ser Val Leu Val Ala Leu Leu Leu Ala Gly Gln Ala Thr Thr Ala
50                  55                  60

Tyr Phe Leu Phe Gln Gln Gln Gly Arg Leu Asp Lys Leu Thr Val Thr
65                  70                  75                  80

Ala Gln Asn Leu Gln Leu Glu Lys Leu Arg Met Lys Leu Pro Lys Ser
                85                  90                  95

Ala Lys Pro Val Ser Lys Ile Arg Val Ala Thr Pro Met Leu Met Gln
            100                 105                 110

Ala Leu Pro Met Glu Gly Leu Ser His Gly Ala Asp His Gln Ser Gln
        115                 120                 125

Lys Ala Val Ala Val Pro Ser Tyr Thr Tyr Arg Pro Ser Thr Lys
130                 135                 140

Ile Ile Gly Gly Ala Pro Ala Phe Ser His Gln Phe Pro Trp Gln Ala
145                 150                 155                 160
```

```
Ser Ile Thr Val Thr Ala Ser Ser Gly Asp Trp Ser Leu Ser Gly
                165                 170                 175

Gly Ser Leu Ile Ser Arg Lys His Val Leu Thr Ala Ala His Ser Thr
            180                 185                 190

Lys Gly Leu Ser Ser Phe Thr Ile Gly Leu Gly Ser Asn Thr Arg Asn
            195                 200                 205

Arg Pro Ala Val Thr Val Val Ala Lys Ser Lys Thr Glu His Pro Lys
        210                 215                 220

Tyr Asn Pro Glu Ser Leu Ala Asn Asp Val Ser Ile Ile Thr Leu Ser
225                 230                 235                 240

Leu Asn Val Asn Leu Asn Asn Asn Ile Lys Val Ile Ser Leu Ala Asn
                245                 250                 255

Ser Gly Ile Gly Thr Leu Val Asn Arg Asn Ala Phe Val Ser Gly Tyr
            260                 265                 270

Gly Lys Thr Ser Ser Ser Ser Glu Gly Ser Asn Thr Leu Asn Tyr Leu
            275                 280                 285

Ser Met Arg Leu Ile Ser Asn Ser Asp Ser Tyr Lys Val Phe Gly Pro
            290                 295                 300

Gln Ile Tyr Ser Thr Thr Leu Ser Ala Val Ala Arg Ser Ser Val His
305                 310                 315                 320

Lys Asn Val Ser Ser Gly Asp Ser Gly Gly Pro Leu Val Ile Lys Arg
                325                 330                 335

Asn Gly Asn Tyr Val Gln Val Gly Ile Val Ser Phe Val Ala Lys Val
            340                 345                 350

Gly Ser Asp Ala Gly Phe Pro Ser Gly Tyr Ala Arg Val Ser Ser Phe
            355                 360                 365

Arg Asn Trp Ile Thr Gln Asn Met Asn His His His His His His
        370                 375                 380

<210> SEQ ID NO 22
<211> LENGTH: 263
<212> TYPE: PRT
<213> ORGANISM: Artificial Sequence
<220> FEATURE:
<223> OTHER INFORMATION: Synthetic Peptide

<400> SEQUENCE: 22

Met His His His His His His Tyr Gly Arg Lys Lys Arg Arg Gln Arg
1               5                   10                  15

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Phe Gln Gln Gln Gly Arg Leu
65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
            115                 120                 125

Ala Pro Gln Trp Gln Ile Ser Glu Leu Ser Glu Gln Ser Asn Val Ile
        130                 135                 140
```

Lys Ser Ser Asn Glu Asn Phe Gly Ile Tyr Lys Glu Leu Ser Gln
145                 150                 155                 160

Phe Leu Lys Lys Ile Tyr Ile Lys Ala Pro Asp Glu Asp Leu Gly Ser
                165                 170                 175

Tyr Leu Arg Gly Gly Leu Gln Ser Ala Ala Asn Arg Leu Leu Asp Pro
            180                 185                 190

Thr Val Thr Leu Pro Lys Asn Thr Leu Lys Asn Val Glu Asp Ser Met
            195                 200                 205

Lys Asn Phe Gln Ala Val Ile Asn Glu Tyr Asn Val Ala Leu Lys
210                 215                 220

Lys Tyr Gln Glu Ser Asp Gly Gln Ser Ala Lys Gln Ala Gly Gln Leu
225                 230                 235                 240

Phe Glu Asn Asp Ala Ser Lys Thr Ala Gly Arg Met Gly Asp Ser Ile
                245                 250                 255

Val Ser Leu Ala Ala Leu His
            260

<210> SEQ ID NO 23
<211> LENGTH: 263
<212> TYPE: PRT
<213> ORGANISM: Artificial Sequence
<220> FEATURE:
<223> OTHER INFORMATION: Synthetic Peptide

<400> SEQUENCE: 23

Met Tyr Gly Arg Lys Lys Arg Gln Arg Arg Arg Met Glu Asp Gln
1               5                   10                  15

Arg Asp Leu Ile Ser Asn His Glu Gln Val Pro Ile Leu Gly Gln Arg
                20                  25                  30

Pro Ala Ala Pro Glu Arg Lys Ser Ser Arg Gly Ala Leu Tyr Thr Gly
            35                  40                  45

Phe Ser Val Leu Val Ala Leu Leu Leu Ala Gly Gln Ala Thr Thr Ala
50                  55                  60

Tyr Phe Leu Phe Gln Gln Gln Gly Arg Leu Asp Lys Leu Thr Val Thr
65                  70                  75                  80

Ala Gln Asn Leu Gln Leu Glu Lys Leu Arg Met Lys Leu Pro Lys Ser
                85                  90                  95

Ala Lys Pro Val Ser Lys Ile Arg Val Ala Thr Pro Met Leu Met Gln
            100                 105                 110

Ala Leu Pro Met Glu Gly Leu Ser His Gly Ala Pro Gln Trp Gln Ile
            115                 120                 125

Ser Glu Leu Ser Glu Gln Ser Asn Val Ile Lys Ser Ser Asn Glu Asn
130                 135                 140

Asn Phe Gly Ile Tyr Lys Glu Leu Ser Gln Phe Leu Lys Lys Ile Tyr
145                 150                 155                 160

Ile Lys Ala Pro Asp Glu Asp Leu Gly Ser Tyr Leu Arg Gly Leu
                165                 170                 175

Gln Ser Ala Ala Asn Arg Leu Leu Asp Pro Thr Val Thr Leu Pro Lys
            180                 185                 190

Asn Thr Leu Lys Asn Val Glu Asp Ser Met Lys Asn Phe Gln Ala Val
            195                 200                 205

Ile Asn Glu Tyr Asn Val Ala Leu Lys Lys Tyr Gln Glu Ser Asp
210                 215                 220

Gly Gln Ser Ala Lys Gln Ala Gly Gln Leu Phe Glu Asn Asp Ala Ser
225                 230                 235                 240

```
Lys Thr Ala Gly Arg Met Gly Asp Ser Ile Val Ser Leu Ala Ala Leu
            245                 250                 255

His His His His His His His
            260
```

US 10,919,945 B2

MODULAR ANTIGEN TRANSPORTATION MOLECULES AND USES THEROF

SEQUENCE LISTING

This application contains a sequence listing in accordance with 37 C.F.R. 1.821-1.825. The content of the ASCII text file of the sequence listing named 01-3045-US-2-SEQ which is 56 kb in size was created on Jan. 23, 2018 and electronically submitted via EFS-Web herewith the application is incorporated herein by reference in its entirety.

FIELD OF THE INVENTION

The present invention relates to (isolated) recombinant proteins, also referred to as improved MAT (iMAT) molecules, comprising at least one translocation module, at least one targeting module and at least one antigen module, wherein at least one cysteine residue is substituted with a different amino acid residue. The iMAT molecules may be produced with substantially reduced manufacturing efforts and are species-specific, safer and immunologically very effective. Such (isolated) recombinant proteins are useful specifically as vaccines, e.g., for therapy and/or prevention of allergies and/or infections and/or prevention of transmission of infections in equines.

BACKGROUND OF THE INVENTION

The processing of antigens by antigen-presenting cells (APCs) takes place by two different routes. Antigens occurring inside the cell are presented by MHC I (major histocompatibility complex class I, MHC class I) molecules on the cell surface, whereas extracellular antigens are presented by MHC II (major histocompatibility complex class II, MHC class II) molecules on the cell surface. Both mechanisms initiate an immune response by the host to the antigen. The route taken by the antigen from uptake into the cell until presentation on the cell surface in the form of an MHC II-antigen complex proceeds via various cell organelles, inter alia via the endoplasmic reticulum, the Golgi apparatus, the trans-Golgi network, lysosomes, endosomes and via MHC class II compartments (MIICs). The MIICs play an important part in the MHC II-mediated antigen presentation. In these organelles of the cell, the MHC II molecules are loaded with low molecular weight antigens or with proteolytic fragments of proteins. In this process, the invariant chain (also called MHC II gamma chain or Ii) which is initially bound to the MHC II molecule undergoes proteolytic degradation, and the antigen is bound to the MHC II molecule under the regulation of various proteins which bind directly or indirectly to MHC II. These regulatory molecules in humans include, inter alia HLA-DM, HLA-DO, LAMP-1, LAMP-2, CD63, CD83, etc. The exact function of these proteins is in part unexplained as of yet, but many of them have signal sequences which promote their transport to the lysosomes, to the endosomes, to the trans-Golgi network, to the MIICs, etc. A number of proteases are involved in the proteolytic processing necessary, so that the antigen can be presented on MHC II molecules. The proteases present in MIICs include, inter alia various members of the cathepsin family such as, for example, cathepsin S and cathepsin L. In species other than humans, the homologue MHC Class II molecules have different amino acid sequences. In Equine animals the organization of the MHC system is similar to humans with contiguous class I, III, and II regions (Kelley J et al., Immunogenetics 2005, 56: 683-695).

The concept of providing modular antigen transportation (MAT) molecules for modulating immune responses, associated constructs, method and uses thereof is disclosed in WO 2004/035793 (US equivalent US 2005/0281816), hereby incorporated by reference. This document describes the usefulness of a three-part-molecule, the MAT molecule, for introducing epitopes of antigens into cells, thus, determining the immune response to be modulated by such MAT molecule. Therein, various translocation modules, targeting modules as well as antigen modules are described. This technology and its underlying method make it possible, firstly, to convey antigens efficiently from the extracellular space into the intracellular space of a target cell, and, secondly, make it possible for the antigens, after arrival in the interior of the cell, to reach efficiently cell organelles in order to be subsequently processed for antigen presentation. Generally, the two-stage process can be utilized for the targeted, efficient modulation of the immune response in a subject. The use of MAT molecules is disclosed for example in Martínez-Gómez J M et al. [Allergy 2009, 64(1): 172-178]; Rose H (Arb Paul Ehrlich Inst Bundesinstitut Impfstoffe Biomed Arzneim Langen Hess, 2009, 96, 319-327) as well as recently in Senti G et al. [J Allergy Clin Immunol., 2012, 129(5): 1290-1296]. Based on the MAT technology, the major cat allergen Fel d1 was fused to a TAT-derived protein translocation domain and to a truncated invariant human chain for targeting the MHC class II pathway. Immunogenicity was evaluated in mice, while potential safety issues were assessed by suitable tests based on basophil reactivities from cat-dander-allergic patients. The possible use of this model compound has been demonstrated. It is described therein, that it is expected that MAT molecules are safer and more efficient in inducing the desired immune response, namely hyposensitization, than recombinant allergens or allergen extracts in conventional allergen-specific immunotherapy (SIT). In the recent publication by Senti G. et al. intralymphatic immunotherapy for cat dander allergy in humans inducing tolerance after three injections was described. Therein, a first-in-human clinical study with the MAT-Fel d1 was described, demonstrating safety and induction of allergen tolerance after intra-lymphatic injection of three injections only.

Further prior art is as follows:

Gadermaier G et al. (Molecular Immunology 2010, 47: 1292-1298) describe the targeting of the cysteine-stabilized fold of Art v1 for immunotherapy of *Artemisia* pollen allergy. The authors used genetic engineering approaches for targeting Art v1 posttranslational modifications aiming at the creation of hypoallergenic molecules: (i) disulfide bridges of the defensin domain were disrupted by site-directed mutagenesis and (ii) the mutant constructs expressed in *E. coli* for the production of non-glycosylated proteins. However, the objective was clearly only manipulating the three-dimensional fold of the Art v1 defensin domain to abrogate IgE-binding (i.e. creating a hypoallergenic molecule) by exchanging single cysteine residues for serine—while keeping intact (i.e. unmodified) the recognized T-cell epitopes (even if such contain cysteine residues).

The report of the 3$^{rd}$ Havemeyer workshop on allergenic diseases of the Horse (Hólar, Iceland, June 2007, Veterinary Immunology and Immunotherapy 2008, 126: 351-361) focused on immunological and genetic aspects of insects bite hypersensitivity (IBH) and recurrent airway obstruction (RAO). At this workshop, novel approaches for SIT against IBH were discussed, among others, the use of viral vectors or protein vaccination with allergens coupled to modular antigen translocating (MAT) molecules.

In SIAF Annual Reports 2010 and 2011 Crameri R reports the use of MAT technology for vaccination of IBH-affected horses.

However, major problems arose when producing and manufacturing the MAT molecules described in the prior art. In particular standard methods used in developing a downstream process (DSP) for manufacturing of the MAT molecules under good manufacturing practice (GMP) could not be applied. It was not possible to purify a homogeneous molecular species of the MAT molecules, evidently due to their anomalous physicochemical properties.

Several methods of purification could not be applied (see Example 5 herein) with the MAT molecules described in the prior art although different separation principles (e.g., size exclusion chromatography, RP-HPLC) were tested. Methods applied for determination of purity for recombinant proteins in general include chromatographic separation, e.g., RP-HPLC and electrophoretic separation (e.g. capillary zone electrophoresis, isoelectric focusing, SDS-PAGE under reducing or non-reducing conditions). Also, these analytical methods could not be applied on MAT molecules without molecule-specific adaptations. For the assessment of purity, an adapted specific SDS-PAGE test procedure had to be developed. This test procedure includes sample preparation with reducing agent and lithium dodecyl sulfate (LDS) and heating up to 75° C., resulting in multiple, reproducible sharp bands after electrophoretic separation. Staining with Coomassie blue dye leads to linear quantitative behavior (densitometry) in gels. Using a monoclonal antibody that allows for detection of the allergen module in a MAT molecule exhibited a main band and several minor bands. All bands migrate reproducibly to the same position as in the original gel also after re-loading a second gel with excised bands of the first gel. Surprisingly, in all of these bands with apparent lower and higher molecular weight, the full length MAT molecules were identified by excision of bands out of the gel, their tryptic digestion and subsequent analysis by mass spectrometry (nanoLC/ESI-MS-MS). From these experiments an untypical, anomalous behavior of different folding variants of MAT molecules in the SDS-PAGE can be concluded ("gel shifting"). Furthermore, in all batches of MAT molecules multimeric forms of the protein could be detected which were difficult to separate from monomeric forms.

For e.g. economic aspects, but also for regulatory requirements, it is necessary to improve (i) the manufacturing process of the MAT molecules and (ii) their suitability for standard analytical methods of purity determination. Additionally, for adapting the MAT molecules to specific target species, such as equines, adaption of the immunological targeting within the MAT technology is required.

Additionally, the MAT molecules are readily employed in allergies elicited by a known major allergen (e.g., cat dander allergy in humans by Fel d1). However, it seems difficult to employ the MAT molecules of the prior art in clinical settings, such as allergies, where for instance a variety of non-cross-reactive allergens are known to be involved, but the importance of such allergens in eliciting the allergy is unknown (i.e. the major allergens are unknown).

The objective underlying the invention is to provide improved MAT molecules useful as active agents in pharmaceutical composition, such as vaccines, which overcome the problems of the prior art.

DISCLOSURE OF THE INVENTION

Summary of the Invention

In one aspect, the objective underlying the invention has surprisingly been solved by providing a(n) (isolated) recombinant protein, preferably an improved MAT (iMAT) molecule, comprising:
i. at least one first module being an amino acid sequence allowing the translocation of the iMAT molecule from the extracellular space into the interior of cells,
ii. at least one second module being an amino acid sequence allowing species-specific intracellular targeting of the iMAT molecule to the cell organelles which are involved in the processing of antigens and/or the loading of MHC molecules with antigens, preferably processed antigens, and
iii. at least one third module as antigen module being an amino acid sequence derived from at least one full or partial epitope of at least one antigen, preferably at least one allergen, determining the specificity of an immune response modulated by such iMAT molecule, characterized in that at least in the antigen module(s) at least one cysteine residue is substituted with a different amino acid residue, preferably serine, leucine, isoleucine and/or aspartic acid.

Preferably, in the at least one antigen module all cysteine residues are substituted with a different amino acid residue, preferably serine, leucine, isoleucine and/or aspartic acid. More preferably in the entire iMAT molecule all cysteine residues are substituted with a different amino acid residue, preferably serine, leucine, isoleucine and/or aspartic acid.

Preferably, if not all cysteine residues are substituted with a different amino acid residue, preferably serine, leucine, isoleucine and/or aspartic acid, an even number of cysteine residues remains in the entire iMAT molecule.

Preferably, all of such modules are covalently linked to each other, optionally by additional spacer module(s) between two or more adjacent, optionally all, of such first, second and/or third modules.

More preferably, all of such modules are covalently linked to each other and no additional spacer module(s) are present between two or more adjacent modules of such first, second and/or third modules at all.

In another aspect, the objective underlying the invention has surprisingly been solved by providing a vaccine or immunogenic composition or pharmaceutical composition comprising the (isolated) recombinant protein as herein disclosed and claimed.

In another aspect, the objective underlying the invention has surprisingly been solved by providing the (isolated) recombinant protein as herein disclosed and claimed or the vaccine or immunogenic composition or pharmaceutical composition as herein disclosed and claimed for use in a method of prevention and/or therapy of one or more allergies in equines, preferably insect bite hypersensitivity (IBH), urticaria and/or recurrent airways obstruction (RAO). Corresponding methods of prevention and/or treatment of equines in need thereof and uses for the preparation of a pharmaceutical composition/medicament for the prevention and/or treatment of equines are also intended to be within the scope of the present invention.

In another aspect, the objective underlying the invention has surprisingly been solved by providing the (isolated) recombinant protein as herein disclosed and claimed or the vaccine or immunogenic composition or pharmaceutical composition as herein disclosed and claimed for use in a method of prevention and/or therapy of one or more infectious diseases in equines and/or prevention of transmission of one or more infectious diseases in equines and/or prevention of transmission of one or more infectious diseases in equines by vectors, preferably by blood feeding flies, midges, ticks and/or mosquitoes, more preferably rhodoccus pneumonia, strangles, African horse sickness, West Nile Virus infection, dermatophytosis and/or parasites of the digestive tract and/or other organs and/or cryptosporidiosis, helminths and/or their prepatent stages. Corresponding methods of prevention and/or treatment of equines in need thereof and uses for the preparation of a pharmaceutical composition/medicament for the prevention and/or treatment of equines are also intended to be within the scope of the present invention.

In a further aspect, the objective underlying the invention has surprisingly been solved by providing a nucleic acid encoding the (isolated) recombinant protein as herein disclosed and claimed.

In a further aspect, the objective underlying the invention has surprisingly been solved by providing a vector comprising at least one nucleic acid as herein disclosed and claimed.

In yet a further aspect, the objective underlying the invention has surprisingly been solved by providing a primary cell or cell line comprising at least one nucleic acid as herein disclosed and claimed and/or at least one vector as herein disclosed and claimed.

Surprisingly, the iMAT molecules according to the present invention, as herein disclosed and claimed, do possess physicochemical and/or immunological characteristics that render them superior to the MAT molecules of the pertinent prior art:

i. The substitution of at least one cysteine residue, preferably all cysteine residues, with a different amino acid residue in the antigen module(s), preferably entire iMAT molecule, which was selected in silico not to compromise the stability of the final iMAT molecule, renders the iMAT molecule according to the present invention surprisingly suitable for the application of standard purification procedures for biopharmaceuticals as well as for standard analytical methods.

ii. The preferred direct covalent linkage of the modules of the iMAT molecule, i.e., first translocation module, second targeting module and third antigen module, without any additional spacer modules between such modules, i.e., no additional spacer modules between two or more adjacent modules of such first, second and/or third modules at all, contributes in addition to (i) the superior characteristics of the iMAT molecules according to the present invention: such iMAT molecules which are thought to be more rigid in three-dimensional structure and hence unable to form conformational IgE epitopes, are even more hypoallergenic—virtually no allergenicity could be detected as shown in Example 2 herein.

iii. The preferred presence of a(n) (quasi) N-terminal His-tag results in iMAT molecules according to the present invention that can be used as surrogate markers for monitoring immunity and/or duration of immunity since such tag module, optionally together with one or more adjacent amino acid residues from the translocation module, can be used to induce a specific immunologically detectable signal (e.g. an antibody) in the target subject, that is specific to the generic structure of the iMAT molecules (see Example 1 herein). Additionally, the presence of such tag module can be used for separating proteins in a sample comprising the iMAT molecules according to the present invention, e.g. using zinc- or cobalt-charged solid supports, and hence further improves the possibility to produce iMAT molecules according to the present invention without aggregation during the purification process.

iv. The at least one targeting module in the iMAT molecules according to the present invention preferably is species-specific, i.e. in case of an intended application of such iMAT molecules to equines an equine targeting module, e.g. the equine invariant chain, is chosen. By this species-specific targeting optimized binding characteristics of the iMAT molecules according to the present invention to the MHC Class II molecules can successfully be achieved.

v. The at least one antigen module in the iMAT molecules according to the present invention is preferably an allergen. This could be derived from mold (fungi and/or their spores), pollen, house dust or forage mites (and/or their feces), preferably pollen from tree, grass, herbaceous, *ambrosia* and/or brassicaceae pollen and/or fungi and/or their spores of the genera *aspergillus, alternaria, botrytis, cercospora, cladosporium, curvularia, drechslera, eurotium, helminthosporium, epicoccum, erysiphe/oidium, fusarium, lichtheimia, nigrospora, penicillium, periconia, peronospora, polythrincium, saccharopolyspora* (formerly also *faenia* or *micropolyspora*), *thermoactinomyces, stemphylium, torula* and/or mites (or their feces) of the genera *acarus, glycophagus, tyrophagus, dermatophagoides*. The at least one antigen module in the iMAT molecules according to the present invention is more preferably a *culicoides* allergen. The allergen was selected according to the following criteria: when major allergens eliciting an allergy in subjects are unknown, the at least one antigen module in the iMAT molecules according to the present invention can be selected by a bioinformatics approach as described exemplarily and in detail in Examples 6 and 7 herein. By this means improved MAT molecules can be achieved which are useful specifically as vaccines, e.g. for therapy and/or prevention of allergies in equines. The at least one antigen module in the iMAT molecules according to the present invention may also be an antigen of a pathogen involved in one or more infectious disease(s). This could be derived from the genera *rhodococcus, streptococcus, orbivirus, flavivirus, trichophyton, microsporum, cryptosporidium* and/or *strongylus*. The at least one antigen module in the iMAT molecules according to the present invention may also be an antigen of a vector involved in the transmission of one or more infectious disease(s), e.g. *culicoides, culex* and/or *ixodes* saliva components. By this means improved MAT molecules can be achieved which are useful specifically as vaccines, e.g. for therapy and/or prevention and/or prevention of transmission of infectious diseases in equines.

In particular, the present invention provides (isolated) recombinant proteins exhibiting an improved solubility, that are readily applicable to chromatographic separation techniques and that show an improved stability.

In addition, the (isolated) recombinant proteins according to the present invention preferably display high activities and efficacies in inducing the desired immunological effects, namely, advantageously species specific modulating the immune response against allergens in a subject, preferably an equine. By this means treatment and amelioration of symptoms of IBH affected equines becomes feasible.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The terms "isolated recombinant protein", "recombinant protein" and/or "improved MAT (iMAT) molecule" are interchangeably used in the course of the present invention. They all have the identical meaning.

The term "module" in the course of the present invention refers to a specific amino acid sequence, e.g. a part, a unit or a moiety of a polypeptide, usually short amino acid/peptide sequences, having a defined function.

The term "first module being an amino acid sequence allowing the translocation of the (isolated) recombinant protein, preferably improved MAT (iMAT) molecule, from the extracellular space into the interior of cells", herein also interchangeably referred to as "translocation module" or "translocation sequence", in the course of the present invention refers to a specific amino acid sequence that promotes the transport of the cargo molecule, e.g., amino acid sequence, peptide, polypeptide, protein and other classes of substances, such as nucleic acids or pharmaceutically active ingredients (API), to the interior of cells, in particular eukaryotic cells, more particular, cells expressing the MHC class II molecules on the surface and/or the MHC class I molecules on the surface, as known in the literature.

By the presence of the translocation module it is possible to promote the entry of said cargo molecule into the cells.

Amino acid sequences useful as translocation modules are described in the prior art. For example, U.S. Pat. No. 7,653,866 discloses several useful translocation sequences including the HIV-tat molecule or the protein VP22, which is derived from herpes simplex virus. This principal of promoting the entry of a given target molecule into the interior of cells is described numerously in various studies in the pertinent patent and non-patent literature. In addition, suitable translocation sequences include homeoprotein sequences, leucine zipper sequences, arginine-rich and/or lysine-rich sequences, and various other sequences of proteins or polypeptides which are secreted despite the absence of a secretion signal sequence. Particularly useful are viral peptide sequences, e.g. the protein HIV transcriptional activator protein (HIV tat). The Tat sequence or Tat peptide has been described in the prior art including various modifications. All the variations described in the prior art for peptide sequences of Tat are generally suitable as translocation modules. Other examples include the VP22 peptide as well as antennapedia peptides derived from the *drosophila* homeotic protein antennapedia. In addition, other homeoproteins may be used. Various examples of suitable homeoproteins are described in the prior art. In addition, leucine zipper proteins, like human cFos-(139-164), or human cJun-(252-279) can be used. Moreover, arginine-rich and/or lysine-rich peptides are suitable as translocation modules including sequences like HIV-1 rev (34-50) or other peptides derived from virus or yeast. Of course, the polyarginine-rich and/or polylysine-rich peptides can be produced synthetically. Said polyarginine-rich and/or polylysine-rich peptides may comprise further amino acids. Suitable examples are described in the pertinent prior art.

In a preferred embodiment, the at least one translocation module comprises, and preferably consists of, an amino acid sequence which does not consist of a complete protein sequence, as illustrated above, but instead of a minimal sequence still being functional, i.e., capable of effectively promoting cell entry. A suitable minimal sequence is, for instance, the amino acid sequence according to SEQ ID NO: 1.

In another preferred embodiment, the at least one translocation module comprises, and preferably consists of, HIV-tat, VP22 and/or Antennapedia or a partial sequence thereof, provided that such at least one translocation module is functional as a module for translocation from the extracellular space into the interior of cells.

The term "second module being an amino acid sequence allowing species-specific intracellular targeting of the (isolated) recombinant protein, preferably improved MAT (iMAT) molecule, to the cell organelles which are involved in the processing of antigens and/or the loading of MHC molecules with antigens, preferably processed antigens", herein also interchangeably referred to as "targeting module" or "targeting sequence", in the course of the present invention refers to a specific amino acid sequence that allows/promotes the intracellular transport of the (isolated) recombinant proteins, as disclosed and claimed herein, to such cell organelles that are involved in the processing of antigens and/or the loading of MHC molecules with antigens.

In particular, such cell organelles include the endoplasmic reticulum, the Golgi apparatus, the trans-Golgi network, lysosomes, endosomes and MHC II compartments. These intracellular organelles are involved in processes such as, for example, the transport and/or processing of antigens, the preparation and/or loading of MHC II molecules with antigens or processed antigens, and/or the transport of the MHC II molecules loaded with such antigens to the cell surface.

A number of sequences are known in the prior art. A prominent example of useful targeting sequences includes the invariant chain of MHC class II molecules also known as Ii invariant chain or MHC II gamma chain. Various variants of the invariant chain are described in the patent and non-patent literature.

In a preferred embodiment of the present invention, the invariant chain is chosen from the species in which the immune response should be modulated and/or from the species in which the iMAT molecule should be intracellularly targeted.

For example, for equines, such as horses, the preferred invariant chain chosen is the equine invariant chain, comprising, preferably consisting of the amino acid sequence according to SEQ ID NO: 2 or fragments thereof provided such fragments maintain their intracellular transport function. Preferred such fragments are the amino acid sequences according to SEQ ID NOS: 15 and/or 16.

Other suitable examples for targeting sequences include lysosomal membrane proteins, comprising sequences suitable as targeting modules. That are, a number of membrane proteins occurring in lysosomes which have sequence motifs that allow targeting the lysosome. These groups of proteins include inter alia lamp 1, lamp 2, lamp 3, limp II and lap. In addition, tetraspan proteins are known in the prior art as targeting modules. Additional proteins can be found in the endosomal/lysosomal compartments that show targeting properties. A skilled person is aware how to determine suitable targeting sequences accordingly.

In another preferred embodiment, the at least one targeting module comprises, and preferably consists of, the equine invariant chain and more preferably consists of one or more of the amino acid sequences of SEQ ID NOS: 2, 15, 16.

The term "third module as antigen module being an amino acid sequence derived from at least one full or partial epitope of at least one antigen, preferably at least one allergen, determining the specificity of an immune response modulated by such (isolated) recombinant protein, preferably improved MAT (iMAT) molecule (in a subject, preferably an equine)", herein also interchangeably referred to as "antigen module" or "antigen sequence", in the course of the present invention refers to a specific amino acid sequence that allows modulating the immune response against the epitope/antigen and determining the specificity of the immune response in a subject, preferably an equine.

In this context, such antigen module(s) comprise(s) at least one cysteine residue that is substituted with a different amino acid residue, preferably serine, leucine, isoleucine and/or aspartic acid. Thus, the immune response is different compared to the immune response of a subject, preferably an equine, exposed to the unchanged amino acid sequence of the antigen.

There are no restrictions relating to the antigens on the basis of the method. The method can be used for example for activating the immune system of a subject against pathogens such as, for example, against viruses, bacteria, fungi, parasites, protozoa etc., i.e., very generally as a vaccine. Additionally, the method can be used not only directly against such pathogens, but also to activate the host immune system to prevent the transmission in vector-borne diseases involving viruses, bacteria, fungi, parasites, protozoa, etc. In addition, the method can be used to activate the immune system against degenerated cells such as, for example, tumor cells, etc. However, it can also be used on the other hand for desensitization of the immune system of a subject against allergens such as, for example derived from food, mold (fungi and/or their spores), pollen, animal hair, house dust or forage mites (and/or their feces), insect toxins, etc. or for targeted suppression of the immune system, e.g., if autoimmune reactions are present, such as, for example, arthritis, rheumatism, diabetes, SLE (systemic lupus erythematosus), etc., and for suppressing transplant rejection reactions. Further disorders which are not expressly mentioned and which are associated with an immune reaction which is too strong or too weak can likewise be treated with the iMAT molecules, as disclosed and claimed herein.

It is possible to employ as antigen modules for the purposes of the invention in principle all types of antigens able to modulate an immune response. Both, antigens currently already known and antigens to be discovered in future are suitable. In some circumstances, the antigens may also be those which do not lead to an immune response with conventional immunization methods known in the art at present, but which lead on application of the novel method described in the present invention to an immune response by the subject. Further, the term antigen encompasses antigenic fragments comprising the antigenic determinant/the antigenic determinants which are also known as epitope(s). Thus, the antigen module may be the whole molecule, e.g., the protein, or is a part of the molecule, i.e., a fragment thereof, like a peptide, encompassing at least one antigenic determinant or epitope. The at least one antigenic determinant or epitope is able to elicit an immune response against the antigen. The epitope can comprise one or more than one amino acid or peptide or other structure capable of eliciting an immune response such as sugar structures, phosporylated amino acids, etc., or combinations thereof. The antigen can be a continuous epitope (i.e., not dependent on conformation, e.g., present in for example native and denatured proteins) or a discontinuous epitope (i.e., dependent on conformation, e.g., only present in native, folded, but not present in denatured proteins). It is possible to use not only proteins and peptides, but also sugar structures, lipids, e.g., lipopolysaccharides, lipoteichoic acids and other constituents of bacterial membranes (CD1b binds, for example, sugar structures and lipids), nucleic acids such as, for example, DNA comprising CpG motifs, organic substances such as, for example, latex or pharmaceutically active substances as antigen for the purposes of the present invention. The antigen may be derived from all possible life forms, such as e.g. humans, animals, plants, fungi, parasites, unicellular or multicellular microorganisms, viruses and other life forms. The antigens may have been isolated from biological material, have been prepared as recombinant antigens or have been prepared by synthesis, e.g., by peptide synthesis. Synthetically prepared antigens may be substances which occur in nature or which do not occur in nature but are obtainable by chemical synthesis. Examples of non-naturally occurring substances which are, however, suitable as antigen in some circumstances are, for example, synthetically prepared substances which are present in medicaments, or synthetic peptides having amino acid sequences which do not occur in nature, or peptidomimetics, etc. Naturally occurring or synthetic or recombinant antigens can be modified by molecular biology, enzymatic, chemical and/or other methods in order to confer on them properties which are more advantageous for the particular application. These advantageous properties may be, inter alia, a higher or lower activity as antigen, a broader or a more specific action as antigen, a better solubility in hydrophilic or hydrophobic solvents, a greater permeability of the antigen modules for cell membranes, for membranes of organelles, for the blood-brain barrier, for the blood-CSF barrier etc., a higher or lower half-life in vivo or in vitro, a lower or higher toxicity, a better detectability of the antigen in vivo or in vitro after application of the antigen in the form of an iMAT molecule, etc. It is additionally possible for the purposes of the present invention to combine a plurality of antigens in one antigen module. For this it is possible for identical antigens to be present in more than one copy in the antigen module, or it is possible for example for different variants of the same antigen to be combined in an antigen module. Combination of antigens, e.g. of antigen 1, and other antigens, e.g., of antigen 2, in an antigen module is also possible, etc. Further combinations, such as, for example, antigen 1 in more than one copy and antigen 2 in a single copy may also be combined in an antigen module, etc. It is additionally possible also for one or more different and/or one or more identical antigen modules to be present in an iMAT molecule. It is possible in principle for all possible combinations of singly and multiply present identical or altered copies of antigens derived from one or more different antigen to be combined for the purposes of the invention.

In a preferred embodiment, the antigen module comprises at least one full or partial epitope derived from at least one antigen, wherein such antigen is an allergen. At least one epitope is able to elicit an immune response against the allergen whereby the epitope can comprise one or more than one structure, e.g., a peptide, capable of eliciting an immune response. The epitope may be a continuous epitope or a discontinuous epitope of the allergen. Epitopes are preferably at least of eight amino acids in length, preferably are at least ten amino acids in length, and more preferably at least 13 amino acids in length. The antigen module comprises at least one full or partial epitope, but may also comprise two or more full or partial epitopes which may be identical or different from each other. Further, the antigen module may comprise additional amino acid sequences adjacent to the at least one full or partial epitope. The epitope may be the natural occurring epitope or may be a modified epitope, either modified in its amino acid sequence and/or by one or more post translational modifications.

In an embodiment, the at least one third antigen module comprises at least one full or partial epitope derived from at least one antigen of a pathogen involved in one or more infectious disease(s). This could be derived from the genera *rhodococcus, streptococcus, orbivirus, flavivirus, trichophyton, microsporum, cryptosporidium* and/or *strongylus*. The at least one antigen module in the iMAT molecules according to the present invention may also be an antigen of a vector involved in the transmission of one or more infectious disease(s), e.g., *culicoides, culex* and/or *ixodes* saliva components.

In a further preferred embodiment, the at least one third antigen module comprises at least one full or partial epitope derived from at least one allergen eliciting one or more allergy(ies) in equines. This could be at least one full or partial epitope of at least one allergen derived from mold (fungi and/or their spores), pollen, house dust or forage mites (and/or their feces), preferably pollen from tree, grass, herbaceous, *ambrosia* and/or brassicaceae pollen and/or fungi and/or there spores of the genera *aspergillus, alternaria, botrytis, cercospora, cladosporium, curvularia, drechslera, eurotium, helminthosporium, epicoccum, erysiphe/oidium, fusarium, lichtheimia, nigrospora, penicillium, periconia, peronospora, polythrincium, saccharopolyspora* (formerly also *faenia* or *micropolyspora*), *thermoactinomyces, stemphylium, torula* and/or mites (or their feces) of the genera *acarus, glycophagus, tyrophagus, dermatophagoides*

In a preferred embodiment this is, preferably at least one full or partial epitope of at least one allergen derived from blood feeding insects, more preferably from the genus *culicoides*.

Examples of allergens of the genus *culicoides* are shown in FIG. 1 identifying the species, the allergen and the uniprot accession number (database release is UniProt release 2013_09).

In a further preferred embodiment, such at least one allergen is Cul n4, Cul o1, Cul o2, Cul o3, Cul o4 and/or Cul o7 allergen. Preferred specific sequences of the antigen modules are the amino acid sequences according to SEQ ID NOS: 3, 4, 5, 6, 18, 19.

The term "immune response modulated by ( . . . )" or interchangeably "immunomodulatory immune response", in connection with "(isolated) recombinant protein" and/or "iMAT molecule" in the course of the present invention refers to immunogenic and/or tolerogenic immune responses.

The term "allergen" in the course of the present invention refers to a type of antigen that in the native form produces an abnormally vigorous immune response in which the immune system fights off all perceived threats that would otherwise be harmless to the subject. Typically, these kinds of reactions result in the phenotype known as allergy. Various types of allergens are described in the prior art, including foods, drugs, animal products or natural or synthetic material. Preferably, a protein is considered to be an allergen, when it elicits in the native form a specific IgE response in at least five subjects, preferably equines. For the avoidance of doubt, an "allergen" in connection with the "at least one third antigen module comprising at least one full or partial epitope derived from at least one allergen" does not need to be in the native form any longer, which is also preferred—in other words, the term "allergen" in the course of the present invention also explicitly refers to non-native amino acid sequences as part of the iMAT molecules, as described and claimed herein, that do not elicit a specific IgE response in at least five subjects, preferably equines, any longer.

The term "epitope", herein also interchangeably referred to as "antigenic determinant", in the course of the present invention refers to the part of an antigen that is recognized by the immune system, either by B-cells or T-cells. Epitopes are presented on the surface of antigen presenting cells by means of MHC molecules to which they are bound.

The term "subject", herein also interchangeably referred to as "individual" and/or "organism", in the course of the present invention preferably refers to equines.

The term "equine", herein also interchangeably referred to as "horse", in the course of the present invention encompasses any member of the genus *Equus*. It encompasses, e.g., any horse, pony and/or donkey, the taxonomic designations *Equus ferus* and/or *Equus caballus*, and/or the subspecies *Equus ferus caballus*. The equine may, e.g., be a domestic horse.

The terms "peptide" and "protein" are used side by side as equivalent in the course of the present invention. A peptide or a protein means for the purposes of the present invention a covalent connection of at least two amino acids via a peptide linkage. The term "amino acid" and the term "amino acid residue" are used as equivalents in the present application, i.e., the meaning of the two terms is identical. The terms amino acid/amino acid residue and peptide/protein are used in the present application in the form of the widest possible definition.

In this connection, the term "recombinant protein" refers to a polypeptide which may be obtained by genetic engineering and expression in eukaryotic or prokaryotic systems. In addition, said term encompasses polypeptides obtained by artificial (e.g. solid-phase) synthesis.

As used herein, the term "different amino acid residue" refers to a known amino acid residue other than cysteine unless otherwise indicated. For example, said amino acid residue may be a naturally occurring amino acid residue, such as serine or isoleucine.

As used herein, the term "linear form" refers to proteins according to the present invention that lack secondary structure. Such proteins are often assumed to exhibit a random-coil conformation in which the only fixed relationship is the joining of adjacent amino acid residues by a peptide bond.

In a preferred embodiment, the (isolated) recombinant protein as herein disclosed and claimed is present in monomeric form and/or linear form.

As used herein, the term "treatment" refers to the administration of the (isolated) recombinant protein, as disclosed and claimed herein, and/or the corresponding vaccines and/or immunogenic compositions and/or pharmaceutical compositions in order to obtain the desired clinical results including prophylactic and/or therapeutic treatment.

As used herein, the term "immunotherapy" refers to a therapeutic and/or prophylactic treatment of a subject, e.g. by prophylactic and/or therapeutic vaccination.

As used herein, the term "vector" in connection with "transmission of one or more infectious disease(s)" refers to an alive organism and is herein interchangeably used with terms "biological vector", "biological carrier" and/or "disease carrier", such as blood feeding flies, midges, ticks and/or mosquitoes.

Furthermore, it is possible, and preferred, that the (isolated) recombinant protein, as disclosed and claimed herein, contains in addition at least one tag module. That is, it is possible, and preferred, that one or more different and/or identical tag modules are part of the (isolated) recombinant protein, as disclosed and claimed herein. Tag modules may be short peptides, frequently consisting of up to 20 amino acids or functional groups which are not composed of amino acids, such as for example biotin or digoxigenin. Suitable tag modules include the well-known and preferred His-tag containing a histidine sequence of 4 to 12 or more, preferably directly consecutive histidine residues, preferably 5, 6 or 7 consecutive histidine residues. Other suitable tag modules include HA-tag, FLAG-tag, GST-tag or Strep-tag. Although the tag can be present anywhere in the (isolated) recombinant protein, as disclosed and claimed herein, in a preferred embodiment, the tag module is present at the N-terminus and/or at the C-terminus of the (isolated) recombinant protein.

The tag modules are useful for isolating the (isolated) recombinant proteins, as disclosed and claimed herein, and in addition allow detecting the presence of such (isolated) recombinant proteins in vitro or in vivo. Furthermore, the tag module optionally together with one or more adjacent amino acid residues from an adjacent module or a linker spacing apart the different modules can be used in order to induce a specific immunologically detectable signal, (e.g. an antibody) in the target subject that can be used as a surrogate marker for immunity and/or duration of immunity. Immunotherapies with the (isolated) recombinant proteins, as disclosed and claimed herein, elicit an antigen-specific, preferably allergen-specific immune response in the target subjects that is qualitatively indistinguishable from the natural immune response after exposure to naturally existing antigens, preferably allergens. Thus, antibodies binding to the antigen module are not suitable for the purpose of being a surrogate marker for the efficiency of the iMAT induced immune modulatory effect. This obstacle can be eliminated by determining the unique, antigen-specific immunological signal obtained by the C-terminal and/or N-terminal tag module—optionally together with the adjacent amino acid residues. Hence, it is possible to provide suitable surrogate markers accordingly.

In a preferred embodiment, the (isolated) recombinant protein, as disclosed and claimed herein, further comprises at least one tag module, preferably at least one His-tag, wherein such at least one tag module preferably is present N-terminally and/or C-terminally of the (isolated) recombinant protein, more preferably N-terminally after one methionine residue.

Moreover, the modules of the (isolated) recombinant protein, as disclosed and claimed herein, namely, the at least one translocation module, the at least one targeting module and the at least one antigen module may optionally be spaced apart by one or more spacer modules located between at least two of such modules.

The spacer modules may be, in particular, peptide sequences or organic molecules. Numerous spacer molecules which can be used for the purposes of the invention are known in the art. In addition, it is also possible to use spacer molecules which will be developed or discovered in future for the purposes of the invention. Suitable spacer modules are, inter alia, peptide spacers, crosslinkers, natural or synthetic polymers such as, for example, nucleic acids, substituted or unsubstituted hydrocarbons, etc.

The coupling can take place both by covalent (preferred) and by non-covalent linkages. The spacer modules have the task inter alia, of separating the various modules of the (isolated) recombinant protein, as disclosed and claimed herein, from each other in space so that they do not have adverse effects on each other with regard to their functionality. Modules of the (isolated) recombinant protein for the purposes of the invention can be coupled by one or more spacer modules which can be cleaved by chemical and/or enzymatic reactions, e.g., by proteases. It is thus possible to separate the modules of the (isolated) recombinant protein, as disclosed and claimed herein, which are connected by the spacer modules, from each other as required.

In a preferred embodiment, however, in particular if the antigen module is an amino acid sequence derived from at least one full or partial epitope of at least one antigen being at least one allergen, no any such additional spacer modules, i.e., no additional spacer modules between two or more adjacent modules of such first, second and/or third modules at all are present.

Any desired arrangement of the individual modules of the (isolated) recombinant protein, as disclosed and claimed herein, is in general possible. Each module may be present one or more times in the (isolated) recombinant protein. The minimum requirement is the presence of at least one translocation module, at least one targeting module and at least one antigen module. Additional modules, such as tag modules, spacer modules, etc. may optionally be present but do not need to be present. All modules may be present one or more times in the (isolated) recombinant protein, as disclosed and claimed herein. If modules are present more than once, they may be present in the form of identical copies, or different versions of a module may be present in each case in a single copy or in more than one copy. It is also possible for entirely different modules of the same class of modules, e.g., a His-tag module and a biotin-tag module, to be present in the (isolated) recombinant protein, as disclosed and claimed herein. Both modules undertake functionally the same task (tag module) in the (isolated) recombinant protein, but do not need to have anything in common in terms of their molecular structure.

In a preferred embodiment, it is possible that two or more copies of one of the modules are present in the (isolated) recombinant protein, as disclosed and claimed herein. That is, two or more copies of identical or different antigen modules may be present. Alternatively, the (isolated) recombinant protein may contain two different antigen modules, for modulating the immune response in a subject.

Two or more identical copies of an antigen module in a recombinant protein may for example cause an enhanced immune response to such relevant antigen. Two or more different antigen modules may for example be combined in one (isolated) recombinant protein in order to modulate simultaneously the immune response towards two or more different antigens. Two or more different translocation modules can be used in the (isolated) recombinant protein, as disclosed and claimed herein. For example, a Tat sequence and a VP22 sequence can serve to make translocation more efficient since the translocation of the (isolated) recombinant protein then takes place efficiently in a broader spectrum of different cell types or tissue types. It is also possible for example to use two or more tag modules in one (isolated) recombinant protein, e.g., a His-tag and a FLAG-tag, in which case for example the His-tag is used to isolate the recombinant protein and for example the FLAG-tag serves to detect the (isolated) recombinant protein. It is possible to use two or more different targeting modules in one (isolated) recombinant protein, e.g., a sequence from the invariant chain of the MHC II molecule and as a further targeting module, a mannose 6-phosphate group. For example, the invariant chain acts as targeting module into the MIICs, and the mannose 6-phosphate group mediates targeting into the lysosome, thus it being possible to increase the efficiency of antigen presentation or the number of different epitopes of the antigen presented by the antigen-presenting cells overall. In addition, the iMAT molecule of the present invention may encompass two or more different invariant chains stemming from identical or different species, thus, allowing using the proteins according to the present invention in different species.

The position of the individual modules within the (isolated) recombinant proteins, as disclosed and claimed herein, can also be varied as desired, as long as at least one translocation module, at least one targeting module and at least one antigen module are present. It is also possible for all or some of the modules of the (isolated) recombinant protein for example to be present not in the form of a linear sequential arrangement of modules, but as circular or as branched module structure or else in the form of dendrimers, or as a combination of linear and/or branched and/or circular and/or dendrimeric molecule portions. There are commercial suppliers of expression vectors which supply specific vectors which make it possible to prepare circular fusion proteins by these mechanisms, such as, for example, the IMPACT™-TWIN system from New England Biolabs, Beverly, Mass., USA. Branched modules might be prepared for example by synthesizing peptides in which, starting from poly L-lysine, a new lysine residue is attached to both free amino groups of each of the subsequent lysine residues. In this way it is possible to create a peptide structure with virtually any extent of branching. It is then possible to synthesize, for example, translocation modules and/or targeting modules subsequently onto the branched peptide basic structure. Further modules can also be coupled onto a linear, circular or branched peptide basic structure by protein ligation. It is also possible to introduce for example biotin groups into the peptide basic structure during the peptide synthesis, and modules can then be attached to these biotin groups via, for example, streptavidin, the Strep tag system or via the PINPOINT™ system (respectively IBA GmbH, Göttingen, Germany and Promega Biosciences Inc., San Louis Obispo, Calif., USA). Modules attached in this way are then coupled via non-covalent linkages to the peptide's basic structure.

In a preferred embodiment, the (isolated) recombinant protein, as disclosed and claimed herein, comprises, preferably consists of one or more of the amino acid sequences according to SEQ ID NOS: 7, 8, 9, 10, 11, 12, 13, 14, 17, 20, 21, 22, 23.

The (isolated) recombinant proteins, as disclosed and claimed herein, are in particular useful in a method for specifically addressing the therapy and/or prophylaxis in equines suffering from insects bite hypersensitivity (IBH) and/or urticaria.

Insect bite hypersensitivity may be induced by otherwise harmless insect saliva, venom, body parts, excretions or secretions causing systemic responses in subjects. Actually, IBH is a distressing common allergic skin disease of equines and manifest as a chronic relapsing seasonal allergic dermatitis often caused by the bites of insects of the genus *culicoides* found in various areas of the world. IBH has been reported worldwide with different names such as sweet itch, summer itch, summer eczema, Kasen, Queensland itch, seasonal dermatitis or *Culicoides* hypersensitivity. Affected subjects are very itchy and distressed, and rub and bite themselves intensively. A typical clinical sign is pruritus, the fly bites form blisters, which can weep, causing crusting, scabs and scaling. Prolonged rubbing and biting results in, among others, hair loss and damage to the skin, with sometimes bleeding open sores. Occasionally, secondary bacterial infections can occur. It is also not uncommon for horses to rub off their mane and upper tail hair. In the long term, skin thickening and loss of hair pigmentation may occur. The mane and tail are most commonly affected; however, horses with severe signs may have lesions on large areas of the entire body. A diagnosis is based on clinical examination and typical, seasonally occurring signs.

Little is known of the pathophysiology of IBH in horses. There seems to be considerable differences to allergies with manifestation in the skin as compared to other species. Thus, also their response to treatment differs—e.g., histamine receptor antagonists are not able to ameliorate the clinical symptoms (Olsen et al. Vet. J. 2011, 187: 347-351). Also allergen-specific immunotherapy (SIT) has been employed with no success in the past in IBH in horses (Ginel et al., Vet. Derm. 2014, 25: 29-e10).

In order to solve this medical problem the at least one antigen module in an IBH dedicated (isolated) recombinant protein, as disclosed and claimed herein, is selected from a group of recently discovered allergens isolated from midges of different species of the genus *Culicoides* (Diptera: Ceratopogonidae).

Additionally, IBH-affected horses have a 7.1-times increased risk of also suffering from urticaria [Kehrli D et al, J Vet Intern Med 2015, 29(1): 320-326]. Urticaria, also known as 'hives' or as 'nettle rash' is characterized by discrete swellings appearing in the skin. These may be circular patches, ring-shaped lesions, mimic a horseshoe shape or have other unusual shapes. The majority of cases are recurrent, of sudden onset of urticaria and do spontaneously resolve within 24-48 hours or several days.

There is good evidence that there are IgE mediated allergic components involved in urticaria. However, the pathophysiology is still poorly understood. Immediate triggers can be insect stings or bites, dietary, drug reaction, bedding, chemicals, etc., in a predisposed subject, e.g., horses suffering from IBH and/or that are otherwise predisposed for a dermal hypersensitivity to environmental allergens. Thus, successful immunotherapy e.g., against IBH may reduce the occurrence of recurrent urticaria in such subjects.

In a further embodiment the (isolated) recombinant proteins, as disclosed and claimed herein, are in particular useful in a method for specifically addressing the therapy and/or prophylaxis in equines suffering from recurrent airway obstruction (RAO).

Recurrent airway obstruction (RAO) in equines, a respiratory disease similar to human asthma, is one of the most commonly diagnosed conditions affecting the lung of middle aged and older horses all around the world. It is also called heaves, or chronic bronchitis/bronchiolitis, or in earlier days, chronic obstructive pulmonary disease (COPD). When present during summer, e.g., when horses are on pasture, the terms "summer pasture associated obstructive pulmonary disease" or "summer pasture associated RAO" are used.

RAO is a type-1 immediate hypersensitivity allergic disease involving the typical series of events that begin with reaginic antibodies, mainly IgE resulting in mast cell degranulation leading to the production of histamine and other chemical mediators that act together to induce airway inflammation and reversible airway obstruction. The clinical signs observed during exacerbation can be severe and include exercise intolerance, cough, nasal discharge and increased respiratory effort at rest. Diagnostic procedures such as lung function measurement, analysis of blood gas or bronchoalveolar lavage can provide additional information on the disease. Typical treatment involves palliative treatment only (e.g., bronchodilators and/or corticosteroids), but currently no causative treatment is available (Leclere et al. Respirology 2011, 16: 1027-1046, Pirie, Equine Vet J 2014, 46: 276-288).

Recently treatment with a Clara Cell 10 kDa protein (CC10) has been claimed to be effective in protecting or be useful as a passive immunotherapy in horses suffering from RAO. CC10 is one of the members of a family of anti-inflammatory defense proteins produced predominantly in the airway epithelium of man and animals. The invention is described in US 2014/0105906.

RAO is a complex disease, but clearly exposure to airborne allergens plays a pivotal role in the etiology. Clinical remission is usually achieved by eliminating the exposure to the aeroallergens. Though, the major antigens involved in triggering RAO have not been clearly identified so far. Numerous potential agents are present in e.g., organic dust—be it in stabled horses mainly as stable or hay dust or in pastured horses additionally involving pollen (Leclere et al. Respirology 2011, 16: 1027-1046, Pirie, Equine Vet J 2014, 46: 276-288).

The antigen module of iMAT molecules according to the present invention can be selected by a bioinformatics approach as described exemplarily and in detail in Examples 6 and 7 herein. By this means iMAT molecules can be rendered useful specifically as vaccines, e.g., for therapy and/or prevention of RAO in subjects, preferably equines.

In a further embodiment the (isolated) recombinant proteins, as disclosed and claimed herein, are in particular useful in a method for specifically addressing the therapy and/or prophylaxis in equines suffering from infectious diseases caused by bacteria.

*Rhodococcus equi* is a soil-dwelling pathogenic actinomycete that causes pulmonary and extrapulmonary pyogranulomatous infections—equine rhodococcosis. Young foals are particularly susceptible and may develop a life-threatening pneumonic disease. Though, ulcerative enterocolitis, osteomyelitis and septic arthritis are occasionally observed. Many immunization strategies have been tried to prevent rhodococcosis in foals, with no to limited success. Antibiotic treatment is inconsistently effective as well as expensive, and recent studies have highlighted the emergence of antibiotics-resistant strains.

The infection is primarily through inhalation of airborne dust carrying the pathogen. On entry into a host, *R. equi* is taken up by local macrophages, particularly alveolar macrophages in the lung after inhalation. It spreads with slow progressive loss of functional lung, making early clinical diagnosis difficult. Early clinical signs often only consist of a mild fever, occasional cough, or a slight increase in respiratory rate that may not be apparent unless foals are exercised or stressed by handling. Additionally the diagnosis is not that easy—currently a recommended tool for monitoring farms with endemic *R. equi* pneumonia is the analysis of white blood cell concentrations and the cultivation of bacteria from transtracheal washes and identification of *R. equi* via PCR or cytological examinations from such material (van Bargen, K and Haas, A. FEMS Microbiol Rev 2009, 33: 870-891, Vazquez-Boland, J A et al., Vet Microbiol 2013, 167: 9-33).

In order to solve this medical problem the at least one antigen module in an rhodococcosis dedicated (isolated) recombinant protein, as disclosed and claimed herein, may be selected from antigens derived from *R. equi*, e.g., the virulence-associated protein A (VapA), an immunodominant surface-expressed lipoprotein, or other surface proteins, it may also be derived from *R. equi*-infecting phages. Improved MAT molecules may be achieved useful specifically as vaccines, e.g., for therapy and/or prevention of equine rhodococcosis. The treatment may involve the administration of the iMAT molecule to the foal and/or may also comprise a treatment of the pregnant mare according to the present invention.

Strangles is another example of infection in horses, Strangles, characterized by abscessation of the lymph nodes of the head and neck, is caused by *Streptococcus equi* and is one of the most frequently diagnosed infectious diseases of horses and there remains a significant need to develop new preventative vaccines.

In a further embodiment the (isolated) recombinant proteins, as disclosed and claimed herein, are in particular useful in a method for specifically addressing the therapy and/or prophylaxis in equines suffering from infectious diseases caused by viruses.

African horse sickness (AHS) is a highly infectious and deadly disease. It commonly affects horses, mules, and donkeys. It is caused by a virus of the genus Orbivirus belonging to the family Reoviridae. AHS is not directly contagious, but is known to be spread by insect vectors, mainly by *Culicoides*, but also *Culex, Anopheles* and *Aedes*, or transmission by ticks (e.g., *Hyalomma* or *Rhipicephalus*) has been described. To date no effective treatment exists for AHS and close to 90% of the infected horses die mostly due to respiratory failure with 24 h of the infection. Consequently, control of the disease relies on preventive vaccination.

West Nile virus (WNV) is a mosquito-transmitted positive-stranded RNA virus grouped within the Japanese encephalitis virus serocomplex of the genus Flavivirus in the family Flaviviridae. The WNV is the causative agent of the disease syndrome also named West Nile Fever. Birds are the natural reservoir hosts, and WNV is maintained in nature in a mosquito-bird-mosquito transmission cycle. However, when horses are infected it remains frequently unrecognized. Horses have died or are euthanatized because of severe neurologic signs—including paresis, ataxia, recumbency, and muscle fasciculation; others exhibit mild to severe polioencephalomyelitis. Diagnosis and confirmation of WNV infection can be made directly by identification of the virus or indirectly by testing for antibodies in clinical specimens. It is, however, hampered by typically short duration and low level of the viraemia in horses.

In a further embodiment the (isolated) recombinant proteins, as disclosed and claimed herein, are in particular useful in a method for specifically addressing the prevention of transmission of infectious diseases in equines by vectors, e.g., blood feeding flies, midges, ticks and/or mosquitoes.

The pathogens are delivered into the skin of the mammalian host along with arthropod saliva, which contains a wide variety of bioactive molecules. These saliva components are capable of altering hemostasis and immune responses, and may contribute to the ability of the pathogen to establish an infection. The presence of infectious microorganisms in the salivary glands of blood-feeding arthropods itself alters saliva composition, such as changes in the concentration of apyrase or anti-thrombinase in infected mosquitoes. These antigens or others are well suited to be employed in the antigen module of iMAT molecules according to the present invention and may be useful specifically as vaccines to activate the host immune system to prevent the transmission of infectious pathogens by vectors in equines.

In a further embodiment the (isolated) recombinant proteins, as disclosed and claimed herein, are in particular useful in a method for specifically addressing the therapy and/or prophylaxis in equines suffering from infectious diseases caused by fungi.

Dermatophytosis or ringworm is a fungal infection of the hair and of the superficial keratinized cell layers of the skin occurring in animals and man. Several species of genus *Microsporum* or genus *Trichophyton* belonging to the groups of zoophilic or geophilic dermatophytes can cause clinical infections in animals. A variety of surface antigens of the fungi and/or their spores are well suited to be employed in the antigen module of iMAT molecules according to the present invention, and may be useful specifically as vaccines, e.g., for therapy and/or prevention of dermatophytosis in equines.

In a further embodiment the (isolated) recombinant proteins, as disclosed and claimed herein, are in particular useful in a method for specifically addressing the therapy and/or prophylaxis in equines suffering from infectious diseases caused by parasites.

Parasites infecting horses are ubiquitous and clinically important across the world. The major parasitic threats to equine health are *cyathostomins, parascaris equorum, anoplocephala perfoliata*, and *strongylus vulgaris*. Increasing levels of anthelmintic resistance is reported worldwide in equine parasites. For protozoa, e.g., *cryptosporidium* few drugs consistently inhibit parasite reproduction in the host. Mainly foals are affected and outcome relies on innate and adaptive immune responses.

Antigens deriving from adult parasites as well as pre-patent stages are another example to be employed in the antigen module of iMAT molecules according to the present invention and may be useful specifically as vaccines, e.g., for therapy and/or prevention of parasite infection in equines.

In particular in case of modulating the immune response in horses, the at least one targeting module preferably is the equine invariant chain, more preferably one or more amino acid sequences according to SEQ ID NOS: 2, 15, 16.

In an advantageous embodiment, the (isolated) recombinant protein, as disclosed and claimed herein, is present in a monomeric form since, for instance, recombinantly introduced allergens tend to aggregate formation, particularly, if produced via inclusion bodies. By substituting at least one, and more preferably all cysteine residues in the entire sequence of the (isolated) recombinant protein, preferably by substituting for serine, leucine, isoleucine and/or aspartic acid, it is possible to prevent intermolecular disulfide bond formation, thus, avoiding any aggregation, in particular, any non-native formation of inter- and/or intramolecular bonds. That is, the (isolated) recombinant protein being entire devoid of cysteine residues does not aggregate. Consequently, the protein is easily expressible and demonstrates improved targeting and MHC presentation.

Furthermore such cysteine-free variants of, for instance, allergens, in which the cysteine residues in the amino acid sequence of wild-type allergens have been mutated singly or in combinations, show a reduced IgE reactivity compared to the corresponding wild-type allergens and at the same time have substantially retained reactivity towards T-lymphocytes and are thus hypoallergenic.

The invention accordingly relates to such hypoallergenic variants of allergens eliciting for example IBH in horses, wherein in the variants the cysteine residues of wild-type allergens have been mutated singly or in combinations.

Furthermore, the presence of a tag module for separating proteins in a sample, comprising the iMAT molecules according to the present invention, e.g. using zinc- or cobalt-charged solid support further improve the possibility to produce fusion proteins without aggregates during the purification process. Typically, the tag module includes a polyhistidine tag of five to six consecutive histidine residues.

The (isolated) recombinant proteins, as disclosed and claimed herein, are useful in a pharmaceutical composition. For example, the (isolated) recombinant proteins are for use in a vaccine. Hence, the present invention provides vaccine compositions containing one or more (isolated) recombinant proteins, as disclosed and claimed herein. Such vaccine composition can be used therapeutically and/or prophylactically in equines suffering from insect bite hypersensitivity (IBH), urticaria and/or equine recurrent airways obstruction (RAO), infectious diseases induced by pathogens, e.g. rhodoccus pneumonia, strangles, African horse sickness, West Nile Virus infection, dermatophytosis and/or parasites of the digestive tract or other organs, e.g., cryptosporidiosis, helminths and/or their prepatent stages. Additionally, the method can be used not only directed against such pathogens, but also to activate the host immune system to prevent the transmission by vectors, e.g., blood feeding flies, midges, ticks and/or mosquitoes.

Thus, in a preferred embodiment of the present invention a vaccine for subjects, such as equines, is provided in order to treat and/or prevent IBH caused by a response to the bites of e.g. *Culicoides* midges and/or other blood feeding insects. Additionally, successful immunotherapy against IBH may reduce generally the dermal hypersensitivity to environmental allergens and thus may reduce the occurrence of recurrent urticaria in such predisposed subjects.

In a further embodiment of the present invention a vaccine for subjects, such as equines, is provided in order to treat and/or prevent RAO caused by a response to e.g., mold (fungi and/or their spores), pollen, house dust or forage mites (and/or their feces).

In a further embodiment of the present invention a vaccine for subjects, such as equines, is provided in order to treat and/or prevent infectious diseases involving e.g. the genera *rhodococcus, streptococcus*, orbivirus, flavivirus, *trichophyton, microsporum, cryptosporidium* and/or *strongylus*. Additionally, the vaccine can be provided to activate the host immune system to prevent the transmission of a disease by vectors, e.g., *culicoides, culex* and/or *ixodes* and/or other blood feeding insects.

The pharmaceutical composition, e.g., in form of a vaccine, of the (isolated) recombinant proteins is preferably designed for sublingual administration, subcutaneous and/or intradermal injection, injection into a lymph node and/or for administration via the mucous membranes, in particular, via the mucous membranes of the gastrointestinal tract or of the respiratory system.

In a preferred embodiment of the present invention, the pharmaceutical compositions are administered parenterally.

The iMAT molecules according to the present invention can be used as a pharmaceutical or as a vaccine to modify, for instance, allergic disorders. For example, insect bite hypersensitivity (IBH) can be treated by such iMAT molecules.

Low amounts (1 to 1000 μg referring to the weight of solely the one or more antigen modules) of the recombinantly produced iMAT molecules comprising allergens of IBH eliciting insects as of the genus *Culicoides* e.g., injected 1 to 5 times subcutaneously, intradermally or directly into the lymph node, induce a strong and long lasting immune response in horses leading to an amelioration of clinical symptoms.

In one preferred embodiment, the iMAT molecules of the present invention are administered in combination with at least one adjuvant. The adjuvant includes, but is not limited to, one or more of the following: alum, BCG, aluminium hydroxide, aluminium phosphate, calcium phosphate, lipid emulsions, lipid or polymeric nano- or microspheres, micelles, liposomes, saponin, lipid A, or muramyl dipeptide, bacterial products, chemokines, cytokines and hormones, chitosan, starch, alginate, cellulose derivatives (e.g., ethyl cellulose, hydroxypropylmethyl cellulose), nucleic acids, or a nucleic acid construct. One or more of these components may be added to enhance or modify the immune response. Alternatively, the iMAT molecule may be administered without an adjuvant or in an aqueous form.

The iMAT molecules may be administered in a dose of about 1 μg to 1000 μg (this and the subsequent doses referring to the weight of solely the one or more antigen modules) and more preferably in a dose from about 10 μg to about 100 μg and even more preferably in a dose from about 20 μg to about 50 although the optimal dose may vary depending on the antigen, preferably allergen, being injected, the weight of the subject, the immune system of the subject, and alike. Effective treatment in many cases may be accomplished with one administration. In some embodiments, treatment includes from 1 to 15 administrations. In preferred embodiments, treatment includes from 1 to 5 administrations and more preferably 1 to 3 administrations. For initial treatment administrations may be periodically, e.g., over a course of days, once or twice per month or year, or several times a year. For maintenance of immune response, administrations may be done in intervals of several months to several years.

In a preferred embodiment of the present invention, the (isolated) recombinant proteins, as disclosed and claimed herein, are designed for lymphatic intranodal administration. In the course of direct injection into a lymph node, the respective lymph node may be visualized during the injection procedure e.g., by ultrasound, in order to monitor the location of the needle and changes in the lymph node, such as swelling. Injection into the mandibular, axillary, inguinal and/or popliteus lymph nodes is preferred due to ease of ultrasound guided location and injection.

It is known in the art that several (>20) of the identified proteins in saliva of blood feeding insects induce IgE reactivity and pathological dermal reactions in horses [Schaffartzik, Veterinary Immunology and Immunopathology 2012, 147: 113-126; Allergome (allergome.org)]. Thus, it is expected that a treatment can only be successful, if most of the relevant allergens are included in a medicament for specific immunotherapy. However, surprisingly only 1, 2, 3 or 4 of such iMAT molecules according to the present invention each comprising different antigen modules e.g., of insect saliva or a mosaic-like construct of only epitopes are sufficient to induce an immunomodulation and/or clinical improvement of the diseased subjects if such iMAT molecules are injected 1 to 5 times subcutaneously, intradermally and/or directly into the lymph node.

In a preferred embodiment, a single iMAT molecule is employed and is sufficient for the induction of a therapeutic effect and/or prevention of development of insect bite hypersensitivity (IBH), urticaria and/or equine recurrent airways obstruction (RAO) in equines.

In another preferred embodiment, a combination of 2, 3 or 4 iMAT molecules is employed by means of simultaneous, sequential and/or a chronologically staggered co-administrations.

In a preferred embodiment, a single iMAT molecule is employed and is sufficient for the induction of a therapeutic effect and/or prevention and/or prevention of transmission of infectious diseases in equines e.g., rhodoccus pneumonia, strangles, African horse sickness, West Nile Virus infection, dermatophytosis and/or parasites of the digestive tract or other organs, e.g., cryptosporidiosis, helminths and/or their prepatent stages and/or the transmission of such infectious diseases by e.g., blood feeding flies, midges, ticks and/or mosquitoes.

In another preferred embodiment, a combination of 2, 3 or 4 iMAT molecules is employed by means of simultaneous, sequential and/or a chronologically staggered co-administrations.

Depending on the thermodynamic evaluation of the (isolated) recombinant protein, as herein disclosed and claimed, stability is influenced by the cysteine mutation, namely the substituting different amino acid residue(s). For example, the substitution may be a Cys to Ser substitution. However, the stability may be higher using a different amino acid residue than the Ser amino acid to achieve the desired stability and solubility. That is, while a first choice may be substitution of Cys with Ser, in case of instability, other amino acid residues than Ser should replace Cys.

In order to select stabilizing amino acid residues as replacements for cysteine residues in targeted sequences a three step approach is chosen:
1. Modeling the tertiary structure of the targeted protein including terminal hexahistidine tags, iMAT sequence and the primary amino acid sequence of the protein of interest. Modeling can be conducted with the native sequence and with cysteine substitutions.
2. Iterative determination of protein stabilities based on single point substitutions, such as substitution of a cysteine residue with a different amino acid residue, e.g., Ser and/or Be, and scoring to determine stabilizing replacements by analyzing all available three dimensional structures.
3. Re-Modeling of the stabilized structure and validation of the stability by repeating step 1 and 2.

Three-dimensional protein structures are crucial for understanding protein function on a molecular level and are of great interest for the rational design of many different types of biological experiments, such as site-directed mutagenesis. However, the number of structurally characterized proteins is small compared to the number of known protein sequences. It is possible to identify a homologous protein with a known structure (template) for a given protein sequence (target). In these cases, homology modeling has proven to be the method of choice to generate a reliable 3D model of a protein from its primary amino acid sequence. Building a homology model comprises four main steps: (1) identification of structural template(s), (2) alignment of target sequence and template structure(s), (3) model building and (4) model quality evaluation. These steps can be repeated until a satisfying modeling result is achieved. In cases where no accurate homologue model can be determined, computational approaches to determine a protein structure from the primary structure (amino acid sequences) are used. "De novo" or "ab initio" methods are based on physical principles and try to imitate the folding process. Such methods have to sample a large number of conformations and require very accurate energy functions to identify structures in the global minima of free energy. Many methods use a combination of these described principles.

The availability of computational tools yielding reasonably accurate estimations of the impact of amino acid substitutions on the stability of proteins is of crucial importance in a wide range of applications. In particular, such tools have the potential of stimulating and supporting protein engineering and design projects dedicated to the creation of modified proteins.

Protein stability can be regarded in terms of the thermodynamic stability of a protein that unfolds and refolds rapidly, reversibly. In these cases, the stability of the protein is the difference in Gibbs free energy between the folded and the unfolded states. The only factors affecting stability are the relative free energies of the folded and the unfolded states. The larger and more positive the folding free energy difference is, the more stable the protein is to denaturation. The folding free energy difference is typically small, of the order of 5-15 kcal/mol for a globular protein. However, on the other hand, protein stability can be regarded as a protein property to withstand harsh temperature or solvent conditions. This is related to the thermodynamic stability but also to reversibility or irreversibly of folding/unfolding (kinetic stability).

To predict the thermodynamic stability changes caused by single site substitutions in proteins, several different approaches can be applied to study the impacts of such substitutions on protein structure and function [Pires D E et al., Bioinformatics 2014, 30(3):335-342]. Such approaches can be broadly classified into those that seek to understand the effects of substitutions from the amino acid sequence of a protein alone, and those that exploit the extensive structural information. Structure-based approaches typically attempt to predict either the direction of change in protein stability on substitutions or the actual free energy value ($\Delta\Delta G$).

The results for each specific protein and its corresponding models are statistically analyzed in terms of the number of appearances of specific substitutions using a scoring system, that grades the replacement based on occurrences in used models and the protein stability free energy change ($\Delta\Delta G$) thereby determining most destabilizing residues (if any) within the input structure and possible replacements. The score is calculated by determination of the lowest $\Delta\Delta G$ ($\Delta\Delta G<0$) at each position of interest in each model and assigning corresponding linear values and cumulative $\Delta\Delta G$'s values for each potential replacement position and results are than evaluated to determine consistency among models. Since calculated protein models possess different qualities (the probability of predicting the correct three-dimensional structure) a weighting factor can be implemented to prioritize results from more accurate models. A significant (based on the $\Delta\Delta G$) destabilizing residue (if any) is substituted; new models are generated and re-analyzed iteratively until a steady state is reached. Additionally generated models are evaluated by analyzing the xyz coordinates via principal component analysis to determine potential structural misfoldings due to replacement of amino acids at specific positions.

In yet a further aspect, the objective underlying the invention has surprisingly been solved by providing a method of identifying amino acid substitutions in a predetermined amino acid sequence allowing the stabilization of such predetermined amino acid sequence comprising the steps of:

i. modeling of the three-dimensional/tertiary structure of the targeted predetermined amino acid sequence,
ii. iterative determination of protein stabilities based on single point substitutions, such as substitutions of cysteine residues with different amino acid residues, preferably serine and/or isoleucine residues, and a scoring system based on the protein stability free energy changes ($\Delta\Delta G$) to determine stabilizing substitutions by analyzing all available three-dimensional/tertiary amino acid sequence structures,
iii. re-modeling of the substituted three-dimensional/tertiary amino acid sequence structure and calculation of its stability by repeating steps (ii) and (iii) until a steady state is reached;

In yet a further aspect, the objective underlying the invention has surprisingly been solved by providing an (isolated) recombinant protein as herein disclosed and claimed, wherein its full or partial amino acid sequence was stabilized by the method of identifying amino acid substitutions in a predetermined amino acid sequence as herein disclosed and claimed (see Example 5 herein).

BRIEF DESCRIPTION OF THE FIGURES

FIG. 1: shows examples of allergens of the genus *culicoides* identifying the species, the allergen and the uniprot accession number (database release is UniProt release 2013_09)

FIGS. 2A and 2B show an SDS-PAGE of MAT-Fel d1 (IVN201) under reducing conditions; FIG. 2A) Original SDS-PAGE (10 μg protein per lane, Coomassie staining) and FIG. 2B) SDS-PAGE with bands that have been cut out of gel A and reloaded on SDS-PAGE (silver staining)

FIG. 3: shows an SDS-PAGE of Fel d1 under reducing conditions; NUPAGE® 4-12% Bis-Tris Gel. Lanes: 1) Marker: SeeBlue Plus2 Pre-Stained Standard 2) 5 μg Fel d1; 3) 5 μg Fel d1

FIG. 4: shows an RP-HPLC chromatogram 0.1% TFA/Acetonitril gradient a) native protein (MAT-Fel d1) without additives (left graph); b) MAT-Fel d1 denaturated by addition of guanidinium chloride plus DTT (right graph)

FIG. 5: depicts MAT-Fel d1 molecule and its Kyte-Doolittle hydrophobicity plot FIG. 6: shows a NUPAGE® SDS-PAGE-System (4-12% Bis-Tris Gels, 1×MES-Running buffer, 35 min, 200 V). Lanes: 1) Lysozyme, 1 μg Protein ox. 2) PageRuler Prestained Protein Ladder; 3) MAT-Fel d1 (5 μg) oxidized with Iodacetamide (ox.); 4) iMAT-Cul o4 (ox.); 5) PageRuler Prestained Protein Ladder; 6) MAT-Fel d1 (5 μg) reduced; 7) iMAT-Cul o4 reduced; 8) Lysozyme reduced FIG. 7: shows an RP-HPLC chromatogram 0.1% TFA/Acetonitril gradient. The peak reflects native (oxidized) protein (iMAT-Cul o4) without additives FIG. 8: depicts an example of display of counts of local alignments hits of selected *Culicoides* allergens in comparison to sensitizations measured (see description for details). The figure depicts the comparison between the antigenic prediction (light gray and right Y-axis) and the outcome (dark gray and left Y-axis) in a HRT test in terms of severity (total score values per allergen) in a cohort of IBH horses. The severity describes the degree of a reaction in the test in a semi-quantitative scale (left Y axis). The data from the prediction is scaled by setting the highest occurrence score equal to the highest severity score.

Figure 9:
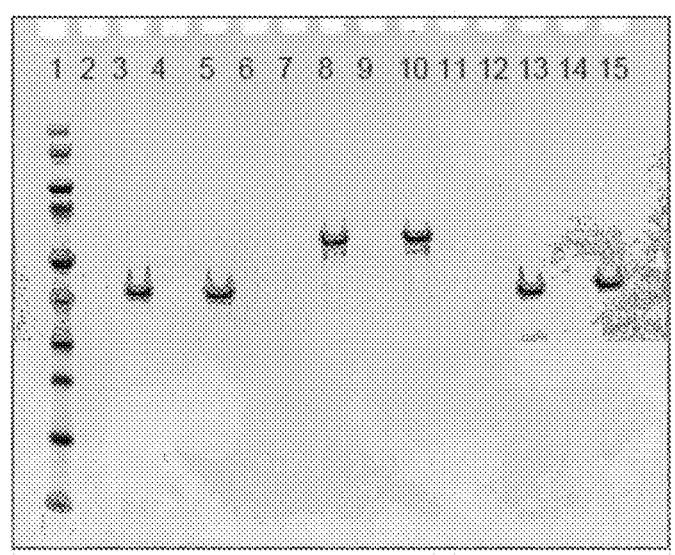

FIG. 9: shows the results of the following experiment: Proteins and ADJU-PHOS® that were incubated at RT for 30 min while mixing gently. After incubation, the samples were centrifuged for 3 min. and subsequently analyzed by SDS-Page Lane 1) pageRuler Prestained Protein Ladder; 2) iMAT-Cul o3 Supernatant; 3) iMAT-Cul o3 Pellet in Urea 4) iMAT-Cul o3 Supernatant; 5) iMAT-Cul o3 Pellet in Urea; 6) Empty; 7) iMAT-Cul o2 Supernatant 8) iMAT-Cul o2 Pellet in Urea 9) iMAT-Cul o2 Supernatant 10) iMAT-Cul o2 Pellet in Urea; 11) Empty; 12) iMAT-Cul o4 Supernatant; 13) iMAT-Cul o4 Pellet in Urea 14) iMAT-Cul o4 Supernatant; 15) iMAT-Cul o4 Pellet in Urea; (2, 3, 7, 8, 12, 13 w/o freeze thaw); (4, 5, 9, 10, 14, 15 after two times freeze thaw process)

Figure 10:
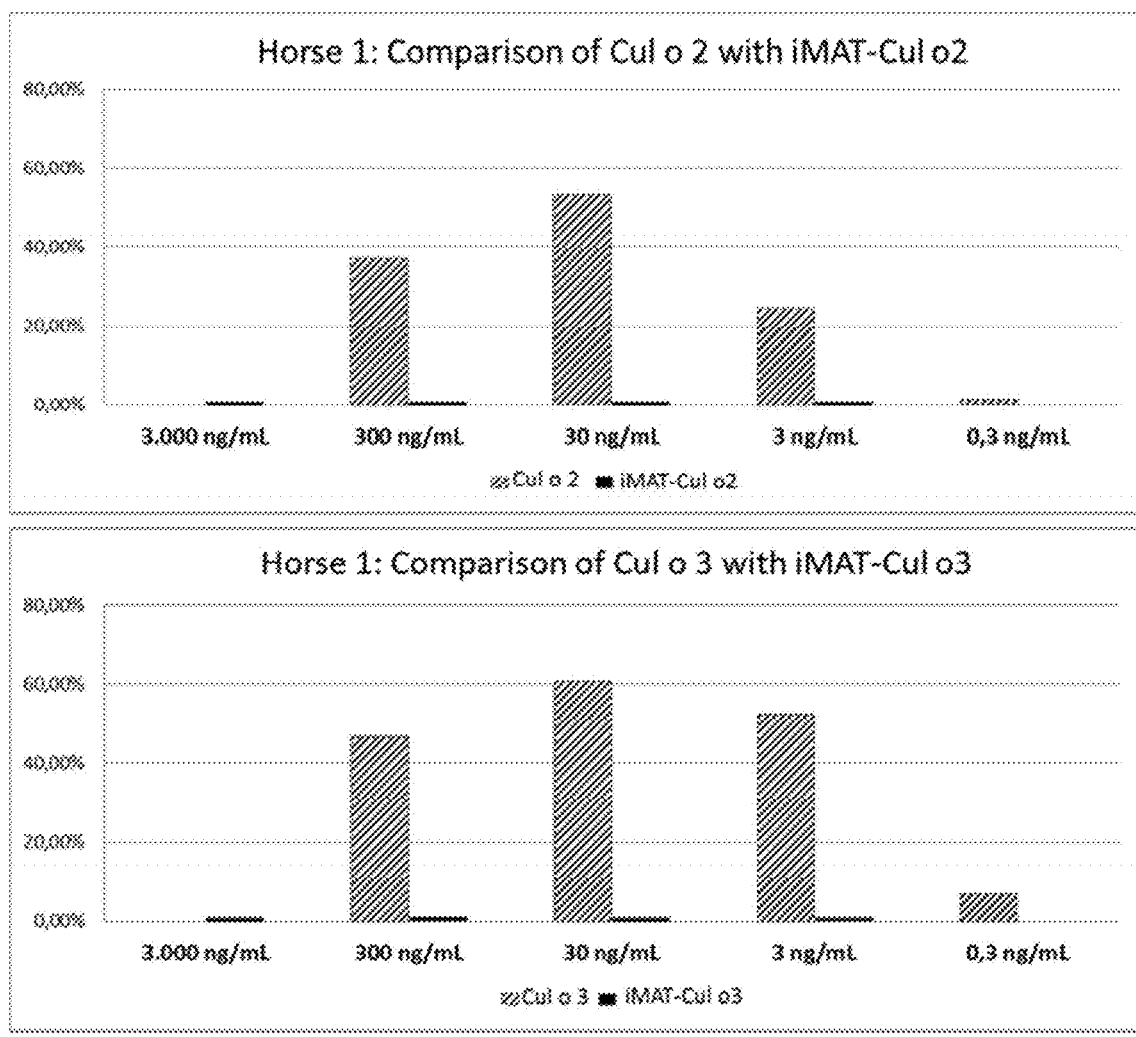

FIG. 10: shows Histamine Release Test (Details of assay in Example 2) of 5 concentrations of iMAT-Cul o2 and iMAT-Cul o3 and the respective allergens in a polysensitized horse (Horse 1)

Figure 11:
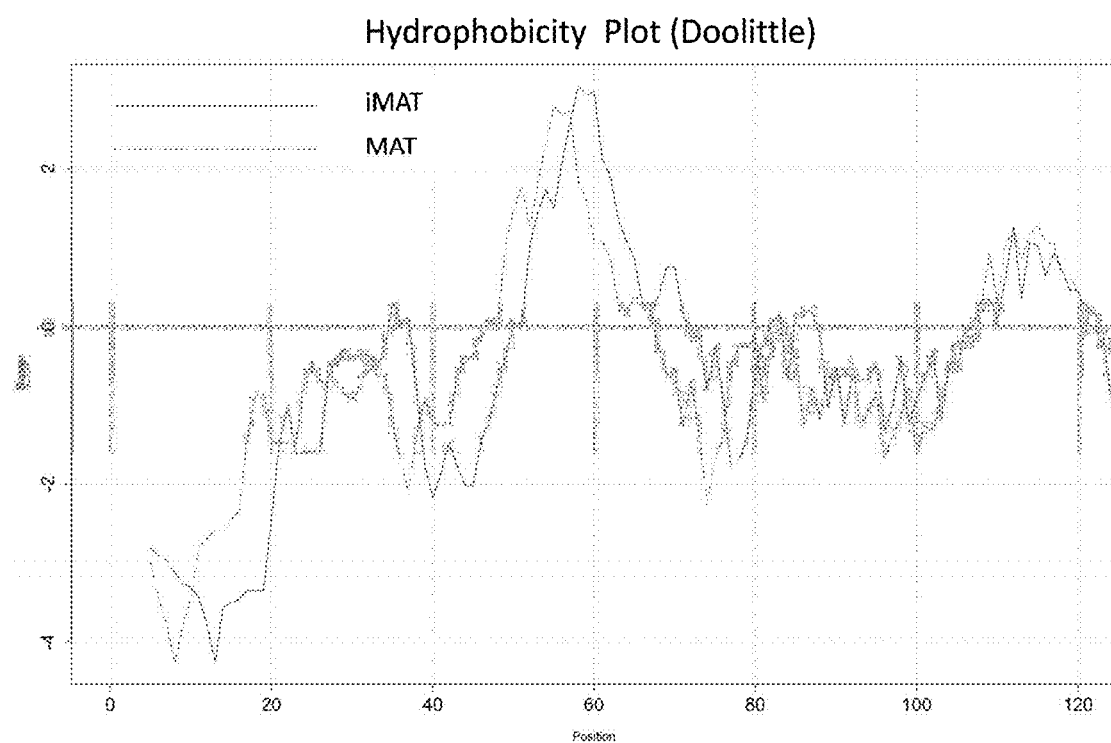

FIG. 11: shows the Kyte-Doolittle hydrophobicity plot of MAT molecules versus iMAT molecules in the generic part of the respective fusion proteins [i.e. without the respective antigen module(s)]. The hydrophobicity index is shown on the Y-axis versus the amino acid position on the X-axis. Positive numbers in the index indicate hydrophobicity. The shift of the graph of the iMAT molecule at the beginning of the hydrophobicity plot as compared to the MAT molecule is due to the additional N-terminal presence of a His-tag and one methionine residue in the iMAT molecule as well as the absence of any spacer module(s).

Figure 12:
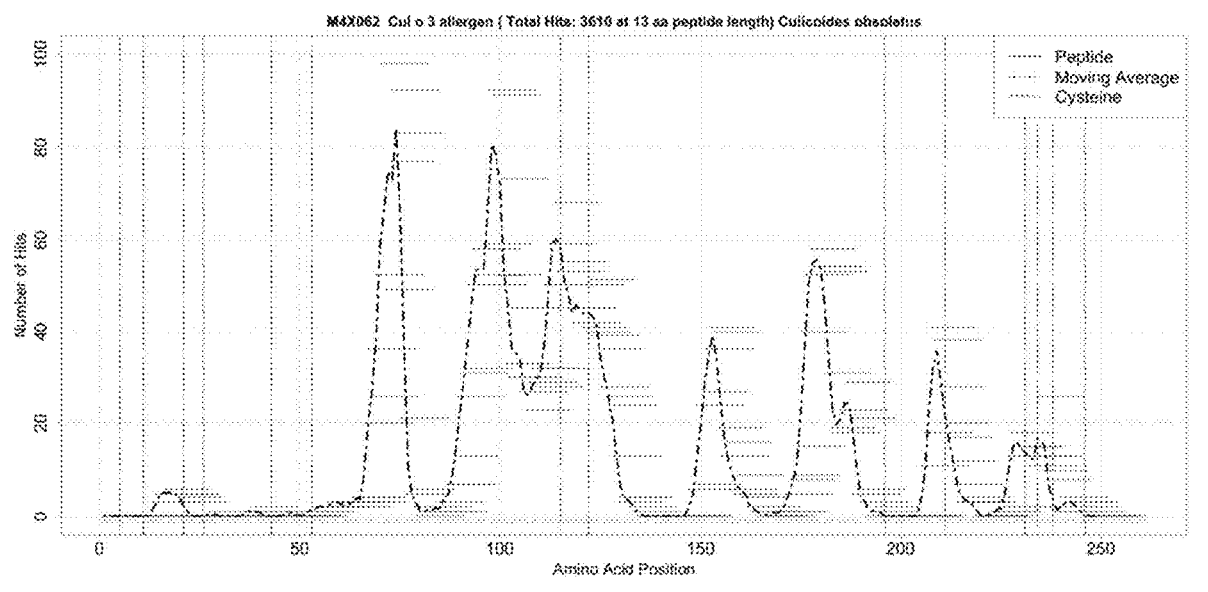

FIG. 12: shows the number of non-random hits for each peptide with a length of 13 amino acids for Cul o3 (M4X062, SEQ ID NO: 6) in the canonical database and their position within the corresponding precursor protein. The y-axis depicts the number of hits and the x-axis the amino acid position in reference to the precursor protein. Vertical dotted lines indicate cysteine residues, the dotted-dashed line depicts the moving average of the number of non-random found homologies and horizontal solid lines correspond to in silico cleaved peptides.

EXAMPLES

The following examples serve to further illustrate the present invention; but the same should not be construed as a limitation of the scope of the invention disclosed herein.

Example 1—Surrogate Marker for Immunity/Duration of Immunity

Administration of an (isolated) recombinant protein, as disclosed and claimed herein, to an equine produces an immunological response to the allergen and/or epitope present in the antigen module. Additionally, the C- or N-terminal tag module together with the adjacent amino acid residues from the adjacent module can be used in order to detect a unique product-specific immunological signal (e.g. an antibody—or a T-cell response) in a target subject that can be used as a surrogate marker for immunity or duration of immunity. This surrogate marker, as a treatment-specific immunological parameter, enables the assessment of immunity or immune modulation or the duration of immunity or the duration of immune modulation after the administration. Thus, a specific indicator for an immune response triggered by the (isolated) recombinant protein according to the invention is the induction of terminal-tag (optionally with the adjacent amino acid residues) specific antibodies, such as IgG antibodies. Alternatively or additionally, the indicator is the induction of antibodies specific to the junction of a spacer and a module as described and claimed herein or the junction between two modules.

Example 2—Hypoallergenicity

Freshly withdrawn blood of horses suffering from IBH can be prepared to test the basophil reactivity to (isolated) recombinant proteins/iMAT molecules, as disclosed and claimed herein. This can be determined by a modified method of Kaul [Kaul, S., 1998. Type I allergies in the horse: Basic development of a histamine release test (HRT). Doctoral thesis. Veterinary School Hannover, Germany]. Briefly, a 10-fold dilution series (e.g. ranging from 10 nM to 0.001 nM final allergen concentration) of iMAT molecules and/or recombinant allergens is prepared in PIPES buffer (AppliChem, Darmstadt, Germany), pH 7.4. Washed red and white blood cells obtained from Na-EDTA coagulation-inhibited blood are incubated with individual dilutions for 1 h at 37° C. The reaction is stopped by incubation on ice for 20 min and the supernatant containing the released histamine is collected from each sample after centrifugation. Maximal histamine content is obtained by boiling the blood cells for 10 min in a water bath (maximal release). The incubation of releasing buffer with washed blood cells served as a negative control (spontaneous release). Histamine concentrations are determined using a competitive RIA (LDN Nordhorn, Germany) as per the manufacturer's instructions.

Alternatively, another basophil activation test is the Cellular Antigen Stimulation Test CAST® ELISA which can also be considered as an in vitro allergy provocation test. This assay is done according to the manufacturer's instructions (Bühlmann Laboratories AG, Allschwil, Switzerland). In the CAST®, sedimented leukocytes from allergic subjects' blood are simultaneously primed with the cytokine IL-3 and stimulated with iMAT molecules and/or recombinant allergens. Basophilic cells among others generate the allergic mediator, sulfidoleukotriene LTC4, and its metabolites LTD4 and LTE4. These freshly synthesized sulfidoleukotrienes (sLT) are subsequently measured in an ELISA test (Enzyme Linked Immunosorbent Assay).

The potential of iMAT molecules to induce adverse events, e.g., provoke anaphylaxis as a side effect of administration can be evaluated in vitro with these assays by comparing the effects of the iMAT molecules (containing an allergen) to the respective recombinant allergen alone.

A reduced basophil degranulation, e.g., histamine and/or sulfidoleukotriene release by iMAT molecules as compared to the recombinant allergen indicates a lower potential for adverse effects, i.e., a better safety profile of the iMAT molecules.

Said HRT (or CAST®) can be used as an in vitro provocation test for type 1 allergic reactions in horses. Allergen specific histamine release indicates the relevance of the respective allergen for the basophilic cell activation and thus can be used as a quantitative parameter for the allergen specific sensitization of a subject.

With MAT molecules described in the prior art, hypoallergenicity could be demonstrated in comparison to the corresponding native allergen (Fel d1) [Senti G et al., J Allergy Clin Immunol. 2012, 129(5): 1290-1296] in the Cellular Antigen Stimulation Test (CAST®) assay as well as in the intradermal and in the intracutaneous test. The quantitative difference in sensitivity between the allergen and the MAT molecule comprising the Fel d1 was 100-, 23- and 16-fold, respectively. Though MAT-Fel d1 was clearly hypoallergenic, some allergenicity remained.

With regard to the present invention, the safety of 2 iMAT molecules manufactured according to the present invention comprising Cul o2 and Cul o3 in the antigen module, respectively, was tested. Freshly withdrawn blood of a poly-sensitized horse suffering from IBH was employed in the histamine release test (HRT) as described above.

As shown in FIG. 10, the native allergens elicited a strong histamine release whereas surprisingly the two different iMAT molecules (iMAT-Cul o3 and iMAT-Cul o2) showed virtually no response at all.

Thus, iMAT molecules showed clear superiority in respect to safety as compared with the MAT molecule as described in the prior art (see above).

It can be expected that no allergen related adverse reactions occur if horses suffering from IBH are treated with said iMAT molecules.

The consequence of this surprising safety property of iMAT molecules in contrast to MAT molecules is, that iMAT molecules used as desensitizing proteins can be used similar to vaccines against pathogens. No up-dosing as with classical therapeutic allergens is needed, since vaccines comprising iMAT molecules do not show allergen properties with respect to allergic adverse events. Already the dose of the first injection of the iMAT molecule in a treatment course may be selected based on efficacy considerations only, and one does not have to consider potential allergic adverse reactions. This could not be performed using MAT molecules described in the prior art since the allergenicity of MAT, compared to the native allergen, was only reduced to a certain level. However, MAT molecules still are allergens; iMAT molecules, in contrast, are not. The advantage of these improved properties renders a more efficacious treatment regime possible with e.g., three subcutaneous or intralymphatic injections with a high biopharmaceutical content (e.g., 3 times 20 µg to 50 µg iMAT protein).

The lack of allergenicity of the two iMAT molecules tested can be explained by the fact that in contrast to the MAT molecules described in the prior art no linker amino acid residues [i.e. spacer module(s) between the first, second and/or third module(s)] were used to separate the different modules in such iMAT molecules. It is known in the prior art that engineered fusion proteins containing two or more functional polypeptides joined by a peptide or protein linker are important for the function (e.g. epitope recognition by the immune system) of the proteins [Klein J S et al., Protein Eng Des Sel. 2014, 27(10): 325-330]. The separation distance between functional units can impact epitope access and the ability to bind with avidity. If the missing amino acid residue linkers between the modules, in particular between the targeting domain and the antigen module, lead to a more rigid structure, conformational epitopes of the allergen module might not be formed due to incorrect folding. A cross linking of antibodies bound on the surface of basophils (e.g., IgE) by its high affinity receptors is necessary to induce activation and histamine release. However, misfolded allergens might not be able to induce such cross linking. Thus, an iMAT molecule without linker may not form conformational IgE epitopes which renders the iMAT molecules non-allergenic.

Example 3—in Silica Detection of Allergens/Biomarkers

As described in detail in the description of the invention in IBH the major allergens eliciting IBH have not yet been described—the bioinformatical engineering of iMAT antigen modules for targeting IBH may be employed to evaluate in silico the relevance of a certain allergens (see Example 6 herein). For example, as shown in FIG. 8 the in silico as well as the ex vivo functional HRT test results of Cul o3 seem to indicate that Cul o3 is a major allergen. Most of the horses tested, though not all, showed a clear hypersensitivity against Cul o3.

This is surprising, as in other experiments, e.g., by van der Meide et al. (Vet J 2014, 200: 31-37), the different recombinant allergens could not be discriminated in their relevance for the disease: around 80% to 90% of horses suffering from IBH showed a sensitization to each of the allergens tested.

Thus, surprisingly, in the course of the present invention it could be shown that Cul o3 (i) in fact is a major allergen (i.e. >50% of the animals are sensitized) in IBH and (ii) is of superior relevance as compared to other allergens.

Apart from being employed in the iMAT antigen module, the respective allergens can also serve to optimize the treatment success by investigating prior to initiation of the treatment the strength of hypersensitivity against said allergen. And throughout the course of the treatment the allergen specific modulation of the different components of the immune system can be monitored, e.g., changes in allergen specific IgE and IgG antibody titers can indicate therapy and/or prevention effects.

Thus, the in silico detected allergens and/or the respective allergen-specific immunoglobulins may be employed as diagnostic and/or theranostic biomarkers.

Example 4—Therapeutic Vaccine/Prophylaxis of IBH in Equines

A single iMAT molecule or a combination of iMAT molecules containing different antigen modules according to the present invention may be employed for treating prophylactically or therapeutically a horse suffering from or to be at risk of insect bites inducing IBH. In horses, iMAT molecules according to the present invention can be administered into a submandibular lymph node (Landholt et al., Vet Rec 2010, 167: 302-304). Briefly, the hair over the lymph node is clipped and surgically prepared. Using palpation and/or ultrasound for guidance, a 25 G needle is inserted into the lymph node. The injected iMAT molecule is adsorbed to an adjuvant. The adjuvant consists e.g., of aluminum phosphate (ADJU-PHOS®, Brenntag Biosector, Denmark). The iMAT molecule stock is a frozen solution of 375 μg/mL protein concentration in vials, each containing 500 μL to be thawed before use.

After thawing the iMAT molecule solution, 400 μL of the solution are mixed with e.g., 200 μL of the aluminum phosphate gel suspension. This final formulation is left at room temperature for 60 minutes prior to the intralymphatic injection to allow for absorption of the iMAT molecule to the ADJU-PHOS®. e.g., 200 μL of the mixture containing 50 μg iMAT molecule is removed into a 500 μL syringe for lymph node injection. This preparation is first administered typically on day 0, day 28 and day 56 in a dose between 20 μg and 50 μg (referring to the weight of solely the one or more antigen modules) per injection and iMAT molecule.

Throughout the treatment period and/or thereafter the efficacy of a therapy or the prevention of IBH can be investigated clinically by quantitative, semi-quantitative or qualitative assessment of skin lesions (e.g., broken hairs, alopecia, crusts/scrubs and wet areas). The intensity of scrubbing/itching can be scored.

These clinical parameters can be compared to clinical signs of the individual horse in previous IBH seasons and/or to the severity prior to the start of a therapeutic intervention. Alternatively, a comparison to IBH affected horses that are not treated or treated with placebo can demonstrate the efficacy of the iMAT molecule-mediated treatment and/or prevention of clinical signs of IBH.

Fresh blood of said horses can be used in an in vitro provocation test for type 1 allergic reactions in horses, e.g., with HRT or CAST® (for details see Example 3 supra). A reduced basophil degranulation in response to a challenge with certain *culicoides* allergens, e.g., histamine and/or sulfidoleukotriene release after the iMAT molecule administration, as compared to before, indicate a therapy and/or prevention effect.

Alternatively or in addition an intradermal provocation test [Langner et al., Vet Immunol Immunopathol 2008, 122(1-2):126-37] with certain *culicoides* allergens can be employed in said horses. A reduced response (immediate and/or late phase reactivity) indicates a therapy and/or prevention effect of the iMAT molecule administration.

Furthermore, the modulation of the different components of the immune system can be monitored, e.g., changes in allergen specific IgE and IgG antibody titers can indicate therapy and/or prevention effects.

Apart from changes in IgE levels, an increase in allergen-specific IgG can be surprisingly found when treating a horse for IBH with such iMAT molecules. These antibodies can block IgE-mediated anaphylaxis in vivo and seem to inhibit not only the allergen-induced release of inflammatory mediators from basophils and mast cells, but also IgE-mediated allergen presentation to T cells. Among the iMAT-induced IgG antibodies specifically binding to the allergen, some allergen-specific subtypes have been suggested to play an important "protective" role, as they compete with allergen-specific IgE antibodies and can prevent the activation of CD4+ T cells, by inhibiting the IgE-mediated antigen presentation. Furthermore, the IgG subset which is secreted promotes a significant reduction in mast cells and eosinophils, accompanied by a diminished release of inflammatory mediators [Senna G et al., Curr Opin Allergy Clin Immunol. 2011, 11(4): 375-380].

The functional assay of serum "blocking" IgG activity as determined by suppression of FcεRI-dependent basophil histamine release [Niederberger V et al., Proc Natl Acad Sci USA 2004, 101: 14677-14682] and/or inhibition of FcεRII (CD23)-dependent binding of IgE-allergen complexes to B cells seems to offer a better prediction of the individual clinical response (Wacholz P A et al., J Allergy Clin Immunol 2003; 112: 915-922).

Allergen-specific immunotherapy can modulate different components of the immune system. Cellular modifications consist of a reduction in allergen-induced T-cell proliferation, indicating the induction of peripheral tolerance in allergen-specific T cells and a decrease in antigen-specific Th2-dominated immune response in favor of a Th1 reaction with increased IFN-γ production (Durham S R et al., J Allergy Clin Immunol 1996, 97: 1356-1365). The key cell type responsible for coordinating this immunological switch is a heterogeneous T-cell population, called regulatory T cells ($T_{reg}$). At the cellular level, the crucial factor for successful allergen immunotherapy is the peripheral induction of type 1 $T_{reg}$ cells. Functional studies on type 1 $T_{reg}$ cells, specific in recognizing antigens, revealed that the modulation of Th1 and Th2 responses by type 1 $T_{reg}$ cells mostly depends on the secretion of the cytokine IL-10, which has immunosuppressive properties. In fact, IL-10 inhibits the proliferative response of peripheral T cells against specific allergens and plays a central role in the induction of T-cell anergy (James L K, Durham S R, Clin Exp Allergy 2008, 38: 1074-1088). In vitro, IL-10 enhances the expression of the regulatory factor FoxP3, modulates eosinophilic function and reduces pro-inflammatory mediators released by mast cells (Mobs C, et al., Int Arch Allergy Immunol 2008, 147: 171-178).

Another possible marker of the outstanding clinical efficacy of said iMAT molecules-mediated immunotherapy is the detection of changes in the number or the nature of allergen-specific T cells. On the basis of, for example, Bet v1 tetramer staining studies, the levels and characteristics of circulating birch pollen-specific CD4+ T cells can potentially be compared before and after SIT (van Overtvelt L et. al., J Immunol 2008, 180: 4514-4522). Recently, transforming growth factor (TGF)-β has also been identified as a key cytokine in successful SIT. Many actions may account for its relevance, such as the suppression of specific Th1, Th2 and Th17 cells, the induction of FoxP3 and the suppressive function of Tregs. In addition, TGF-β down regulates FcεRI expression on Langherhans cells and suppresses IgE synthesis (Akdis C A, Akdis M J, Allergy Clin Immunol 2009, 123: 735-746).

Example 5—Comparison of iMAT Molecules According to the Present Invention with Prior Art MAT Molecules According to WO 2004/035793 (US Equivalent US 2005/0281816)

Figure 2B:
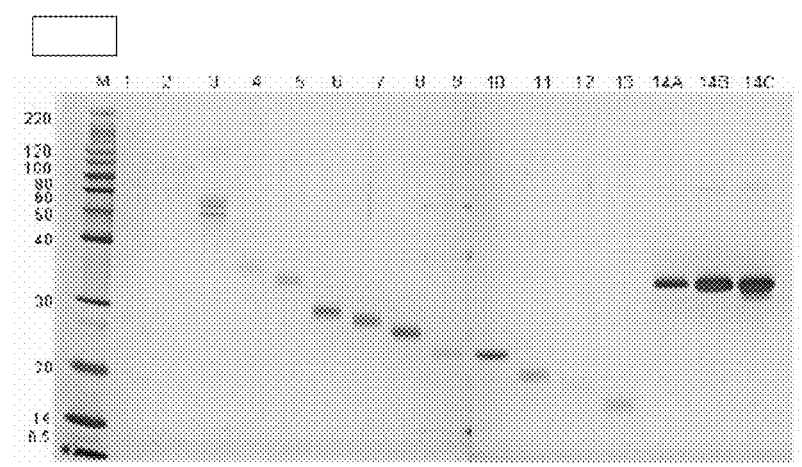

For assessment of purity of a MAT protein, a sodium dodecyl sulfate-polyacrylamide gel electrophoresis (SDS-PAGE) test procedure has been established (Thompson J et al., J Biol Chem 2002, 277: 34310-34331). The method, including sample preparation with a reducing agent, Lithium Dodecylsulfate (LDS) and heating at 75° C., resulted in reproducible multiple sharp bands after electrophoretic separation. Staining with Coomassie blue gives linear quantitative (densitometry) features in gels loaded with 200 to 1000 μg protein. Using a monoclonal antibody, detecting the allergen module in a MAT molecule with Fel d 1 as allergen module (MAT-Fel d1) it has been shown, that the main band and 13 minor bands all contain the MAT-Fel d1 protein. The small bands migrate at the same position as on the original gel also after re-loading on the gel (FIGS. 2A and 2B). Several different methods, such as different temperature and buffer composition protocols, for sample preparation prior to PAGE generated the same band pattern.

In all of these bands the presence of the full length (complete) MAT-Fel d1 protein and only traces of host cell proteins could be demonstrated after each band was cut out of the gel, digested by trypsin and subsequently analyzed by mass spectrometry (nanoLC/ESI-MS). From these experiments an anomalous feature (gel shifting), e.g., of different folding variants, of MAT-Fel d1 in the SDS-PAGE can be concluded. This means that MAT-Fel d1 in the analyzed preparation is not suitable as biopharmaceutical molecule, in particular for clinical and/or commercial biopharmaceutical manufacturing, since its purity could not be determined with standard methods (e.g. SDS-PAGE), but only with the modified procedure explained above.

Figure 3:
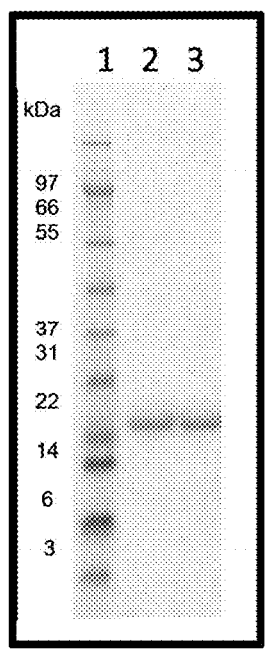

In contrast to this gel shifting phenomenon of the MAT-Fel d1 molecule, the Fel d1 as such does not show such anomalous feature in SDS PAGE (FIG. 3, lanes 2 and 3). The Fel d1 displays a single sharp band at the expected molecular weight (19.6 kD).

Figure 4:
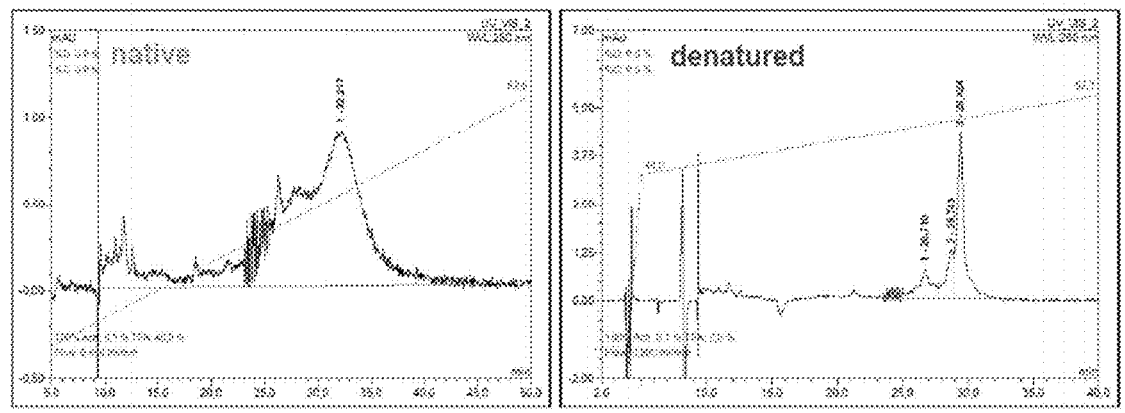

A further anomalous feature could be observed in RP-HPLC analysis. No single peak of the MAT-Fel d1 was seen in this analytical method (FIG. 4), neither in the native conformation of the protein nor in the denatured form induced by chaotropic and reducing conditions. However, for GMP certified biopharmaceutical manufacturing a single isoform of the biomolecule in marketed pharmaceutical preparations is mandatory.

Figure 5:
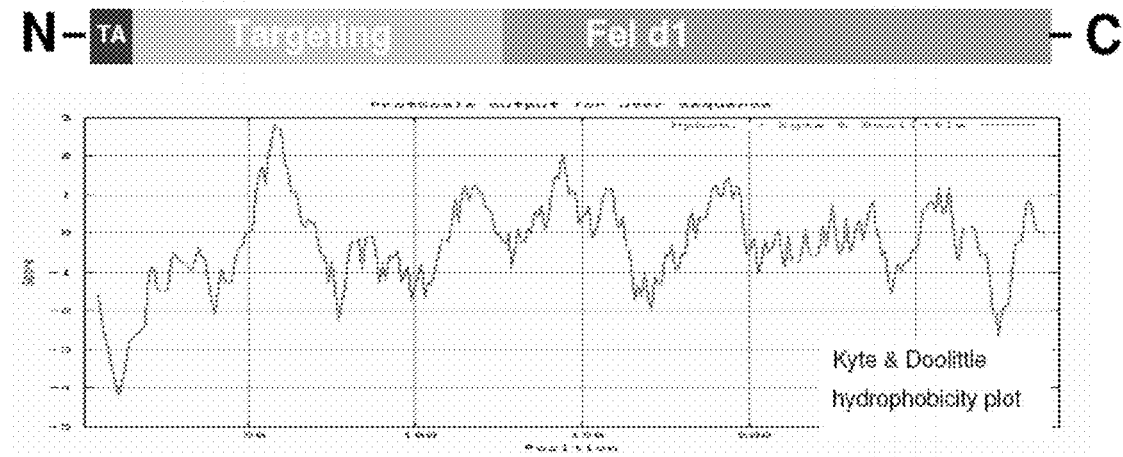

These observations in SDS-PAGE and RP-HPLC analysis may be explained by the physicochemical properties based on the amino acid sequence. Analysis in the Kyte & Doolittle hydrophobicity plot [Kyte J, Doolittle R F, Journal of Molecular Biology 1982, 157(1), 105-132] revealed adjacent extreme hydrophobic and hydrophilic domains (FIG. 5) which may be responsible for this anomalous behavior.

In particular the hydrophobic region of the targeting domain of the fusion protein is similar to the transmembrane segments of membrane proteins which are known in the art to cause such anomalous feature [Rath A et al., Proc Natl Acad Sci USA. 2009, 106(6): 1760-1765].

Migration on SDS-PAGE, that does not correlate with formula's molecular weights, termed "gel shifting" appears to be common for membrane proteins. This means, that the prerequisite of the SDS-PAGE method, which is a separation of molecules solely according to their molecular weight, independent on their native 2D- or 3D-structure does not apply in these cases. In the above cited work (PNAS article), the authors investigate the anomalous gel mobility of helical membrane proteins using a library of wild-type and mutant helix-loop-helix ("hairpin") sequences derived from transmembrane segments 3 and 4 of the human cystic fibrosis transmembrane conductance regulator (CFTR), including disease-phenotypic residue substitutions. They found that these hairpins migrate at rates of minus 10% to plus 30% vs. their actual formula's molecular weights on SDS-PAGE and load detergent at ratios ranging from 3.4-10 g SDS/g protein. They additionally demonstrated that mutant gel shifts strongly correlate with changes in hairpin SDS loading capacity, and with hairpin helicity, indicating that gel shift behavior originates in altered detergent binding. In some cases, this differential solvation by SDS may result from replacing protein-detergent contacts with protein-protein contacts, implying that detergent binding and folding are intimately linked.

The SDS PAGE (FIG. 6) as well as the RP-HPLC analysis (FIG. 4 and FIG. 7) of MAT and iMAT proteins revealed substantial differences in the migration pattern or elution, respectively. The oxidized form of MAT-Fel d1 did not show a single sharp band on the SDS-PAGE gel (Lane 3) but several diffuse bands with larger and smaller apparent molecular weights than the actual 32.2 kD of MAT-Fel d1. In contrast iMAT-Cul o4 exhibited a single sharp band (M=41.6 kD) under oxidized conditions. Also the RP-HPLC chromatogram showed a single peak (FIG. 7).

Figure 6:
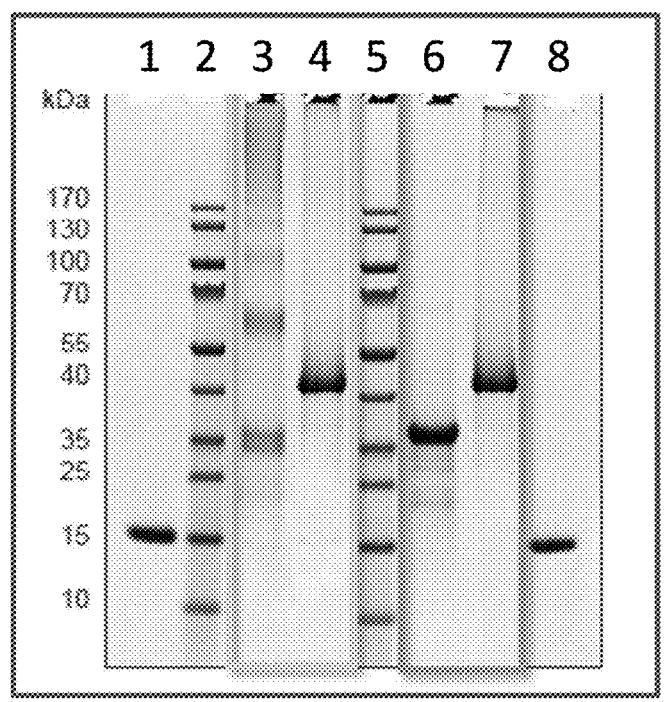
Figure 7:
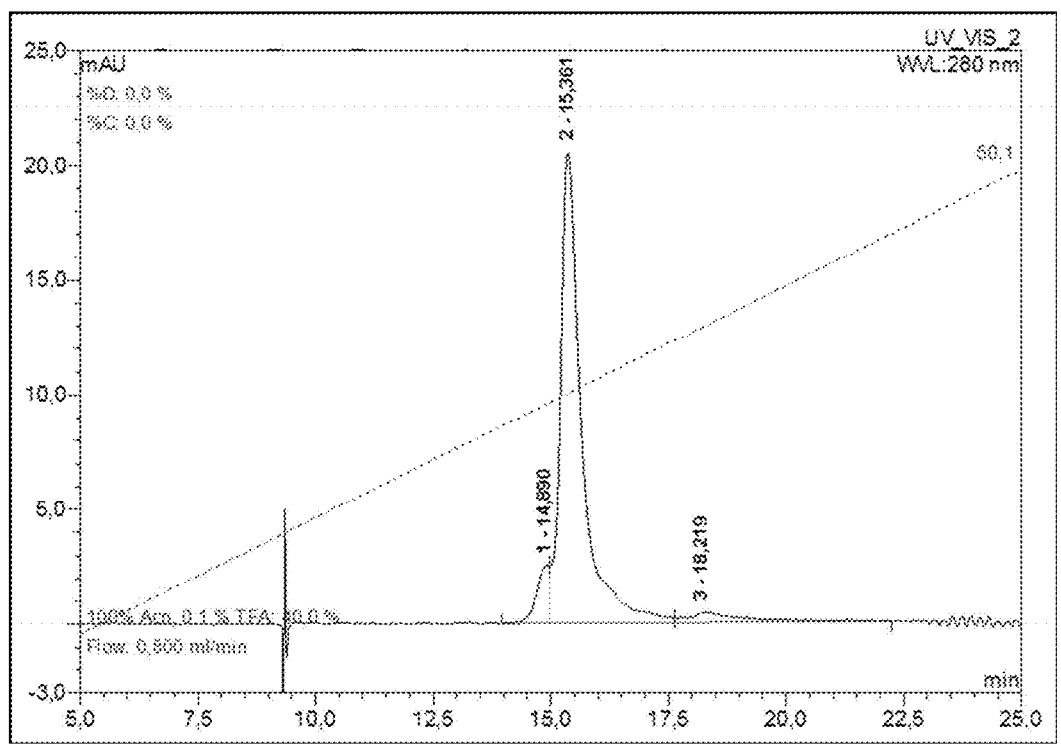
Figure 8:
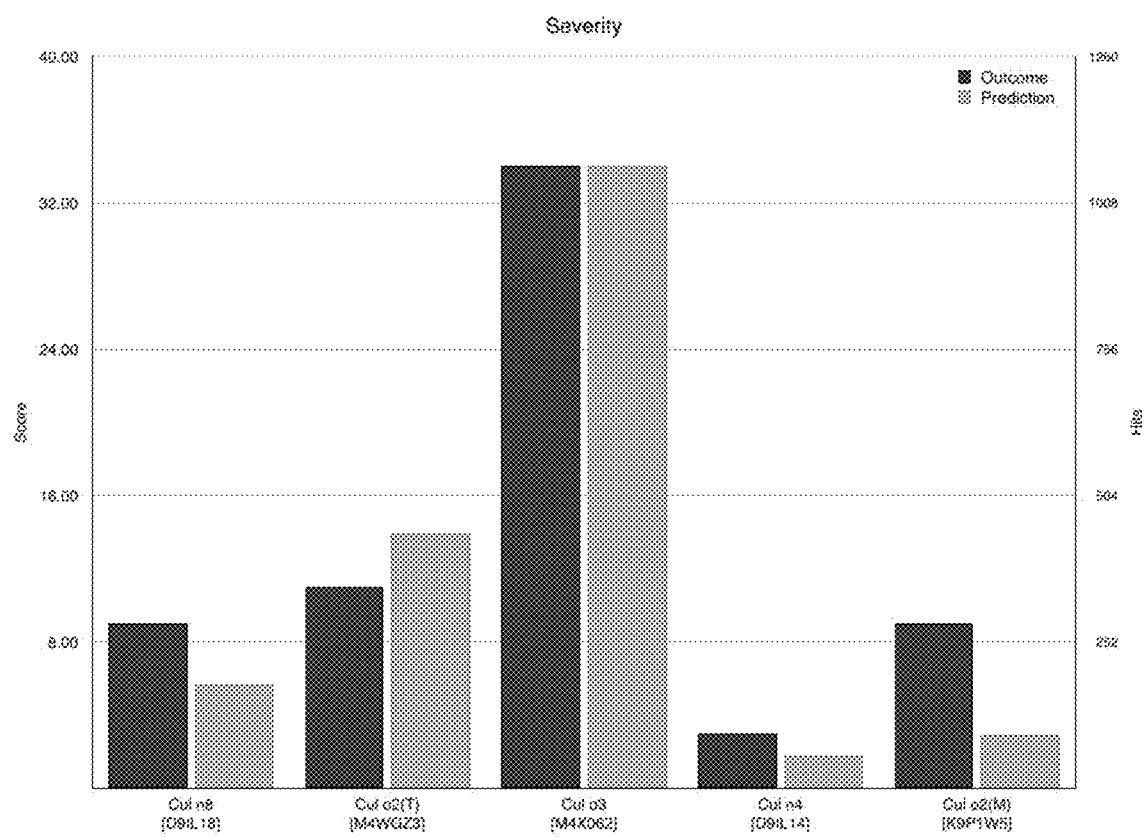

Under reducing conditions the MAT-Fel d1 in the SDS-PAGE reveals a main band migrating approximately at the known molecular weight but in addition some of the minor bands described in FIGS. 2A and 2B known to contain the complete sequence of MAT-Fel d1 emerge again (FIG. 6, lane 6). This is an attribute, which is characteristic for the anomalous feature of MAT-Fel d1. Additionally the RP-HPLC chromatogram of MAT-Fel d1 under reducing conditions (FIG. 4, right graph) exhibit at least 3 different isotypes of the MAT-Fel d1. In contrast the iMAT molecules reveal characteristics evidently indicative for a single isotype in the SDS-PAGE (FIG. 6, lane 7) as well as in the RP-HPLC (FIG. 7).

The reducing conditions lead to a cleavage of the disulfide bridges in the MAT molecule, thus the MAT and the iMAT molecules should behave alike under reducing conditions if the disulfide bridges are solely responsible for the anomalous feature of MAT. However, this is not the case, since the anomalous gel shifting and the occurrence of isoforms in RP-HPLC of MAT molecules is still present under reducing conditions.

However, the iMAT molecule does not show such gel shifting and exhibits a peak in RP-HPLC chromatogram in the native (oxidized) form of the protein. Furthermore the Kyte-Doolittle plots (Kyte, J. and Doolittle, R. 1982. A simple method for displaying the hydropathic character of a protein. J. Mol. Biol. 157: 105-132) of MAT and iMAT molecules are nearly identical at the N-terminus covering the sequence of His-tag, TAT and targeting domain (FIG. 11). Consequently, a person skilled in the art would not be motivated to construct a MAT molecule according to the prior art with cysteine residues substituted with other amino acid residues in order to overcome the disadvantages of the prior art.

The three yielded iMAT molecules have been constructed by the "bioinformatical engineering" procedures according to Example 6 below and produced by recombinant expression technology in *E. coli*. All three iMAT molecules were stable in buffer (20 mM citrate, 1 M arginine, pH 6.0) after freezing and thawing twice and could be adsorbed to ADJU-PHOS® (Brenntag, Denmark) as adjuvant, so that the iMAT molecules can be used as a vaccine. The proteins could be desorbed from ADJU-PHOS® without degradation in the same buffer system (FIG. 9).

Example 6—"Bioinformatical Engineering" of iMAT Molecules for Targeting IBH in Equines In order to, for example, treat horses with allergic insect bite hypersensitivity (IBH) using the iMAT technology effectively, it is further mandatory:
  a. to select a *culicoides* protein as allergen module in iMAT molecules that is a major allergen and thus has a high prevalence to cause hypersensitivity in affected horses and thus can also be the target for tolerance induction, and
  b. to construct an iMAT molecule with said major allergens that is thermodynamically stable and can be produced efficiently by protein engineering and can additionally be analyzed with standard methods to ensure sufficient enough quality (i.e., identity, purity and potency).

In order to fulfil these requirements, a bioinformatics approach was chosen for the selection of the allergen to be included into the iMAT molecules according to the invention. The objective of the selection was (i) to choose one or more allergens to be expected to be of relevance in IBH, i.e., that the majority of horses suffering from IBH are sensitized to the respective allergen, and (ii) to choose the allergen with the highest probability of comprising linear epitopes of allergen characteristics, i.e., comprising high numbers of short peptide sequences (7 to 13 amino acid residues) homologue to those in published allergens.

Currently approximately 230 proteins from *culicoides* (*Culicoides sonorensis, Culicoides nubeculosus, Culicoides obsoletus*) found in saliva are known that might potentially elicit allergies in subjects, e.g., equines. To select appropriate antigens for pharmaceutical preparations, a homology comparison based on local sequence alignments to known non-*culicoides* allergens was chosen. Often epitope detection for antibody recognition (mostly conformational epitopes) is achieved by functional analysis (e.g., peptide microarrays) or for T-cells epitopes (linear epitopes) by calculation of peptide binding probabilities to MHC molecules. The therapeutic principle of the iMAT technology inter alia is based on endocytosis and degradation by acid-dependent proteases in endosomes followed by MHC Class II binding and antigen presentation. In equines, the characteristics of such systems are currently not fully explored since the allelic diversity of the equine MHC genes is far less investigated as compared to the human system and thus experimentally not readily available. Furthermore the research on IBH as a Type I allergy and the causal allergens eliciting the symptoms has only recently started. The first protein characterized as allergen active in effector cells (i.e., basophil granulocytes) was not described until 2008 [Langner et al., Vet Immunol Immunopathol 2008, 122(1-2):126-137].

Thus a different—non experimental but bioinformatics—approach for allergen selection was chosen that is based on local homology searches of peptides derived from *culicoides* proteins to known non-*culicoides* allergenic proteins, most of which are known to raise allergies in humans. Amino acid sequences of proteins suspected to have allergenic properties were exported from publicly available databases (e.g., UNIPROT) and redundancies were determined by analysis of sequences homologies within the exported dataset. Highly homologue sequence counterparts were eliminated and the resulting remainder of sequences served as the canonical sequence database of probable valid antigens for subsequent analyses. To determine *culicoides* proteins with putative high allergenic potential, proteins were in silico cleaved into peptides with lengths of 6 to 15 amino acids with a one amino acid shifting. Next local-pairwise alignments of each *culicoides* protein and the corresponding peptides to the canonical sequence database were performed. Following this, a scaling of obtained alignment hits was conducted by setting the self-alignment score of a given *culicoides* protein to one and alignment hits of the corresponding peptides accordingly. Next the number of alignment hits exceeding a given threshold were counted for each peptide and compared by local-pairwise alignment to a randomly generated database of protein sequences with no known allergenic properties, and subsequently scaled and counted. The resulting "non allergic protein" counts were subtracted from those of the allergen results and cumulative hit scores for each *culicoides* protein based on the number of hits for all corresponding peptides were calculated (FIG. 12). Proteins with highest counts were selected as iMAT antigen module candidates.

For validation of the bioinformatic antigen selection method the occurrence of sensitization against five *culicoides* allergens in 13 horses suffering from clinically diagnosed IBH was measured. All selected antigens were tested in a semi-quantitative functional ex vivo experiment based on the allergen specific histamine release from equine basophiles isolated from blood samples (Histamine Release Test=HRT, details of the assay: see Example 2). The recombinant allergens were tested in 3 concentrations and the score value for each allergen ranged between 0 (no sensitization) to 6 (highest sensitization). The data from all 13 horses were compared to the results of the bioinformatics calculations (FIG. 8). This analysis shows an excellent overall correlation (r=0.97) between the sensitization (total score values per allergen of the cohort) and the prediction score. From this correlation analysis we conclude that the bioinformatics antigen selection method is suitable to select relevant *culicoides* allergens for the antigen module in iMAT molecules. Thus, the IBH affected horses can be treated with iMAT molecules according to the present invention comprising the selected allergens in order to induce tolerance against these allergens with high probability in a large proportion of the subgroup of diseased subjects.

Three allergens have been selected based on the bioinformatics analysis to be included in three different iMAT molecules, i.e., Cul o3, Cul o2 and Cul o4.

Each of the selected allergens were integrated into separate iMAT molecules as the antigen module and subsequently optimized for thermodynamic stability by iterative modeling of three-dimensional protein structures and calculation of changes of free energies after substitution of single amino acids. Physicochemical properties and stability is influenced by substituting different amino acid residue(s) within the primary amino acid sequence.

The results of the herein described analyses (antigen search and modeling) were transformed into an iMAT amino acid sequence suitable for pharmacological production and application in equines in order to treat e.g., IBH.

Example 7—Construction of Mosaic-Like iMAT Molecules According to the Invention It is expected that iMAT molecules according to the invention can further be improved if components of more than one allergen are included into the antigen module. For this purpose it is possible to apply the basic principle of the above described bioinformatics selection approach (Example 6) in a different way. Instead of selecting complete allergens based on the hit count of allergen peptides found in the allergen data base, only the most abundant peptides of several of such allergens are used to engineer an iMAT antigen module. Thus, such an iMAT molecule consists of an antigen module of peptides that stem from several allergens. This allows broadening of the spectrum of a single iMAT molecule with respect to its targeted allergic profile and is thus beneficial for pharmacological drug development.

In order to find short peptide sequences that qualify for such mosaic-like iMAT protein 230 proteins from *Culicoides* species (*Culicoides sonorensis, Culicoides nubeculosus, Culicoides obsoletus*) found in saliva were analyzed by homology comparison as described above (see Example 6). Briefly in silico cleaved *Culicoides* proteins with peptide lengths of 6-15 amino acid residues were locally aligned to a canonical sequence database of allergen-related proteins and a random database of non-allergy-related proteins. The number of differences of significant homologies for each peptide found within the canonical database was determined. Subsequently, each peptide was locally aligned to a random database triple the size of the canonical database to reduce false positive hits. The top (e.g., tenth percentile) of remaining homologies for each peptide length is especially suitable to serve as a base for construction of a mosaic-like or hybrid allergen carrying iMAT molecule. To construct a mosaic-like iMAT molecule a protein precursor is chosen (for example, from the list of precursor proteins corresponding to top ranking peptides) as a scaffold protein for embedding top ranking peptides. The signal peptide sequence is removed from the scaffold protein and top ranking peptides with additional adjacent N- or C-terminal amino acids may be inserted within the original sequence of the scaffold protein or may replace parts of the original sequence of the scaffold protein. The position for insertion or replacement is determined using similarity alignments or the reference position of the peptide in the corresponding precursor protein. As a next step, His-Tag, the TAT and targeting domain are added. Finally cysteine residues are replaced by most stabilizing residues as described above.

In an exemplary instance of this approach a salivary protein of Culicoides sonorensis (UniProt database entry "Q66U13") was used as a scaffold protein. The most allergenic structure within the protein was determined in order to conserve this part of the sequence. The signal peptide sequence is removed and subsequently sequences from UniProt database entries "Q5QBI9", "Q5QBK6", "Q5QBL6", "Q5QBJ4" and "Q5QBI2" are added. Afterwards, the mosaic-like allergen is integrated into the iMAT general molecule structure. Finally, cysteine residues are replaced by other amino acid residues, preferably serine, leucine, isoleucine and/or aspartic acid that do not derogate the stability of the constructed iMAT molecule (fusion protein).

SEQ ID NO: 17 depicts the whole sequence of an exemplary mosaic-like (hybrid) iMAT molecule according to the present invention [Amino acid residue 1: N-terminal methionine, amino acid residues 2-7: His-tag, amino acid residues 8-18: TAT sequence, amino acid residues 19-128: targeting domain, amino acid residues 129-333: hybrid allergen (scaffold protein Q66U13 without signal peptide and inserted/replaced sequences; inserted/replaced sequences: amino acid residues 137-151: Q5QBI9; amino acid residues 155-166: Q66U13; amino acid residues 185-200: Q5QBK6; amino acid residues 215-229: Q5QBL6: amino acid residues 235-250; Q5QBL6; amino acid residues 265-278: Q5QBJ4; amino acid residues 318-333: Q5QBI2; substituted cysteines (serine): 46, 146, 158, 173, 222, 225, 246, 273, 283, 329; substituted cysteines (leucine): 295; substituted cysteines (isoleucine): 299; substituted cysteines (aspartic acid): 181].

Example 8—Therapeutic Vaccine/Prophylaxis of Recurrent Airways Obstruction (RAO) in Equines A single iMAT molecule or a combination of iMAT molecules containing different antigen modules according to the present invention can be employed for treating prophylactically or therapeutically a horse suffering from or being at risk of RAO and/or summer pasture associated RAO. In horses iMAT molecules according to the present invention may be administered as described in Example 4.

Adult horses with a known history of RAO will be employed. Prior to the treatment, horses are conditioned e.g., to stand in stocks wearing a face-mask to enable a complete physical airway examination, including pneumotachograph measurements, upper airway endoscopy and bronchoalveolar lavage (BAL) for analysis of e.g., percent of neutrophils in BAL fluid. Complete blood count and biochemistry profile are performed to exclude the presence of concomitant medical conditions.

The following parameters may be investigated to examine the respiratory system and to measure efficacy of a therapeutic and/or prophylactic treatment with iMAT molecules: change in lung function variables e.g., respiratory rate, maximal transpulmonary pressure, lung resistance, and/or lung elastance. Additionally, the parameter may be incorporated into a weighted clinical scoring system e.g. also evaluating clinical scores of breathing effort/abdominal lift, nasal discharge and/or flaring, cough and/or abnormal lung, bronchial and/or tracheal sounds.

Thus, throughout the treatment period and/or thereafter the efficacy of a therapy or the prevention of RAO can be investigated clinically by quantitative, semi-quantitative or qualitative assessments.

These clinical parameters may be compared to clinical signs of the individual horse in previous seasons and/or to the severity prior to the start of a therapeutic intervention. Alternatively, a comparison to RAO affected horses that are not treated or treated with placebo may demonstrate the efficacy of the iMAT molecule-mediated treatment and/or prevention of clinical signs of RAO.

Bronchoalveolar lavage (BAL) fluid and/or fresh blood of said horses may be used in an in vitro provocation test for type 1 allergic reactions in horses, e.g., with HRT or CAST® (for details, see Example 2 and/or Hare et al Can J Vet Res 1998; 62: 133-139). A reduced pulmonary mast cell and/or basophil degranulation in response to a challenge with certain allergens, e.g., histamine and/or sulfidoleukotriene release after the iMAT molecule treatment as compared to before, indicate a therapy and/or prevention effect.

Alternatively or in addition, employing certain recombinant allergens an intradermal provocation test, skin prick test or also allergen specific IgE and/or IgG determination in BAL fluid or serum may be monitored in said horses (Tilley P et al., J Equine Vet Sci 2012, 32: 719-727). A reduced response (immediate and/or late phase reactivity) and/or changes of the antibody titers indicate a therapy and/or prevention effects of the iMAT molecule treatment.

REFERENCES (1) Akdis C A, Akdis M J, Allergy Clin Immunol 2009, 123: 735-746
(2) Allergome (www.allergome.org)
(3) Durham S R et al., J Allergy Clin Immunol 1996, 97: 1356-1365
(4) Gadermaier G et al., Molecular Immunology 2010, 47: 1292-1298
(5) Ginel P J et al., Vet. Dermatol. 2014, 25(1): 29-e10
(6) Hare J E et al., Can J Vet Res 1998, 62: 133-139
(7) James L K, Durham S R, Clin Exp Allergy 2008, 38: 1074-1088
(8) Kaul, S., Type I allergies in the horse: Basic development of a histamine release test (HRT). Doctoral thesis. Veterinary School Hannover 1998, Germany
(9) Kehrli D et al, J Vet Intern Med 2015, 29(1): 320-326
(10) Kelley J et al., Immunogenetics 2005, 56: 683-695
(11) Klein J S et al., Protein Eng Des Sel 2014, 27(10): 325-330
(12) Kyte J, Doolittle R F, Journal of Molecular Biology 1982, 157(1): 105-132
(13) Landholt G A et al., Vet Rec 2010, 167: 302-304
(14) Langner K et al., Vet Immunol Immunopathol 2008, 122(1-2):126-137
(15) Leclere Metal., Respirology 2011, 16: 1027-1046
(16) Martínez-Gómez J M et al., Allergy 2009, 64(1): 172-178

(17) Mobs C, et al., Int Arch Allergy Immunol 2008, 147: 171-178
(18) Niederberger V et al., Proc Natl Acad Sci USA 2004, 101: 14677-14682
(19) Olsen L et al., Vet. J. 2011, 187: 347-351
(20) Pires D E et al. Bioinformatics 2014, 30(3): 335-342
(21) Pirie R S, Equine Vet J 2014, 46: 276-288
(22) Rath A et al., PNAS 2009, 106(6): 1760-1765
(23) Report of the 3$^{rd}$ Havemeyer workshop on allergenic diseases of the Horse, Hólar, Iceland, June 2007, Veterinary Immunology and Immunotherapy 2008, 126: 351-361
(24) Rose H, Arb Paul Ehrlich Inst Bundesinstitut Impfstoffe Biomed Arzneim Langen Hess 2009, 96: 319-327
(25) Schaffartzik A et al., Veterinary Immunology and Immunopathology 2012, 147: 113-126
(26) Senna G et al., Curr Opin Allergy Clin Immunol. 2011, 11(4): 375-380
(27) Senti G et al., J Allergy Clin Immunol. 2012, 129(5): 1290-1296
(28) SIAF Annual Report 2010
(29) SIAF Annual Report 2011
(30) Tilley P et al., J Equine Vet Sci 2012, 32: 719-727
(31) US 2005/0281816
(32) US 2014/0105906
(33) U.S. Pat. No. 7,653,866
(34) van Bargen, K and Haas, A. FEMS Microbiol Rev 2009, 33: 870-891
(35) van der Meide N et al., Vet J 2014, 200: 31-37
(36) van Overtvelt L et al., J Immunol 2008, 180: 4514-4522
(37) Vazquez-Boland, J A et al., Vet Microbiol 2013, 167: 9-33
(38) Wacholz P A et al., J Allergy Clin Immunol 2003; 112: 915-922
(39) WO 2004/035793

In the Sequence Listing

SEQ ID NO: 1 relates to a suitable minimal amino acid sequence for one translocation module according to the present invention which is still being functional, i.e., capable of effectively promoting cell entry;
SEQ ID NO: 2 relates to the full equine invariant chain amino acid sequence;
SEQ ID NO: 3 relates to the full Cul n4 allergen amino acid sequence;
SEQ ID NO: 4 relates to the full Cul of allergen amino acid sequence;

SEQ ID NO: 5 relates to the full Cul o2 allergen amino acid sequence;

SEQ ID NO: 6 relates to the full Cul o3 allergen amino acid sequence;

SEQ ID NO: 7 relates to a Cul n4 iMAT molecule according to the present invention;

SEQ ID NO: 8 relates to a Cul n4 iMAT molecule according to the present invention;

SEQ ID NO: 9 relates to a Cul of iMAT molecule according to the present invention;

SEQ ID NO: 10 relates to a Cul of iMAT molecule according to the present invention;

SEQ ID NO: 11 relates to a Cul o2 iMAT molecule according to the present invention;

SEQ ID NO: 12 relates to a Cul o2 iMAT molecule according to the present invention;

SEQ ID NO: 13 relates to a Cul o3 iMAT molecule according to the present invention;

SEQ ID NO: 14 relates to a Cul o3 iMAT molecule according to the present invention;

SEQ ID NO: 15 relates to a specific fragment of the equine invariant chain amino acid sequence with maintained intracellular transport function;

SEQ ID NO: 16 relates to a specific fragment of the equine invariant chain amino acid sequence with maintained intracellular transport function;

SEQ ID NO: 17 relates to the whole sequence of an exemplary mosaic-like iMAT molecule according to the present invention;

SEQ ID NO: 18 relates to the full Cul o4 allergen amino acid sequence;

SEQ ID NO: 19 relates to the full Cul o7 allergen amino acid sequence;

SEQ ID NO: 20 relates to a Cul o4 iMAT molecule according to the present invention;

SEQ ID NO: 21 relates to a Cul o4 iMAT molecule according to the present invention;

SEQ ID NO: 22 relates to a Cul o7 iMAT molecule according to the present invention;

SEQ ID NO: 23 relates to a Cul o7 iMAT molecule according to the present invention.

All prior art references cited herein as well as the sequence listing accompanying this application are hereby independently from each other incorporated by reference in their entirety.

What is claimed is:

1. A method of preventing and/or treatment of insect bite hypersensitivity (IBH), urticaria or combinations thereof in equines, comprising administering a pharmaceutically effective amount of an improved Modular Antigen Transportation (iMAT) molecule comprising:
   (a) at least one first module being an amino acid sequence allowing the translocation of the iMAT molecule from the extracellular space into the interior of cells, wherein the at least one first module is selected from: (i) the amino acid sequence of HIV-tat, VP22, and/or Antennapedia, or (ii) the amino acid sequence according to SEQ ID NO: 1;
   (b) at least one second module being an amino acid sequence allowing species-specific intracellular targeting of the iMAT molecule to the cell organelles which are involved in the processing of antigens and/or the loading of MHC molecules with antigens, wherein such at least one second module comprises one of the amino acid sequences selected from: SEQ ID NOS: 2, 15, 16; and
   (c) at least one third module as antigen module being an amino acid sequence derived from at least one epitope of at least one antigen, wherein such at least one antigen is an allergen derived from blood feeding insects from the genus *Culicoides*,
   characterized in that in the entire iMAT molecule all cysteine residues are substituted with a different amino acid residue.

\* \* \* \* \*